US010473641B2

(12) United States Patent
West et al.

(10) Patent No.: US 10,473,641 B2
(45) Date of Patent: Nov. 12, 2019

(54) PREDICTING HUMAN DEVELOPMENTAL TOXICITY OF PHARMACEUTICALS USING HUMAN STEM-LIKE CELLS AND METABOLOMICS

(71) Applicant: STEMINA BIOMARKER DISCOVERY, INC., Madison, WI (US)

(72) Inventors: Paul R. West, Arena, WI (US); April M. Weir-Hauptman, Madison, WI (US); Alan M. Smith, Madison, WI (US); Elizabeth L. R. Donley, Madison, WI (US); Gabriela G. Cezar, Madison, WI (US)

(73) Assignee: Stemina Biomarker Discovery, Inc., Madison, WI (US)

( * ) Notice: Subject to any disclaimer, the term of this patent is extended or adjusted under 35 U.S.C. 154(b) by 817 days.

(21) Appl. No.: 14/257,299

(22) Filed: Apr. 21, 2014

(65) Prior Publication Data

US 2014/0273069 A1    Sep. 18, 2014

Related U.S. Application Data

(63) Continuation of application No. 13/069,326, filed on Mar. 22, 2011, now Pat. No. 8,703,424.

(60) Provisional application No. 61/394,426, filed on Oct. 19, 2010, provisional application No. 61/316,165, filed on Mar. 22, 2010.

(51) Int. Cl.
G01N 33/50 (2006.01)

(52) U.S. Cl.
CPC .................. *G01N 33/5014* (2013.01)

(58) Field of Classification Search
CPC ........... G01N 33/5014; G01N 33/5073; G01N 33/6848
See application file for complete search history.

(56) References Cited

U.S. PATENT DOCUMENTS

| | | | |
|---|---|---|---|
| 6,007,993 A | 12/1999 | Wobus | |
| 6,197,575 B1 | 3/2001 | Griffith | |
| 6,200,806 B1 | 3/2001 | Thomson | |
| 6,680,203 B2 | 1/2004 | Dasseux | |
| 6,720,188 B2 | 4/2004 | Kaddurah-Daouck | |
| 7,220,561 B2 | 5/2007 | Hermann | |
| 8,703,424 B2* | 4/2014 | West | G01N 33/5073 435/325 |
| 2002/0081626 A1 | 6/2002 | Kaddurah-Daouck | |
| 2003/0219866 A1 | 11/2003 | Kruijer | |
| 2004/0073958 A1 | 4/2004 | Katsuki | |
| 2004/0121305 A1 | 6/2004 | Wiegand | |
| 2007/0166707 A1 | 7/2007 | Schadt | |
| 2007/0248947 A1 | 10/2007 | Cezar | |
| 2008/0189792 A1 | 8/2008 | Cezar | |
| 2009/0220996 A1 | 9/2009 | Mehtal | |
| 2009/0328243 A1 | 12/2009 | Ehlich | |
| 2011/0143366 A1* | 6/2011 | Schrattenholz | G01N 33/5014 435/7.1 |

FOREIGN PATENT DOCUMENTS

| | | |
|---|---|---|
| JP | 2009-136181 | 6/2009 |
| WO | WO 02/066635 A1 | 8/2002 |
| WO | WO 03/005628 A2 | 1/2003 |
| WO | WO 2003/018760 A2 | 3/2003 |
| WO | WO 2004/059293 A2 | 7/2004 |
| WO | WO 2004/065616 A2 | 8/2004 |
| WO | WO 2005/005621 A2 | 1/2005 |
| WO | WO 2005/005662 A2 | 1/2005 |
| WO | WO 2005/080551 A2 | 9/2005 |
| WO | WO 2006/090185 A1 | 8/2006 |
| WO | WO 2006/112841 A1 | 10/2006 |
| WO | WO 2006/121952 A3 | 11/2006 |
| WO | WO 2007/120699 A2 | 10/2007 |
| WO | WO 2008/021515 A2 | 2/2008 |
| WO | WO 2008/025016 A2 | 2/2008 |
| WO | WO 2008/140463 A2 | 11/2008 |
| WO | WO 2009/151967 A1 | 12/2009 |

OTHER PUBLICATIONS

Ostea et al., Pediatr. Clin. N. Am., 51: 539-579, 2004.*
"Sweet Success Guidelines for Care", California Diabetes & Pregnancy Program, Chapter 9, 2006, pp. 1-4.*
"Life Sciences BioFiles, Metabolomics", Sigma-Aldrich, 4(8): 1-32, 2009.
Boger, Cardiovascular Res., 59: 824-33, 2003.
Bourcier, S., and Hoppilliard, Y., "Use of diagnostic neutral losses structural information on unknown aromatic metabolites: an experimental theoretical study," *Rapid Comm. Mass Spectrum*, 23:93-103, John Wiley & Sons Ltd., United Kingdom (2009).
Geier, D.A., et al., "A Prospective Study of Transsulfuration Biomarkers in Austisitic Disorders," *Neurochem. Res.* 34:386-393, Kluwer Academic Publishers-Plenum Publishers, United States (2008).
De Bree, P.K., et al., "Diagnosis of inherited adenylosuccinase deficiency by thin-layer chromatography of urinary imidazoles and by automated cation exchange column chromatography of purines," *Clinica Chimica Acta* 156:279-287, Elsevier B.V., Netherlands (1986).

(Continued)

Primary Examiner — Thaian N Ton
(74) Attorney, Agent, or Firm — Brown Rudnick LLP; Adam M. Schoen

(57) ABSTRACT

The invention provides biomarker profiles of metabolites and methods for screening chemical compounds including pharmaceutical agents, lead and candidate drug compounds and other chemicals using human stem-like cells (hSLCs) or lineage-specific cells produced therefrom. The inventive methods are useful for testing toxicity, particularly developmental toxicity and detecting teratogenic effects of such chemical compounds. Specifically, a more predictive developmental toxicity model, based on an in vitro method that utilizes both hSLCs and metabolomics to discover biomarkers of developmental toxicity is disclosed.

22 Claims, 32 Drawing Sheets

(56) References Cited

OTHER PUBLICATIONS

Jaeken, J., and Van Den Berghe, G., "An infatile autistic syndrome characterised by the presence of succinylpurines in body fluids," *Lancet* 2: 1058-1061, Lancet Publishing Group, United Kingdom (1984).
James, S.J., et al., "Metabolic Biomarkers of Increased Oxidative Stress Impaired Methylation Capacity in Children with Autism," *Am. J. Clin. Nutr.* 80:1611-1617, American Society for Nutrition, United States (2004).
Mochel, F., et al., "Elevated CSF N-acetylaspartyglutamate in patients with free sialic storage diseases," *Neurology* 74:302-305, Lippincott Williams & Wilkins, United States (2010).
Quinones, M.P., et al., "Metabolomics tools for identifying biomarkers neuropsychiatric diseases," *Neurobio. Dis.* 35:165-176, Blackwell Scientific Publications, United Kingdom (2009).
Tanaka, K., and Hine, D.G., "Compilation of gas chromatography retention indices of 163 metabolically important organic acids, and their use in detection of patients with organic acidurias," *J. Chromatogr.* 239:301-322, Elsevier Publishers B.V., Netherlands (1982).
Yap, I.K.S., et al., "Urinary Metabolic Phenotyping Differentiates Children with Autism from Their Unaffected Siblings and Age-Matched Controls," *J. Proteome Res.* 9:2996-3004, American Chemical Society, United States (2010).
"3,4-Dihydroxybenzylamine," Human Metabolome Database (Online), dated Apr. 6, 2009, accessed at: http://www.hmdb.ca/metabolites, Accession No. HMDB12153.
"3-carboxy-1-hydroxypropylthiamine diphosphate," Human Metabolome Database (Online), dated Jun. 11, 2008, accessed at: http://www.hmdb.ca/metabolites, Accession No. HMDB06744.
3-Sialyllactosamine, Human Metabolome Database (Online), dated May 25, 2007, accessed at: http://www.hmdb.ca/metabolites, Accession No. HMDB06607.
"5-Hydroxylysine," Human Metabolome Database (Online), dated Nov. 16, 2005, accessed at http://www.hmdb.ca/metabolites, Accession No. HMDB00450.
"DL-2-Aminooctanoic acid," Human Metabolome Database (Online), dated Nov. 16, 2005, accessed at http://www.hmdb.ca/metabolites, Accession No. HMDB00991.
"L-Cystathionine," Human Metabolome Database (Online), dated Nov. 16, 2005, accessed at http://www.hmdb.ca/metabolites, Accession No. HMDB00099.
"N-Acetylaspartyglutamic acid," Human Metabolome Database (Online), dated Nov. 16, 2005, accessed at http://www.hmdb.ca/metabolites, Accession No. HMD1301067.
"PC (16:0/16:0)," Human Metabolome Database (Online), dated Nov. 16, 2005, accessed at http://www.hmdb.ca/metabolites, Accession No. HMDB00564.
"Proline betaine," Human Metabolome Database (Online), dated Aug. 24, 2006, accessed at http://www.hmdb.ca/metabolites, Accession No. HMDB04827.
"SAICAR," Human Metabolome Database (Online), dated Nov. 16, 2005, accessed at: http://hmdb.ca/metabolites, Accession No. HMDB00797.
"Vinylacetylglycine," Human Metabolome Database (Online), dated Nov. 16, 2005, accessed at http://www.hmdb.ca/metabolites, Accession No. HMDB00894.
Canadian Office Action for Patent No. 2,675,997, dated Feb. 24, 2011, Canadian Intellectual Property Office, 4 pages.
Canadian Office Action for Patent No. 2,648,218, dated Jun. 8, 2011, Canadian Intellectual Property Office, 6 pages.
English translation of Japanese Patent Office Action for Appl. No. 2009-505452, dated Jun. 2, 2011, 5 pages.
Office Action dated Oct. 12, 2011 in U.S. Appl. No. 12/023,868, inventors Cezar, G., et al., filed Jan. 31, 2008, 8 pages.
The International Search Report and the Written Opinion of the International Searching Authority for International Patent Appl. No. PCT/US2011/034654, 27 pages, dated Oct. 13, 2011.

Hayman, M.W., and Przyborski, S.A., "Proteomic identification of biomarkers expressed by human pluripotent stem cells," *Biochem. Biophys. Res. Commun.* 316:918-923, Elsevier Inc., United States (2004).
Harrigan, G.G., et al., "Medicinal Chemistry, Metabolic Profiling and Drug Target Discovery: A Role for Metabolic Profiling in Reverse Pharmacology and Chemical Genetics," *Mini-Reviews in Medicinal Chemistry* 5:13-20, Bentham Science Publishers Ltd., Netherlands (2005).
Adab, N., et al., "The longer term outcome of children born to mothers with epilepsy," *J. Neurol. Neurosurg. Psychiatry* 75:1575-1583, British Medical Association, United Kingdom (2004).
Allevi, P., et al., "The first synthesis of glucosylgalactosyl hydroxylysine (Glu-Gal-Hyl), and important biological indicator of collagen turnover," *Bioorg. Med. Chem. Lett.* 14:3319-3321, Elsevier Science, United Kingdom (2004).
Apodaca, G., et al., "Expression Inhibitors of Metalloproteinases and Metalloproteinase Inhibitors by Fetal Astrocytes and Glioma Cells," *Cancer Res.*, 50:2322-2329, American Association for Cancer Research (1990).
Barry, et al., "Immunogenicity of Adult Mesenchymal Stem Cells: Lessons from the Fetal Allograft," *Stem Cells Dev.* 14:252-265, Mary Ann Liebert, Inc., United States (2005).
Beckman, D. and Brent, R., "Mechanism of Teratogenesis," *Annu. Rev. Pharmacol.* 24:483-500, Annual Reviews, Inc., United States (1984).
Berge, K., et al., "Impact of mitochondrial .beta.-oxidation in fatty acid-mediated inhibition of glioma cell proliferation," J. Lipid Res. 44:118-127, Lipid Research, Inc., United States (2003).
Bezabeh, T., et al., "Prediction of Treatment Response in Head and Neck Cancer by Magnetic Resonance Spectroscopy," *AJNR Am. J. Neuroradiol.* 26:2108-2113, American Society of Neuroradiology, United States (2005).
Bhogal, N., et al., "Toxicity testing: creating a revolution based on new technologies," *Trends Biotechnol.* 23:299-307, Elsevier Ltd., Netherlands (2005).
Bjerkedal, T., et al., "Valproic Acid and Spina Bifida," *Lancet* 2:1096, Lancet Publishing Group, United Kingdom (1982).
Bonda, D., et al., "Indoleamine 2,3-dioxygenase and 3-hydroxykynurenine modifications are found in the neuropathology of Alzheimer's disease," *Redox Rep.* 15:161-168, W. S. Maney and Son, United Kingdom (2010).
Brent, R. and Beckman, D., "Enviromental Teratogens," *Bull. N.Y. Acad. Med.* 66:123-163, New York Academy of Medicine, United States (Mar.-Apr. 1990).
Brown, J. and Wilson, W., "Exploiting Tumour Hypoxia in Cancer Treatment," *Natl. Rev. Cancer* 4:437-447, Nature Publishing Group, United Kingdom (2004).
Camphausen, K., et al., "Orthotopic Growth of Human Glioma Cells Quantitatively and Qualitatively Influences Radiation-Induced Changes in Gene Expression," *Cancer Res.* 65:10389-10393, American Association for Cancer Research, United States (2005).
"Cancer Facts & Figures 2007," American Cancer Society, Atlanta, Georgia, United States (2007), 56 pages.
Capuron, L., et al., "Interferon-Alpha-Induced Changes in Tyrptophan Metabolism: Relationship to Depression and Paroxetine Treatment," *Biol. Psychiatry* 54:906-914, Elsevier, United States (2003).
"Chemical Hazard Data Availability Study: What Do We Really Know About the Safety of High Production Volume Chemicals," EPA's 1998 Baseline of Hazard Information that is Readily Available to the Public, Office of Pollution Prevention and Toxins, Environment Protection Agency (EPA)(1998), 35 pages.
Cezar, G., et al., "Identification of Small Molecules from Human Embryonic Stem Cells Using Metabolomics," *Stem Cells Dev.* 16:869-882, Mary Ann Liebert, Inc., United States (2007).
Chace, D., et al., Rapid diagnosis of MCAD deficiency: quantitative analysis of octanoylcarnitine and other acylcarnitines in newborn blood spots by tandem mass spectrometry, Clin. Chem. 43:2106-2113, American Association for Clinical Chemistry, United States (1997).
Chang, S., et al., "Phase II Study of Phenylacetate in Patients With Recurrent Malignant Glioma: A North American Brain Tumor

(56) References Cited

OTHER PUBLICATIONS

Consortium Report," J. Clin. Oncol. 17:984-990, American Society of Clinical Oncology, United States (1999).
Chen, M., et al., "Metabonomic Study of Aristolochic Acid-Induced Nephrotoxicity in Rats," J. Proteome Res. 5:995-1002, American Chemical Society, United States (2006).
Chiarugi, A., et al., "Similarities and differences in the neuronal death processes activated by 3OH-kynurenine and quinolinic acid," J. Neurochem. 77:1310-1318, Blackwell Science, United Kingdom (2001).
Chugani, D., "Serotonin in Autism and Pediatric Epilepsies," Ment. Retard Dev. Disabil. Res. Rev. 10:112-116, Wiley-Liss, United States (2004).
Claudio, L., "NIEHS Investigates Links between Children, the Environment, and Neurotoxicty," Environ. Health Perspect. 109:A258-A261 (Jun. 2001).
Coecke, S., et al., "The value of alternative testing for neurotoxicity in the context of regulatory needs," Environ. Toxicol. and Pharmacol. 21:153-167, Elsevier B.V., Netherlands (2006).
Copland, I., et al., "CD34 expression on murine marrow-derived mesenchymal stromal cells: impact on neovascularization," Exp. Hematol. 36:93-103, Elsevier Science Inc., Netherlands (2008).
Cravatt, B., et al., "Molecular characterization of an enzyme that degrades neuromodulatory fatty-acid amides," Nature 384:83-87, Nature Publishing Group, United Kingdom (1996).
Crockford, D., et al., "Statistical Heterospectroscopy, and Approach to the Integrated Analysis of NMR and UPLC-MS Data Sets: Application in Metabonomic Toxicology Studies," Analy. Chem. 78:363-371, American Chemical Society, United States (Jan. 2006).
Daston, G. and Naciff, J., "Gene expression changes related to growth and differentiation in the fetal and juvenile reproductive system of the female rat: evaluation of microarray results," Reprod. Toxicol. 19:381-394, Pergamon Press, United States (2005).
Davis, F., et al., "Acting Via a Cell Surface Receptor, Thyroid Hormone is a Growth Factor for Glioma Cells," Cancer Res. 66:7270-7275, American Association for Cancer Research, United States (2006).
Dehoon, M., et al., "Predicting gene regulation by sigma factors in Bacillus sublilis from genome-wide data," Bioinformatics 20(Suppl. 1): i101-i108, Oxford University Press, United Kingdom (2004).
Delaney, J., et al., "Phenylacetylglycine, a putative biomarker of phospholipidosis: its origins and relevance to phospholipid accumulation using amiodarone treated rats as a model," Biomarkers 9:271-290 ,Taylor & Francis Ltd., United Kingdom (2004).
Dettmer, K., et al., "Mass Spectrometry-Based Metabolomics," Mass Spectrom. Rev. 26:51-78, Wiley Periodicals, Inc., United States (2005).
English, K., et al., "IFN-gamma and TNF-alpha differentially regulate immunomodulation by murine mesenchymal stem cells," Immunol Lett. 110:91-100, Elsevier/North-Holland Biomedical Press, Netherlands (2007).
Evelhoch, J., et al., "Expanding the Use of Magnetic Resonance in the Assessment of Tumor Response to Therapy: Workshop Report," Cancer Res. 65:7041-7044, American Association for Cancer Research, United States (2005).
Fella, K., et al., "Use of two-dimensional gel electrophoresis in predictive toxicology: Identification of potential early protein biomarkers in chemically induced hepatocarcinogenesis," Protemics 5:1914-1921, Wiley-VCH, Germany (2005).
Fiehn, O., "Metabolomics—the link between genotypes and phenotypes," Plant Mol. Biol. 48:155-171, Kluwer Academic, Netherlands (2002).
Franks, M., et al., "Thalidomide," Lancet 363:1802-1811, Lancet Publishing Group, United Kingdom (2004).
Gallo, M., et al., "Limited plasticity of mesenchymal stem cells cocultured with adult cardiomyocytes," J. Cell Biochem. 100:86-99, Wiley-Liss, United States (2007).
Garrod, S., et al., "Integrated Metabonomic Analysis of the Multiorgan Effects of Hydrazine Toxicity in the Rat," Chem. Res. Toxicol. 18:115-122, American Chemical Society, United States (2005).

Gillies, R., et al., "Applications of Magnetic Resonance in Model Systems: Tumor Biology and Physiology," Neoplasia 2:139-151, Stockton Press, United States (2000).
Grande, S., et al., Radiation Effects on Soluble Metabolites in Cultured HeLa Cells Examined by HMRS, Int. J. Cancer 96:27-42, Wiley-Liss, Inc., United States (2000).
Greaves, P., et al., "First Dose of Potential New Medicines to Humans: How Animals Help," Nat. Rev. Drug Discov. 3:226-236, Nature Publishing Group, United Kingdom (2004).
Griffin, J. and Bollard, M., "Metabonomics: Its Potential as a Tool in Toxicology for Safety Assessment and Data Integration," Curr. Drug Metab. 5:389-398, Bentham Science Publishers, Ltd., United States (2004).
Griffin, J. and Schockcor, J., "Metabolic Profiles of Cancer Cells," Nat. Rev. Cancer 4:551-561, Nature Publishing Group, United Kingdom (2004).
Groenen, P., et al., "High-resolution H NMR spectroscopy of amniotic fluids from spina bifida fetuses and controls," Eur. J. Obstet. Gynecol. Reprod. Biol. 112:16-23, Elsevier Scientific Publishers, Netherlands (2004).
Guerro, P., "Toxic Substances Control Act: Preliminary Observations on Legislative Changes to Make TSCA More Effective," Testimony dated Jul. 13, 1994, Report No. GAO/T-RCED-94-263, United States General Accounting Office (GAO), United States (1994), 16 pages.
Guillemin, C., et al., "Quinolinic acid selectively induces apoptosis of human astrocytes: potential role in AIDS dementia complex," J. Neuroinflammation 2:16, BioMed Central, United Kingdom (2005).
Hareng, L., et al., "The Integrated Project ReProTect: A novel approach in reproductive toxicity hazard assessment," Reprod. Toxicol. 20:441-452, Pergamon Press, United States (Sep. 2005).
He, J., et al., "Human Embryonic Stem Cells Develop Into Multiple Types of Cardiac Myocytes: Action Potential Characterization," Circ. Res. 93:32-39, American Heart Association, Inc., United States (2003).
Heesters, M., et al., "Localized proton spectroscopy of inoperable brain gliomas. Response to radiation therapy," J. Neuro-Oncology 17:27-35, Kluwer Academic Publishers, Netherlands (1993).
Hofbauer, K., et al., "Oxygen tension regulates the expression of a group of procollagen hydroxlyases," Eur. J. Biochem. 270:4515-4522, Springer, United States (2003).
Huuskonen, H., "New models and molecular markers in evaluation of developmental toxicity," Toxicol. Appl. Pharmacol. 207(2 Suppl):495-500, Elsevier, Netherlands (2005).
Isobe, T., et al., "Changes in H-MRS in glioma patients before and after irradiation: the significance of quantitative analysis of choline-containing compounds," MEDLINE Database Accession No. NLM12616652, U.S. National Library of Medicine, Bethesda, Maryland, United States (2003), 1 page.
Jaishankar, A., et al., "Human embryonic and mesenchymal stem cells express different nuclear proteomes," Stem Cells Dev. 18:793-802, Mary Ann Liebert, Inc., United States (2009).
Jakobs, B. and Wanders, R., "Fatty acid .beta.-oxidation in peroxisomes and mitochondria: the first, unequivocal evidence for the involvement of carnitine in shuttling propionyl-CoA from peroxisomes to mitochondria," Biochem. Biophys. Res. Commun. 213:1035-1041, Academic Press, United States (1995).
Jensen, R., "Hypoxia in the tumorigenesis of gliomas and as a potential target for the therapeutic measures," Neurosurg. Focus 20:E24, American Association of Neurological Surgeons, United States (2006).
Jogl, G., et al., "Structure and Function of Carnitine Acyltransferases," Ann. NY Acad. Sci. 1033:17-29, New York Academy of Sciences, United States (2004).
Kaminaga, T. and Shirai, K., "Radiation-induced brain metabolic changes in acute and early delayed phase detected with quantitative proton magnetic resonance spectroscopy," J. Comput. Assist. Tomogr. 29:293-297, Lippincott Williams & Wilkins, United States (2005).
Khodarev, N., et al., "Dose-dependent and independent temporal patterns of gene responses to ionizing radiation in normal and tumor cells and tumor xenografts," Proc. Natl. Acad. Sci. USA 98:12665-12670, National Academy of Sciences, United States (2001).

(56) References Cited

OTHER PUBLICATIONS

Kocki, T., et al., "Enhancement of brain kynurenic acid production by anticonsulvants—Novel mechanism of antiepileptic activity?," *Eur. J. Pharmacol.* 541:147-151, Elsevier, B.V., Netherlands (2006).

Kohl, C., et al., "Measurement of tryptophan, kynurenine and neopterin in women with and without postpartum blues," *J. Affect. Disord.* 86:135-142, Elsevier/North-Holland Biomedical Press (2005).

Lenz, E., et al., "A metabonomic investigation of the biochemical effects of mercuric chloride in the rat using H NMR and HPLC-TOF/MS: time dependent changes in the urinary profile of endogenous metabolites as a result of nephrotoxicity," *Analyst* 129:535-541, Royal Society of Chemistry, United Kingdom (2004).

Levenstein, M., et al., "Basic Fibroblast Growth Factor Support of Human Embryonic Stem Cell Self Renewal," *Stem Cells* 24:568-574, AlphaMed Press, United States (2005).

Lieb, K., et al., "Serotonin via 5-HT7 receptors activates p38 mitogen-activated protein kinase E and protein kinase C epsilon resulting in interleukin-6 synthesis in human U373 MG astrocytoma cells," *J. Neurochem.* 93:549-559, Blackwell Science, United Kingdom (2005).

Lindon, J., et al., "Contemporary issues in toxicology the role of metabonomics in toxicology and its evaluation by the COMET project," *Toxicol. Appl. Pharmacol.* 187:137-146, Academic Press, United States (Mar. 2003).

Liou, J., et al., "Protection of Endothelial Survival by Peroxisome Proliferator-Activaled Receptor-.delta. Mediated 14-3-3 Upregulation," *Arterioscler. Thromb. Vasc. Biol.* 26:1481-1487, American Heart Association, United States (2006).

Livak, K. and Schmittgen, T., "Analysis of Relative Gene Expression Data Using Real-Time Quantitative PCR and the $2^{-\Delta\Delta CT}$ Method," *Methods* 25:402-408, Academic Press, United States (2001).

Li, E., et al., "Targeted Mutation of the DNA Methyltransferase Gene Results in Embryonic Lethality," *Cell* 69:915-926, Cell Press, United States (1992).

Li, Y., et al., "Expansion of Human Embryonic Stem Cells in Defined Serum-Free Medium Devoid of Animal-Derived Products," *Biotechnol. Bioeng.* 91:688-698, Wiley, United States (2005).

Ludwig, T., et al., "Feeder-independent culture of human embryonic stem cells," *Nat. Methods* 3:637-646, Nature Publishing Group, United Kingdom (2006).

Mansour, H., "Protective role of carnitine ester against radiation-induced oxidative stress in rats," *Pharmacol. Res.* 54:165-171, Elsevier Ltd., Netherlands (2006).

McKnight, T., "Proton Magnetic Resonance Spectroscopic Evaluation of Brian Tumor Metabolism," *Semin Oncol.* 31:605-617, Elsevier Inc., Netherlands (2004).

McNeish, J., "Embryonic Stem Cells in Drug Discovery," *Nat. Rev. Drug Discov.* 3:70-80, Nature Publishing Group, United Kingdom (2004).

Meador, J., et al., "In utero antiepiletic drug exposure: fetal death and malformations," *Neurology* 67:407-412, Lippincott, Williams & Wilkins, United States (2006).

Meisel, R., et al. "Human bone marrow stromal cells inhibit allogeneic T-cell responses by indoleamine 2,3-dioxygenase-mediated tryptophan degradation," *Immunobiology* 103:4619-4621, The American Society of Hematology, United States (2004).

Miller, A., et al., "Modulation of radiation response of human tumour cells by the differentiation inducers, phenylacetate and phenylbutyrate," *Int. J. Radiat. Biol.* 72:211-218, Taylor & Francis, United Kingdom (1997).

Miller, A. et al., "Phenylacetate-Induced Modulation of Radionat Response in Prostate Carcinoma, Breast Adenocarcinoma and Glioblastoma Cell Lines: Time Factor and Mechanistic Considerations," *Proc. Am. Assoc.*, Cancer Res. 36:606, Abstract No. 3604, American Association of Cancer Research, United States (1995).

Miller, C., et al., "Upregulation of the Initiating Step of the Kynurenine Pathway in Postmortem Anterior Cingulate Cortex from Individuals with Schizophrenia and Bipolar Disorder," *Brain Res.*, 16:25-37, Elsevier, Netherlands 2006).

Miyazaki, K., et al., "Maternal administration of thalidomide or valproic acid causes abnormal serotonergic neurons in the offspring: implication for pathogenesis of autism," *Int. J. Dev. Neurosci.* 23:287-297, Elsevier Science, United Kingdom (2005).

Mravec, B., "Salsonlinol, a Derivate of Dopamine, is a Possible Modulator of Catecholaminergic Transmission: a Review of Recent Developments," *Physiol. Res.* 55:353-364, Institute of Physiology, Academy of Sciences of the Czech Republic, Czech Republic (2006).

Napierala, D., et al., "Mutations and promoter SNPs in RUNX2, a transcriptional regulator of bone formation," *Mol. Genet. Metab.* 86:257-268, Elsevier, Netherlands (2005).

Narita, N., et al., "Increased Monamine Concentration in the Brain and Blood of Fetal Thalidomide- and Valporic Acid-Exposed Rat: Putative Animal Models for Autism," *Pediatr. Res.* 52:576-579, Lippincott Williams & Wilkins, United States (2000).

Nauman, P., et al., "The concentration of thyroid hormones and activities of iodolhyronine deiodinases are altered in human brain gliomas," *Folia Neuropathol.* 42:67-73, Medical Publishing House, Poland (2004).

Nemeth, H., et al., "Role of Kynurenines in the Central and Peripheral Nervous Systems," *Curr. Neurovasc. Res.* 2:249-260, Bentham Science Publishers, Netherlands (2005).

Nicholson, J., et al., "Metabonomics: a platform for studying drug toxicity and gene function," *Nat. Rev. Drug Discov.* 1:153-161, Nature Publishing Group, United Kingdom (2002).

Nicholson, J., et al., "'Metabonomics': understanding the metablic responses of living systems to pathophysiological stimuli via multivariate statistical analysis of biological NMR spectroscopic data," *Xenobiotica* 29:1181-1189, Taylor & Francis, United Kingdom (1999).

Okada, A., et al., "Polycomb Homologs Are Involved in Teratogenicity Valproic Acid in Mice," *Birth Defects Res. A Clin. Mol. Teratol.* 70:870-879, John Wiley & Sons, United States (2004).

Ono, S., et al., "Urinary Collagen Metabolite Excretion in Amyotrophic Lateral Sclerosis," *Muscle & Nerve* 24:821-825, John Wiley & Sons, Inc., United States (2001).

Ornoy, A. and Diav-Citrin, O., et al., "Fetal effects of primary and secondary cytomegalovirus infection in pregnancy," *Reprod. Toxicol.* 21:399-409, Pergamon Press, United States (2006).

Ott, K., et al., "Metabolic Imaging Predicts Response, Survival, and Recurrence in Adenocarcinomas of the Esophagogastric Junction," *J. Clin. Oncol.* 24:4692-4698, American Society of Clinical Oncology, United States (2006).

Ozawa, T., et al., "Radiopotentiation of human brain tumor cells by sodium phenylacetate," *Cancer Lett.* 142:139-146, Elsevier/North-Holland, Netherlands (1999).

Pausescu, E. et al., "Early effects of $^{60}$Co gamma-radiation on cerebral catecholamines, serotonin and related compounds," *Strahlentherapie* 145:76-82, Urban & Schwarzenberg, Germany (1973).

Peacock, K. and Lesser, G., "Current Therapeutic Approaches in Patients with Brain Metastases," *Curr. Treat Options Oncol.* 7:479-489, Current Science, Inc., United States (2006).

Pellizzer, C., et al., "Developmental Toxicity Testing From Animal Towards Embryonic Stem Cells," *ALTEX* 22:47-57, Spektrum Akademischer Verlag, Germany (2005).

Perici , D., et al., "Excretion of Metabolites of Biogenic Amines in Patients with Irradiated Brain Tumors," *Acta Radiol. Ther. Phys. Biol.* 15:81-90, Institute Rudjer Boskovic, Yugoslavia (2006).

Perkins, M. and Stone, T., "An iontophoretic investigation of the actions of convulsant kynurenines and their interaction with the endogenous excitant quinolinic acid," *Brain Res.* 247:184-187, Elsevier, Netherlands (1982).

Piersma, A., "Validation of alternative methods for developmental toxicity testing," *Toxicology Lett.* 149:147-153, Elsevier, Netherlands (2004).

Poirier, Y., et al., "Peroxisomal beta-oxidation—a metabolic pathway with multiple functions," *Biochem. Biophys. Acta* 1763:1413-1426, Elsevier, Netherlands (2006).

"Radiation Therapy for Cancer," accessed at: http://www.cancer.gov/cancertopics/factsheet/Therapy/radiation, dated Jan. 28, 2006,

(56) References Cited

OTHER PUBLICATIONS accessed on Dec. 28, 2005, National Cancer Institute at the National Institutes of Health, United States, 11 pages.
Rasalam, A., et al., "Characteristics of fetal anticonvulant syndrome associated autistic disorder," *Dev. Med. Child Neuro.* 47:551-555, Blackwell, United Kingdom (2005).
Reilly, S., et al., "A peroxisomal acyltransferase in mouse identifies a novel pathway for taurine conjugation of fatty acids," *FASEB J.* 21:99-107, The Federation, United States (2007).
Reubinoff, B., et al., "Embryonic stem cell lines from human blastocysts: somatic differentiation in vitro," *Nat. Biotechnol.* 18:399-404, Nature America Publishing, United States (2000).
Roche, S., et al., "Comparative proteomic analysis of human mesenchymal and embryonic stem cells: towards the definition of a mesenchymal stem cell proteomic signature," *Proteomics* 9:223-232, Wiley-VCH, Germany (2009).
Rosano, A., et al., "Infant mortality and congenital anomalies from 1950 to 1994: an international perspective," *J. Epidemiol.* Community Health 54:660-666, British Medical Association, United Kingdom (2000).
Rose, R., et al., "Bone marrow-derived mesenchymal stromal cells express cardiac-specific markers, retain the stromal phenotype, and do not become functional cardiomyocytes in vitro," *Stem Cells* 26:2884-2892, AlphaMed Press, United States (2008).
Sabatine, M., et al., "Metabolomic Identification of Novel Biomarkers of Mycardial Ischemia," *Circulation* 112:3868-3875, American Heart Association, Inc., United States (2005).
Saghatelian, A., et al., "Assignment of Endogenous Substrates to Enzymes by Global Metabolite Profiling," *Biochemistry* 43:14332-14339, American Chemical Society, United States (2004).
Salo, A., et al., "Lysyl Hydroxylase 3 (LH3) Modifies Proteins in the Extracellular Space, a Novel Mechanism for Matrix Remodeling," *J. Cell Physiol.* 207:644-653, Wiley-Liss, United States (2006).
Samid, D., et al., "Selective Activity of Phenylacetate against Malignant Gliomas: Resemblance to Fetal Brain Damage in Phenylketonuria," *Cancer Res.* 54:891-895, American Association for Cancer Research, United States (1994).
Sandikci, K., et al., "Total Acid Soluble and Insoluble Carnitine Levels in Human Brain Tumors," *Cancer Biochem. Biophys.* 17:49-57, Gordon and Breach Science Publishers, United Kingdom (1999).
Sapira, J., "The determination of urinary 3-methoxy-4-hydroxy-mandelic acid and free 3-methoxy-4-hydroxy-phenylglycol," *Clin. Chim. Acta.* 20:139-145, Elsevier, Netherlands (1968).
Scheurer, S., "Modulation of gene expression by hypoxia in human umbilical cord vein endothelial cells: A transcriptomic and proteomic study," *Proteomics* 4:1737-1760, Wiley-VCH, Germany (2007) (erratum in: Proteomics 4:2822(2004)).
Scholz, G., et al., "Prevalidation of the Embryonic Stem Cell Test (EST)—A New In Vitro Embryotoxicity Test," *Toxicology In Vitro* 13:675-681, Elsevier Science Ltd., United Kingdom (1999).
Shaw, G., et al., "Periconceptional Vitamin Use,.Dietary Folate, and the Occurrence of Neural Tube Defects," *Epidemology* 6:219-226, Blackwell Scientific Publications, United States (1995).
Shi, C., et al., "HRMAS 1H-NMR measured changes of the metabolite profile as mesenchymal stem cells differentiate to targeted fat cells in vitro: implications for non-invasive monitoring of stem cell differentiation in vivo," *J. Tissue Eng. Regen. Med.* 2:482-490, John Wiley & Sons, United Kingdom (2008).
Soga, T., et al., "Differential Metabolomics Reveals Ophthalmic Acid as an Oxidative Stress Biomarker Indicating Hepatic Glutathione Consumption," *J. Biol. Chem.* 281:16788-16778, The American Society for Biochemistry and Molecular Biology, Inc., United States (2006).
Spielmann, et al., "The Embryonic Stem Cell Test, an In Vitro Embryotoxicity Test Using Two Permanent Mouse Cell Lines: 3T3 Fibroblasts and Embryonic Stem Cells," in *Vitro Toxicology* 10:119-127 (1997).
Stone, T. and Darlington, L., "Endogenous kynurenines as targets for drug discovery and development," Nat Rev. Drug Discov. 1:609-620, *Nature* Publishing Group, United Kingdom (2002).
Stupp, R., et al., "Radiotherapy plus Concomitant and Adjuvant Temozolomide for Glioblastoma," *N. Engl. J. Med.* 352:987-996, Massachusetts Medical Society, United States (2005).
Szkandernova, S., et al., "Proteome Alterations in Gamma-Irradiated Human T-Lymphocyte Leukemia Cells," Radiat. Res. 163:307-315, Kluge Carden Jennnings Publishing Company, United States (2005).
Taylor, M., et al., "Relationship between interferon-gamma, indoleamine 2,3-dioxygenase, and tryptophan catabolism," *FASEB J.* 5:2516-2522, The Federation, United States (1991).
Thomson, J., et al., "Embryonic stem cell lines derived from human blastocysts," *Science* 282:1145-1147, American Association for the Advancement of Science, United States (1998).
Tiboni, G., et al., "Production of Axial Skeletal Malformations with the Nitric Oxide Synthesis Inhibitor NG-Nitro-L-Arginine Methyl Ester (L-NAME) in the Mouse," *Birth Defects Res. B. Dev. Reprod. Toxicol.* 80:28-33, Wiley-Liss, United States (2003).
Trosko, J., "Use of human embryonic and adult stem cells for drug screening and safety assessment," *Toxicology* 226:31, Elsevier Ireland Ltd., Ireland (Sep. 2006).
Van Der Leij, F., et al., "Genomics of the Human Carnitine Acyltransferase Genes," *Mol. Genet. Metab.* 71:139-153, Elsevier, Netherlands (2000).
Van Maldegem, B., et al., "Clinical, biochemical, and genetic heterogeneity in short-chain acyl-coenzyme A dehydrogenase deficiency," *JAMA* 296:943-952, American Medical Association, United States (2006).
Van Ravenzwaay, B., et al., "The use of metabolomics for the discovery of new biomarkers of effect," *Toxicol. Lett.* 172:21-28, Elsevier, Netherlands (2007).
Vanella, A., et al., "L-Propionyl-carnitine as superoxide scavenger, antioxidant, and DNA cleavage protector," *Cell Biol. Toxicol.* 16:99-104, Kluwer Academic Publishers, Netherlands (2000).
Vaz, F. and Wanders, J., "Carnitine biosynthesis in mammals," *Biochem. J.* 361:417-429, Biochemical Society, United Kingdom (2002).
Viant, M., et al., "NMR-derived developmental metabolic trajectories: an approach for visualizing the toxic actions of trichloroethylene during embryogenesis," *Metabolomics* 1:149-158, Springer Science + Business Media, Inc., United Kingdom (Apr. 2005).
Walecki, J., et al., "Role of short TE H-MR spectroscopy in monitoring of post-operation irradiated patients," *Eur. J. Radiol.* 30:154-161, Thieme, Germany (1999).
Wang, J., et al., "Kynurenic Acid as a Ligand for Orphan G Protein-coupled Receptor $GPR_{35}$*," *J. Biol. Chem.* 281:22021-22028, The American Society of Biochemistry and Molecular Biology, Inc., United States (2006).
Want, E., et al., "The Expanding Role of Mass Spectrometry in Metabolite Profiling and Characterization," *Chem. Bio. Chem.* 6:1941-1951, Wiley-VCH Verlag GmbH & Co. KGaA, Germany (2005).
Weckwerth, W. and Morgenthal, K., "Metabolomics: from pattern recognition to biological interpretation," *Drug Discovery Today* 10:1551-1558, Elsevier Ltd., Netherlands (2005).
Williams, G., et al.. "Fetal valproate syndrome and autism: additional evidence of an association," *Dev. Med. Child Neurol.* 43:202-206, National Spastics Society Medical Education, United Kingdom (2001).
Wu, J. and McAllister, A., "Exact mass measurement on an electrospray ionization time-of-flight mass spectrometer: error distribution and selective averaging," *J. Mass Spectrom.* 38:1043-1053, Wiley, United Kingdom (2003).
Wyszynski, D., et al., "Increased rate of major malformations in offspring exposed to valproate during pregnancy," *Neurology* 64:961-965, Lippincott Williams & Wilkins, United States (2005).
Yan, Y., et al., "Directed Differentiation of Dopaminergic Neuronal Subtypes from Human Embryonic Stem Cells," *Stem Cells* 23:781-790, AlphaMed Press, United States (2005).
Yanes, O., et al., "Metabolic oxidation regulates embryonic stem cell differentiation," *Nat. Chem. Biol.* 6:411-417, Nature Publishing Group, United Kingdom (2010).

(56) References Cited

OTHER PUBLICATIONS

Yang, D., et al., "Assay of the human liver citric acid cycle probe phenylacetylglutamine and of phenylacetate in plasma by gas chromatography-mass spectrometry," *Anal. Biochem.* Academic Press, United States (2003).

Ye, W., et al., "FGF and Shh Signals Control Dopaminergic and Serotonergic Cell Fate in the Anterior Neural Plate," *Cell* 93:755-766, Cell Press, United States (1998).

Yetkin, F. and Mendelsohn, D., "Hypoxia imaging in brain tumors," *Neuroimaging Clin. N. Am.* 12:537-552, W.B. Saunders Company, United States (2002).

Zeng, X., et al., "Dopaminergic Differentiation of Human Embryonic Stem Cells," *Stem Cells* 22:925-940, AlphaMed Press, United States (2004).

Zhang, H., et al., "Mass spectral evidence for carbonate-anion-radical-induced posttranslational modification of tryptophan to kynurenine in human Cu, Zn superoxide dismutase," *Free Radic. Biol. Med.* 37:2018-2026, Elsevier Science, United States (2004).

Zhao, W., et al., "Neural Tube Defects and Maternal Biomarkers of Folate, Homocysteine, and Glutathione Metabolism," *Birth Defects Res. A. Clin. Mol. Teratol.* 76:230-236, John Wiley & Sons, United States (2006).

International Search Report for International Appl. No. PCT/US11/29471, dated Jun. 21, 2011, ISA/US, Alexandria, Virginia, United States.

Written Opinion of the International Searching Authority for International Appl. No. PCT/US11/29471, dated Jun. 21, 2011, ISA/US, Alexandria, Virginia, United States.

Communication for European Patent No. 07 755 255.2, dated Jan. 24, 2011, 5 pages.

United Kingdom Examination Report under Section 18(3) for Application No. GB 0 820 454.7, UK Intellectual Property Office, United Kingdom, 4 pages.

Decision for Swedish Patent Application No. 0850071-2, dated Mar. 5, 2010, Swedish Patent and Registration Office (PRV), Sweden, 5 pages.

English language translation of Decision for Swedish Patent Application No. 0850071-2, dated Mar. 5, 2010, Swedish Patent and Registration Office (PRV), Sweden, 6 pages.

Communication for European Patent No. 08 725 106.2, dated Jun. 28, 2010, European Patent Office, Germany, 5 pages.

Kleinstreuer et al., "Indentifying Developmental Toxcity Pathways for a Subset of ToxCast Chemicals Using Human Embryonic Stem Cells and Metabolomics", *Toxicol. Appl. Pharmacol.*, Nov. 15, 2011; 257(1):111-21, Epub Sep. 3, 2011.

West et al., "Predicting Human Developmental Toxicity of Pharmaceuticals Using Human Embryonic Stem Cells and Metabolomics", *Toxicol. Appl. Pharmacol.*, Aug. 15, 2010; 247(1):18-27, Epub May 21, 2010.

Vrana et al., "Nonhuman Primate Parthenogentic Stem Cells", *Colloquium*, Sep. 30, 2003, vol. 100, Supp. 1, 11911-11916.

Extended European Search Report dated Aug. 6, 2013 in Europe, Patent Application No. 11760090.8-1408, filed Mar. 22, 2011. English language translation included (12 pages).

Tiboni et al., "Production of Axial Skeletal Malformations with the Nitric Oxide Synthesis Inhibitor NG-Nitro-Arginine Methyl Ester (L-NAME) in the Mouse", *Birth Defects Research Part B: Developmental and Reproductive Toxicology*, vol. 80, No. IS.1, Feb. 2007, pp. 28-33.

West et al., "A High Throughout Metabolite-Based Biomarker Approach to Predict Developmental Toxicity Using Human Embryonic Stem Cells", *International Journal of Toxicology*, vol. 32, No. 1, Jan. 2013, p. 70.

Office Action issued in Japan for Application No. 2015-184398 dated Jul. 19, 2016 (7 pages).

\* cited by examiner

PREDICTING HUMAN DEVELOPMENTAL TOXICITY OF PHARMACEUTICALS USING HUMAN STEM-LIKE CELLS AND METABOLOMICS

CROSS REFERENCE TO RELATED APPLICATIONS

This application is a continuation application of U.S. application Ser. No. 13/069,326, filed Mar. 22, 2011, which claims the benefit of U.S. Ser. No. 61/316,165, filed Mar. 22, 2010 and U.S. Ser. No. 61/394,426, filed Oct. 19, 2010, the entire contents of which are incorporated herein by reference.

BACKGROUND OF THE INVENTION

Field of the Invention

This invention provides methods for toxicological screening of pharmaceuticals and other chemical compounds. The invention specifically provides assays that involve multipotent human stem-like cells (hSLCs), as well as methods for using these cells to detect developmental toxicity or teratogenic effects of pharmaceutical compounds and other chemicals. More particularly, the invention provides an in vitro means for analyzing toxicity of compounds predictive of their toxicity during human development. Candidate predictive biomarkers for toxic or teratogenic effects are also identified and provided herein.

Background Art

Birth defects are a leading cause of infant morbidity and pediatric disorders in the United States, affecting 1 in every 33 infants born (Brent & Beckman, 1990, Bull NY Acad Med 66: 123-63; Rosano et al., 2000, J. Epidemiology Community Health 54:660-66), or approximately 125,000 newborns per year. It is understood that developmental toxicity can cause birth defects, and can generate embryonic lethality, intrauterine growth restriction (IUGR), dysmorphogenesis (such as skeletal malformations), and functional toxicity, which can lead to cognitive disorders such as autism. There is an increasing concern about the role that chemical exposure can play in the onset of these disorders. Indeed, it is estimated that 5% to 10% of all birth defects are caused by in utero exposure to known teratogenic agents which induce developmental abnormalities in the fetus (Beckman & Brent, 1984, Annu Rev Pharmacol 24: 483-500).

Concern exists that chemical exposure may be playing a significant and preventable role in producing birth defects (Claudio et al., 2001, Environm Health Perspect 109: A254-A261). This concern has been difficult to evaluate, however, since the art has lacked a robust and efficient model for testing developmental toxicity for the more than 80,000 chemicals in the market, plus the new 2,000 compounds introduced annually (General Accounting Office (GAO), 1994, Toxic Substances Control Act: Preliminary Observations on Legislative Changes to Make TSCA More Effective, Testimony, Jul. 13, 1994, GAO/T-RCED-94-263). Fewer than 5% of these compounds have been tested for reproductive outcomes and even fewer for developmental toxicity (Environmental Protective Agency (EPA), 1998, Chemical Hazard Data Availability Study, Office of Pollution Prevention and Toxins). Although some attempts have been made to use animal model systems to assess toxicity (Piersma, 2004, Toxicology Letters 149:147-53), inherent differences in the sensitivity of humans in utero have limited the predictive usefulness of such models. Development of a human-based cell model system would have an enormous impact in drug development and risk assessment of chemicals.

Toxicity, particularly developmental toxicity, is also a major obstacle in the progression of compounds through the drug development process. Currently, toxicity testing is conducted on animal models as a means to predict adverse effects of compound exposure, particularly on development and organogenesis in human embryos and fetuses. The most prevalent models that contribute to FDA approval of investigational new drugs are whole animal studies in rabbits and rats (Piersma, 2004, Toxicology Letters 149: 147-53). In vivo studies rely on administration of compounds to pregnant animals at different stages of pregnancy and embryonic/fetal development (first week of gestation, organogenesis stage and full gestation length). However, these in vivo animal models are limited by a lack of biological correlation between animal and human responses to chemical compounds during development due to differences in biochemical pathways. Species differences are often manifested in trends such as dose sensitivity and pharmacokinetic processing of compounds. According to the reported literature, animal models are approximately 60% efficient in predicting human developmental response to compounds (Greaves et al., 2004, Nat Rev Drug Discov 3:226-36). Thus, human-directed predictive in vitro models present an opportunity to reduce the costs of new drug development and enable safer drugs.

In vitro models have been employed in the drug industry for over 20 years (Huuskonen, 2005, Toxicology & Applied Pharm 207:S495-S500). Many of the current in vitro assays involve differentiation models using primary cell cultures or immortalized cells lines (Huuskonen, 2005, Toxicology & Applied Pharm 207:S495-S500). Unfortunately, these models differ significantly from their in vivo counterparts in their ability to accurately assess development toxicity. In particular, the ECVAM initiative (European Center for Validation of Alternative Methods) has used mouse embryonic stem cells as a screening system for predictive developmental toxicology. The embryonic stem cell test (EST) has been able to predict the teratogenicity of 78% of the drugs tested, and the test was reported to be able to differentiate strong teratogens from moderate/weak or non-embryotoxic compounds (Spielmann et al., 1997, In vitro Toxicology 10:119-27). This model is limited in part because toxicological endpoints are defined only for compounds that impair cardiac differentiation. This model also fails to account for interspecies developmental differences between mice and humans, and so does not fully address the need in the art for human-specific model systems.

Thus there remains a need in the art for a human cell derived in vitro method for reliably determining developmental toxicity in pharmaceutical agents and other chemical compounds. There also is a need in the art to better understand human development and its perturbation by toxins and other developmental disrupting agents, to assist clinical management of acquired congenital disorders and the many diseases that share these biochemical pathways, such as cancer. Human derived cell based systems increase the probability of identifying biomarkers of toxicity that may both predict toxicity as well as identify toxicity caused by other diseases.

The association of metabolomics and human embryonic stem cells (hESCs) has led to a more effective in vitro human model to predict developmental toxicity. hESCs were first derived from the inner cell mass of blastocysts (Thomson et al. 1998). Given the human embryonic origin of these cells, an in vitro teratogenicity test using hESCs is likely to produce more accurate human endpoints, while at the same time reducing cost and time and increasing predictability over animal studies. Metabolomics assesses functional changes in biochemical pathways by detecting changes to the dynamic set of small molecules that comprise the metabolome. The feasibility of metabolomics in biomarker discovery has been demonstrated by multiple studies (Cezar et al. 2007, Tan et al. 1998, Sabatine et al. 2005, Barr et al. 2003, Qu et al. 2000).

However, there is an unmet need to develop more accurate methods for human developmental toxicity screening and the establishment of a highly predictive in vitro system for predicting chemical toxicity during early human development.

The present study discloses the establishment of such a system. The present invention further provides for the assessment of a plurality of small molecules, preferably secreted or excreted from human stem-like cells (hSLCs), and is determined and correlated with health and disease or insult state.

The present invention provides a high-throughput developmental toxicity screen that is more predictive than currently available assays and which offers quantitative human endpoints.

BRIEF SUMMARY OF THE INVENTION

The present invention provides reagents and methods for more reliable in vitro screening of toxicity and teratogenicity of pharmaceutical and non-pharmaceutical chemicals on hSLCs.

The invention provides human-specific in vitro methods for reliably determining toxicity, particularly developmental toxicity and teratogenicity of pharmaceuticals and other chemical compounds using hSLCs. As provided herein, hSLCs are useful for assessing toxic effects of chemical compounds, particularly said toxic and teratogenic effects on human development, thus overcoming the limitations associated with interspecies animal models.

In particular, the invention demonstrates that metabolite profiles of hSLCs are altered in response to known disruptors of human development. The invention further shows that the hSLC metabolome is a source of human biomarkers for disease and toxic response.

Thus, the hSLC and metabolomics based model of the present invention offers a significant advantage over other studies that use mouse or zebra fish-based models to determine toxicity and teratogenicity of chemical compounds in that the present invention utilizes an all human system and human biomarkers to understand the mechanisms of human developmental toxicity.

In one embodiment, the invention discloses a method of predicting teratogenicity of a test compound, comprising the steps of:
  a) culturing hSLCs:
    i) in the presence of a first known teratogenic compound; and
    ii) in the absence of the first known teratogenic compound;
  b) detecting a plurality of metabolites having a molecular weight of less than about 3000 Daltons associated with hSLCs exposed to the first known teratogenic compound in comparison with hSLCs not exposed to the first known teratogenic compound in order to identify a difference in metabolic response of hSLCs exposed to the first known teratogenic compound in comparison with hSLCs not exposed to the first known teratogenic compound;
  c) analyzing the difference in metabolic response in order to generate a set of mass features associated with exposure of hSLCs to the first teratogenic compound;
  d) repeating steps a)-c) multiple times, each time with a different known teratogenic compound;
  e) grouping mass features generated from each exposure to a teratogenic compound to obtain a first reference profile of mass features;
  f) comparing a profile of mass features generated upon exposure of hSLCs to a test compound with the first reference profile to predict the teratogenicity of the test compound;
  g) if the test compound is predicted to be a teratogen, adding the profile of mass features to the first reference profile to obtain a second reference profile, wherein the predictive accuracy of the second reference profile is greater than the predictive accuracy of the first reference profile; and
  h) repeating steps f) and g) multiple times, each time with a different test compound to obtain a final reference profile.

In another embodiment, the invention discloses a method for classifying a test compound as a teratogen, the method comprising the steps of:
  a) culturing hSLCs:
    i) in the presence of the test compound; and
    ii) in the absence of the test compound;
  b) identifying a difference in metabolic response of hSLCs in the presence of the test compound in comparison with hSLCs cultured in the absence of the test compound by measuring a plurality of metabolites having a molecular weight of less than about 3000 Daltons associated with hSLCs, wherein a difference in the plurality of metabolites associated with hSLCs cultured in the presence of the test compound versus hSLCs cultured in the absence of the test compound indicates a difference in metabolic response; and
  c) determining the metabolic response of hSLCs involving a first metabolite to the metabolic response of hSLCs involving a second metabolite, wherein
    i) the first metabolite is a precursor of the second metabolite; or
    ii) the first metabolite is an amino acid and the second metabolite is an inhibitor of the metabolism of the amino acid,
  and wherein a difference in the metabolic response of hSLCs involving the first metabolite to the metabolic response of hSLCs involving the second metabolite is indicative of the test compound being a teratogen.

In yet another embodiment, the invention discloses a method of classifying a test compound as a teratogen or a non-teratogen, comprising the steps of:
  a) culturing hSLCs:
    i) in the presence of the test compound; and
    ii) in the absence of the test compound;
  b) determining the fold change in arginine associated with hSLCs cultured in the presence of the test compound in comparison with hSLCs cultured in the absence of the test compound;
  c) determining the fold change in asymmetric dimethyl arginine (ADMA) associated with hSLCs cultured in the presence of the test compound in comparison with hSLCs cultured in the absence of the test compound;

d) determining the ratio of the fold change in arginine to the fold change in ADMA, wherein:
   i) a ratio of less than at least about 0.9 or greater than at least about 1.1 is indicative of the teratogenicity of the test compound; and
   ii) a ratio of greater than at least about 0.9 and less than at least about 1.1 is indicative of the non-teratogenicity of the test compound.

In a further embodiment, the invention discloses a method for validating a test compound as a teratogen, comprising:
a) providing, in solid form, a set of metabolites having a molecular weight of less than about 3000 Daltons, wherein the metabolites are differentially metabolized by hSLCs cultured in the presence of one or more known teratogenic compounds in comparison with hSLCs cultured in the absence of a teratogenic compound;
b) resuspending the set of metabolites in a predetermined volume of a physiologically suitable buffer, wherein the final concentration of each metabolite in the buffer is identical to the concentration of that metabolite associated with hSLCs cultured in the presence of one or more known teratogenic compounds;
c) generating a reference profile of the metabolites; and
d) comparing a profile of mass features generated upon exposure of hSLCs to the test compound with the reference profile of metabolites in order to validate the teratogenicity of the test compound.

In yet another embodiment, the invention discloses a method of identifying a metabolic effect of a teratogenic compound, comprising:
a) culturing hSLCs:
   i) in the presence of the teratogenic compound; and
   ii) in the absence of the teratogenic compound;
b) detecting a plurality of metabolites having a molecular weight of less than about 3000 Daltons associated with hSLCs exposed to the teratogenic compound in comparison with hSLCs not exposed to the teratogenic compound in order to identify a difference in metabolic response of hSLCs exposed to the teratogenic compound in comparison with hSLCs not exposed to the teratogenic compound;
c) mapping the plurality of metabolites to one or more metabolic networks; and
d) identifying a metabolic effect of the teratogenic compound when the plurality of metabolites are identical to metabolites affected by a known disruption of the one or more metabolic networks.

Specific preferred embodiments of the present invention will become evident from the following more detailed description of certain preferred embodiments and the claims.

BRIEF DESCRIPTION OF THE DRAWINGS/FIGURES

FIG. 1 illustrates the experimental design used in the present study. Three plate replicates with three well replicates were used for controls (cells with undosed media) and experimental cells (dosed cells). Three well replicates were used for media control (no cells, undosed media) and dosed media controls (no cells, dosed media).

FIG. 2 illustrates cell viability data that has been normalized to control, undosed cells.

FIG. 3 shows multidimensional scaling plot of the of Random Forest model (similarity metric) showing a clear separation of drugs based on teratogenicity. The circled drug treatments mark rifampicin and accutane that were misclassified as non-teratogens by the random forest model. Gray=Teratogen, Black=Non-Teratogen, point=first letter of drug.

FIG. 4 illustrates a receiver operating characteristic (ROC) curve based on the 18-feature refined random forest model.

FIG. 5 depicts a specific step of the urea cycle involving metabolism of L-arginine to L-citrulline. NO is released when the enzyme nitric oxide synthase (NOS) oxidizes L-arginine to L-citrulline. Dimethylarginine inhibits nitric oxide synthase. Nitric oxide has been shown to induce Neural Tube Defects (NTD) in rat embryos.

Figure 10:
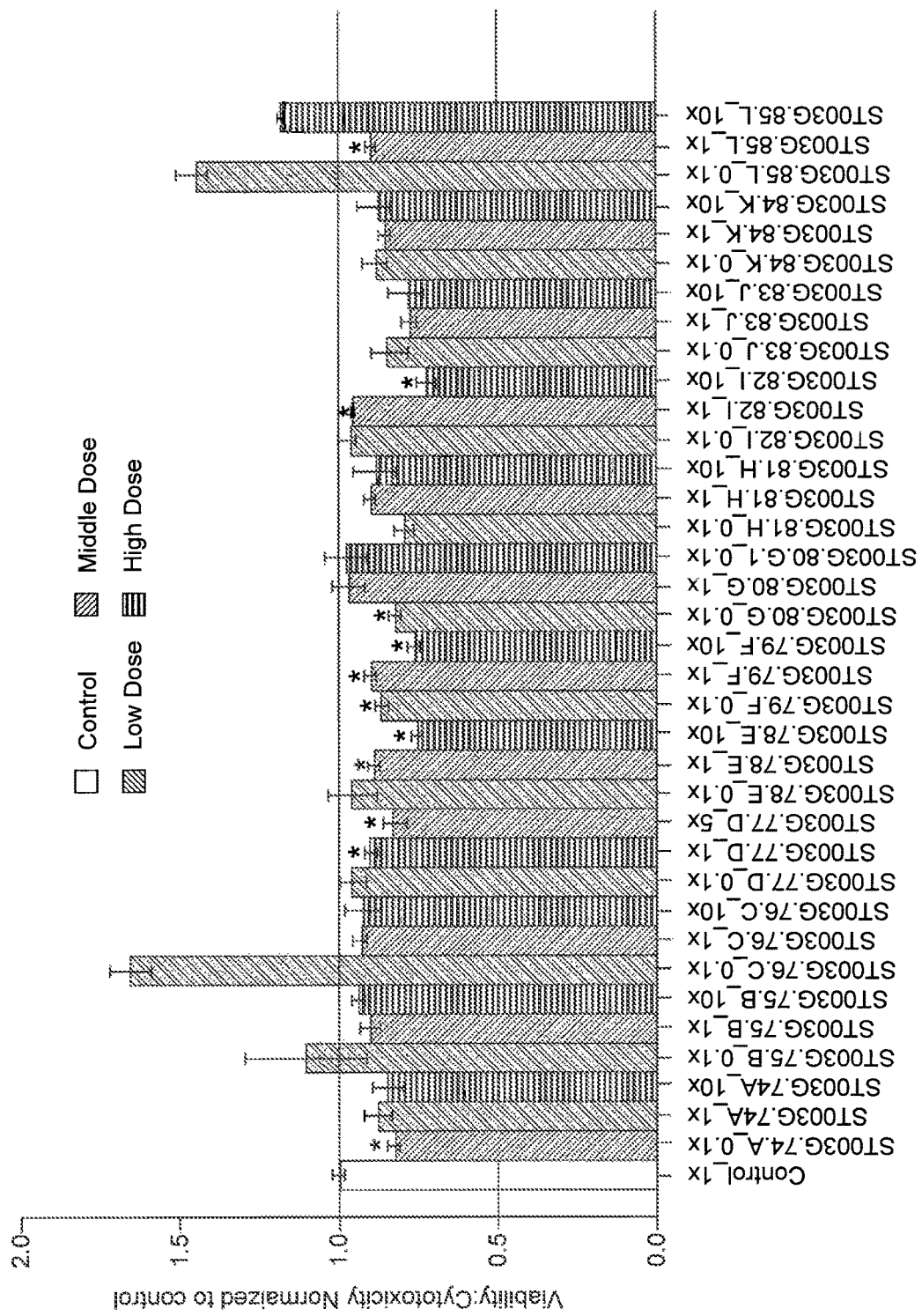

FIG. 10 depicts a viability assay. Cytotoxicity ratios normalized to the untreated cells (controls) present for each 96-well plate. Bars marked with an asterisk indicate a statistically significant decrease (p value<0.05) in viability: cytotoxicity ratios by a Welch T-test. Chemical compound treatments ST003G-74-A, ST003G-80G, and ST0003G-81H exhibit unexpected viability results where low dose appears more toxic than 10×. Drug treatments ST003G-84K, and ST003G-85L do not exhibit a decrease in viability associated with an increase in dosage.

Figure 11:
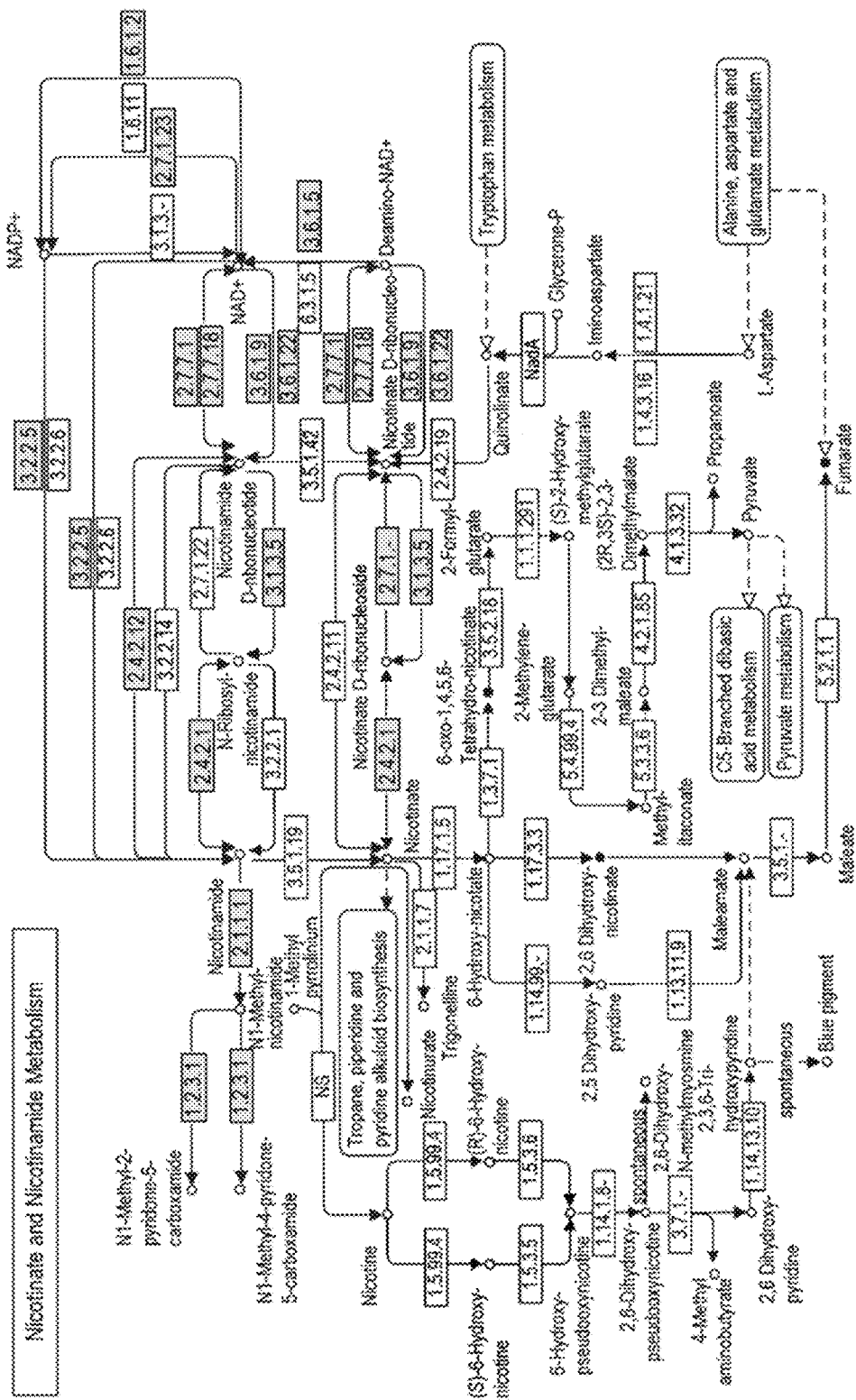

FIG. 11 depicts the nicotinate and nicotinamide metabolic network. In this figure and FIGS. 12-28 that follow, all of the features across all 12 treatment compounds that were putatively annotated with KEGG ID's and identified as significant in the pathways enrichment analysis were reviewed for fold changes and marked with black circles in the pathway diagrams. Isobaric enzymes are marked with grey circles. Enzymes are identified with EC codes and identified human enzyme activity is highlighted in grey.

Figure 12:
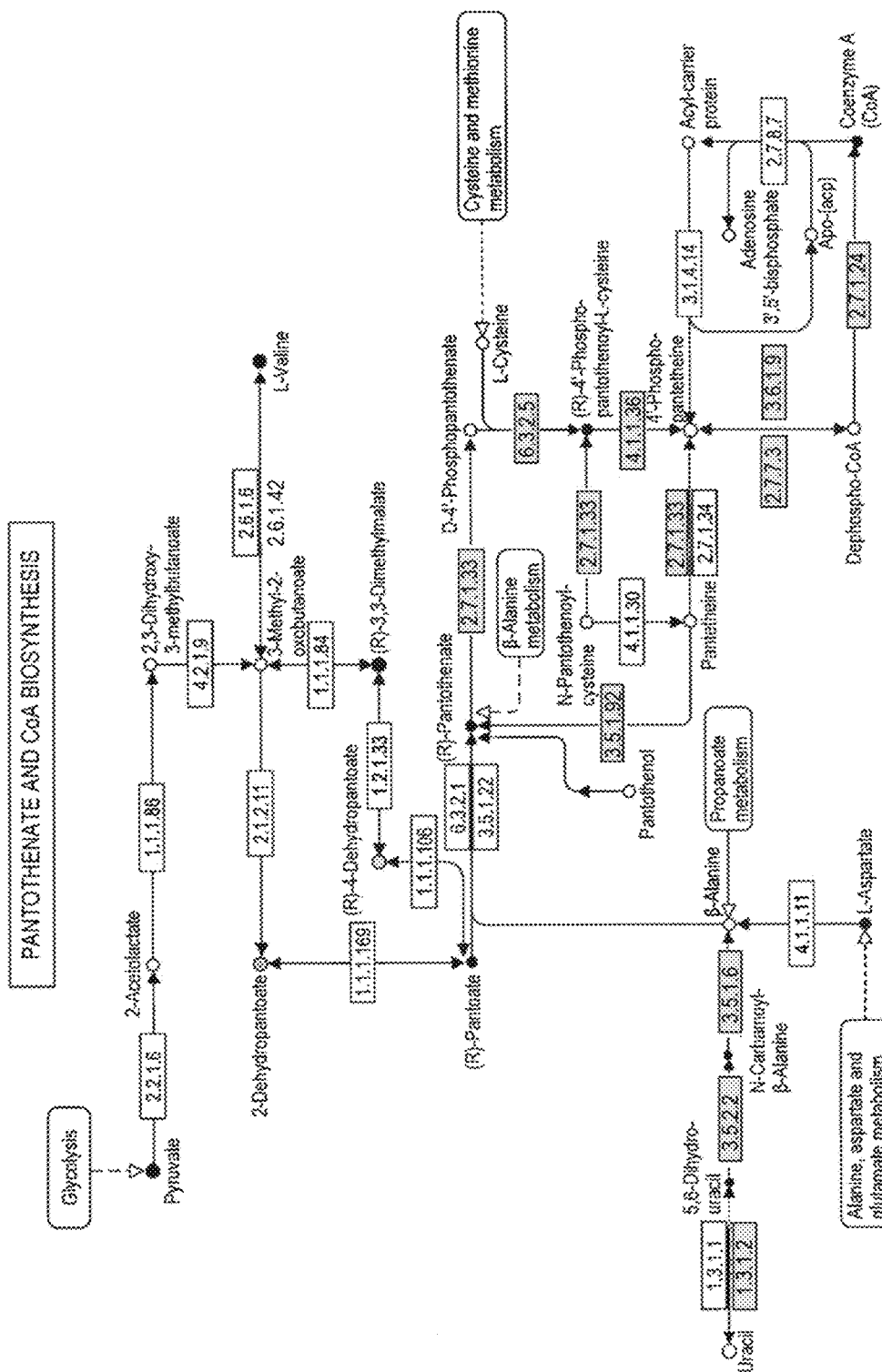

FIG. 12 depicts the pantothenate and coenzyme A biosynthesis pathway, wherein the respective pathways are modified as disclosed herein.

Figure 13:
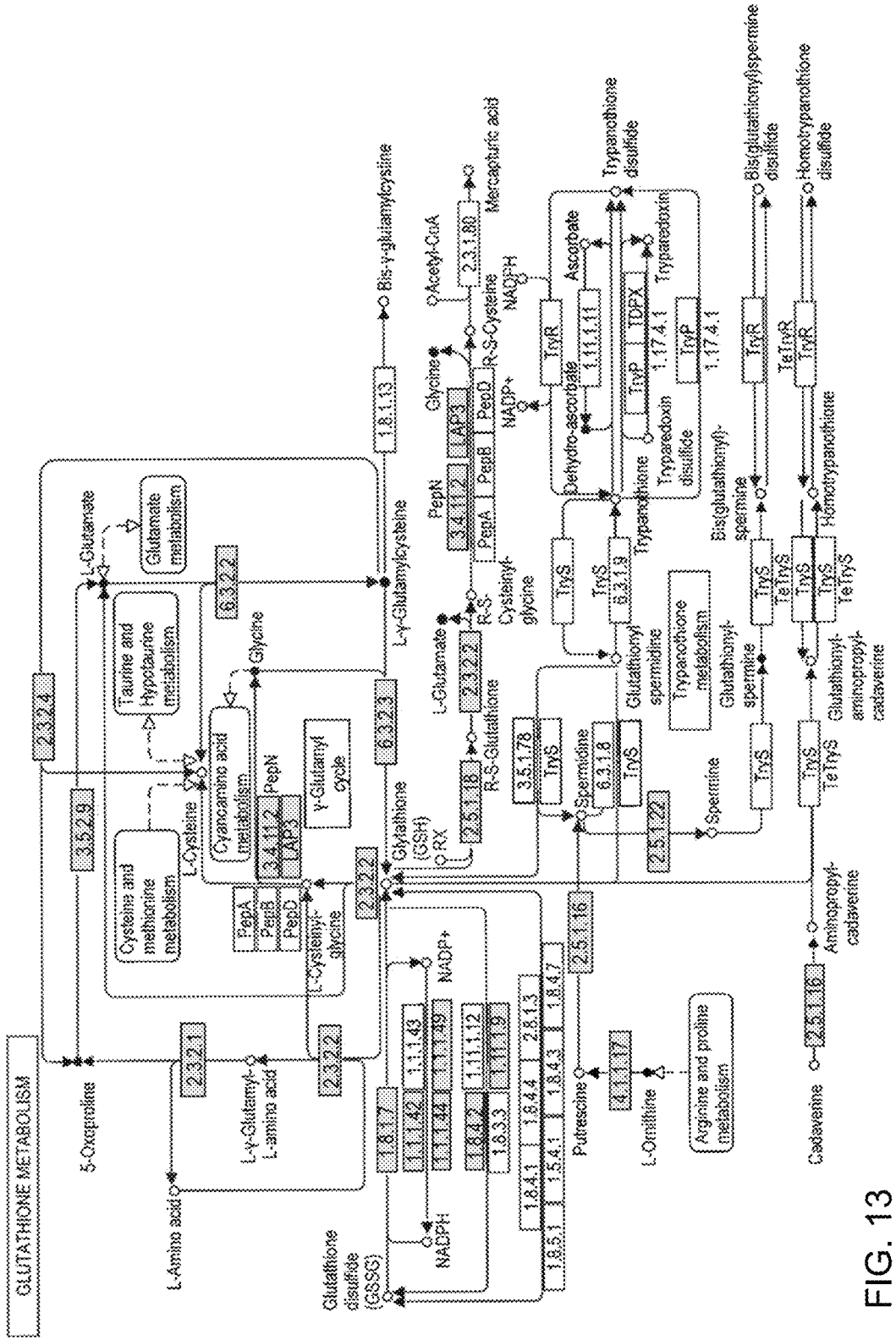

FIG. 13 depicts the glutathione metabolic network, wherein the pathway is modified according to the present disclosure.

Figure 14:
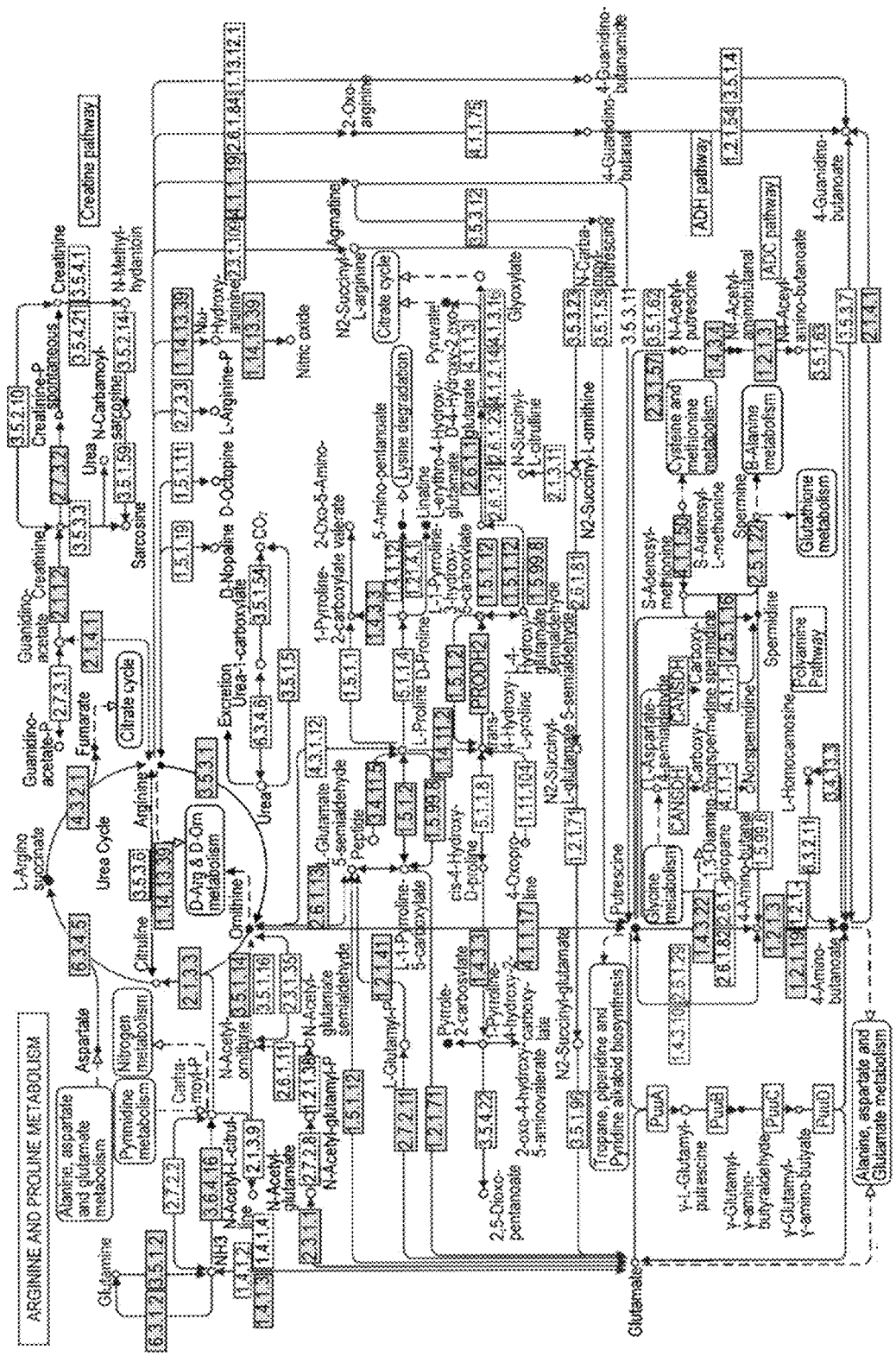

FIG. 14 depicts the arginine and proline metabolic network, wherein the pathway is modified according to the present disclosure.

Figure 15:
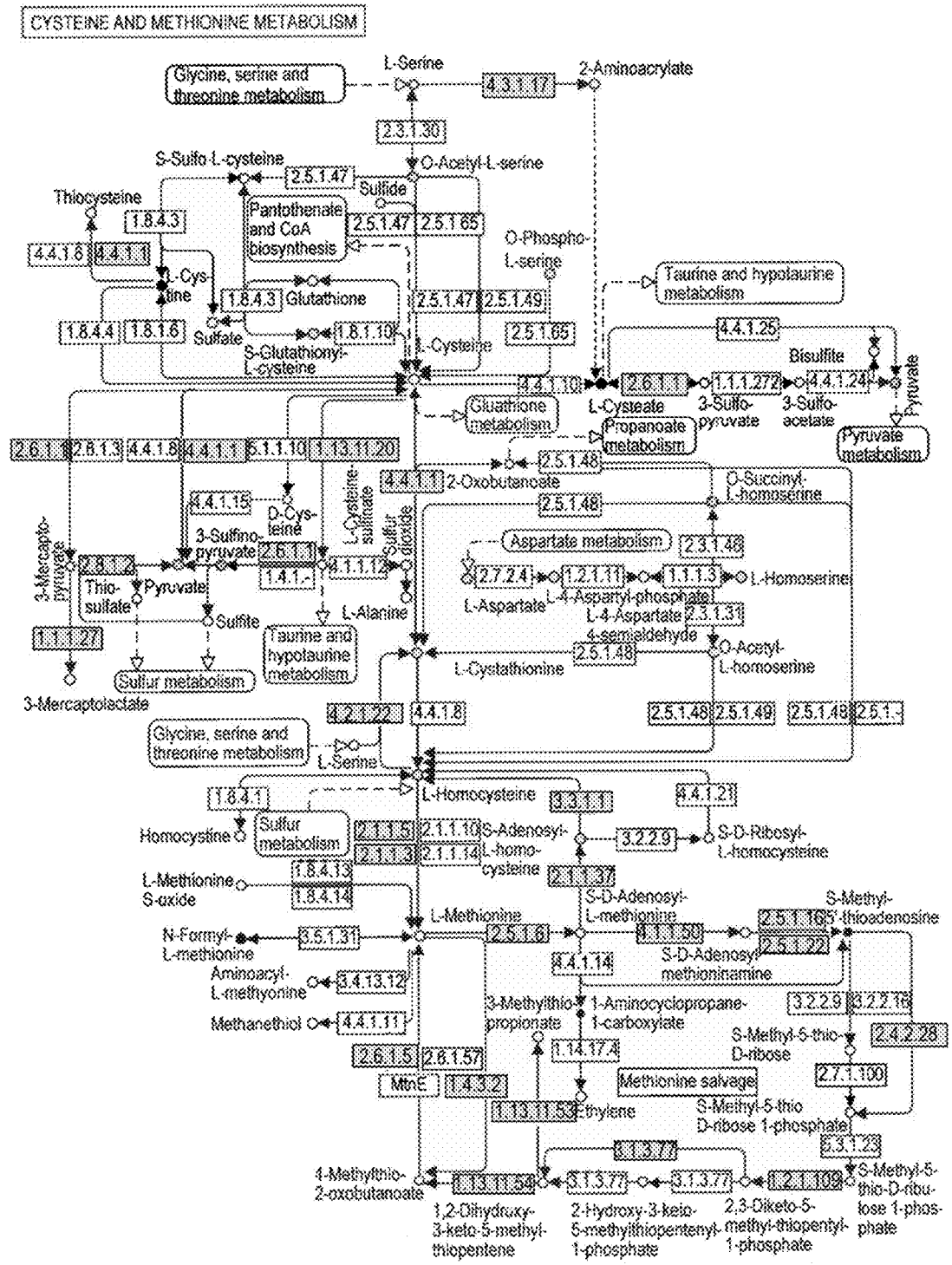

FIG. 15 depicts the cysteine and methionine metabolic network, wherein the pathway is modified according to the present disclosure.

Figure 16:
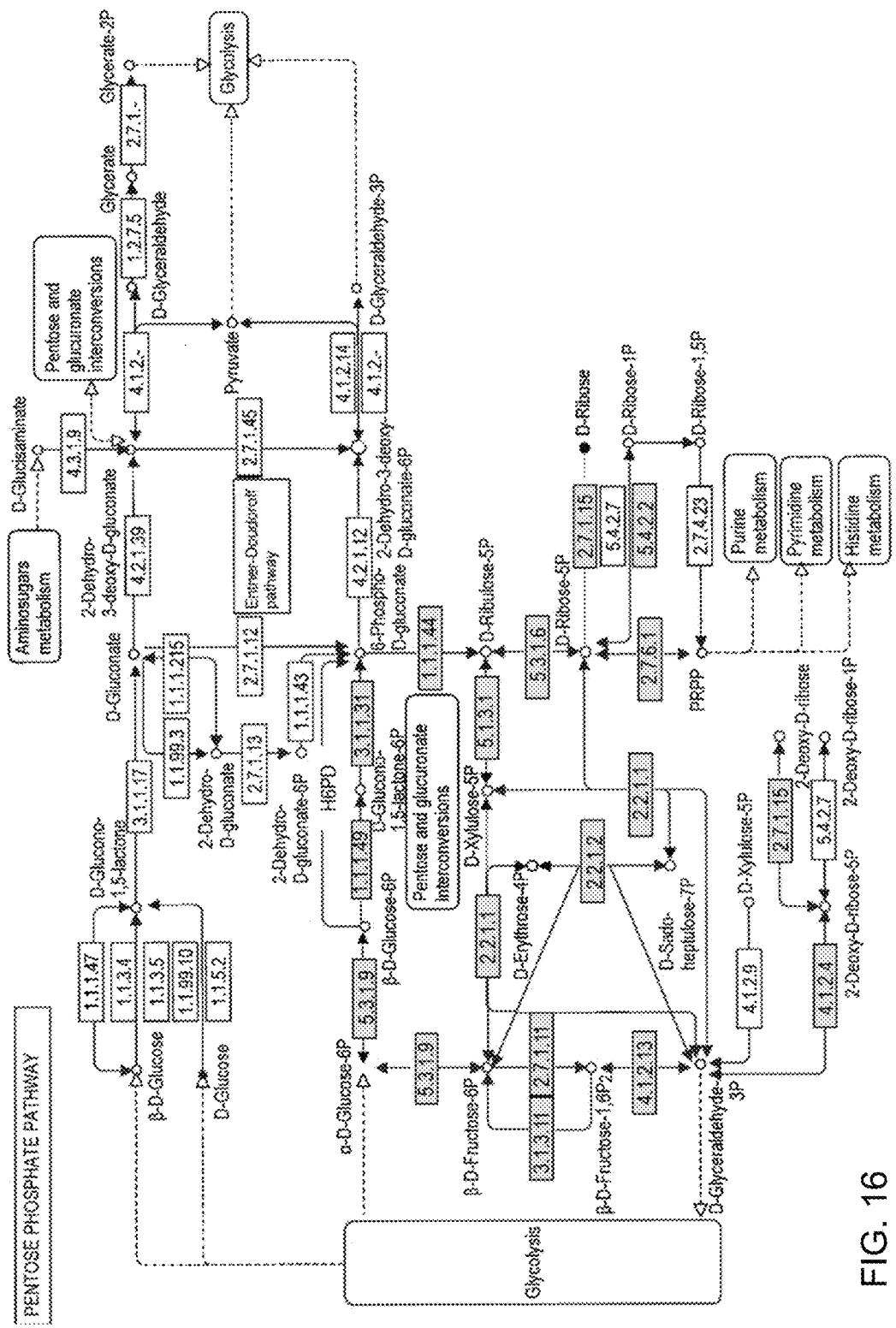

FIG. 16 depicts the pentose phosphate pathway, wherein the pathway is modified according to the present disclosure.

Figure 17:
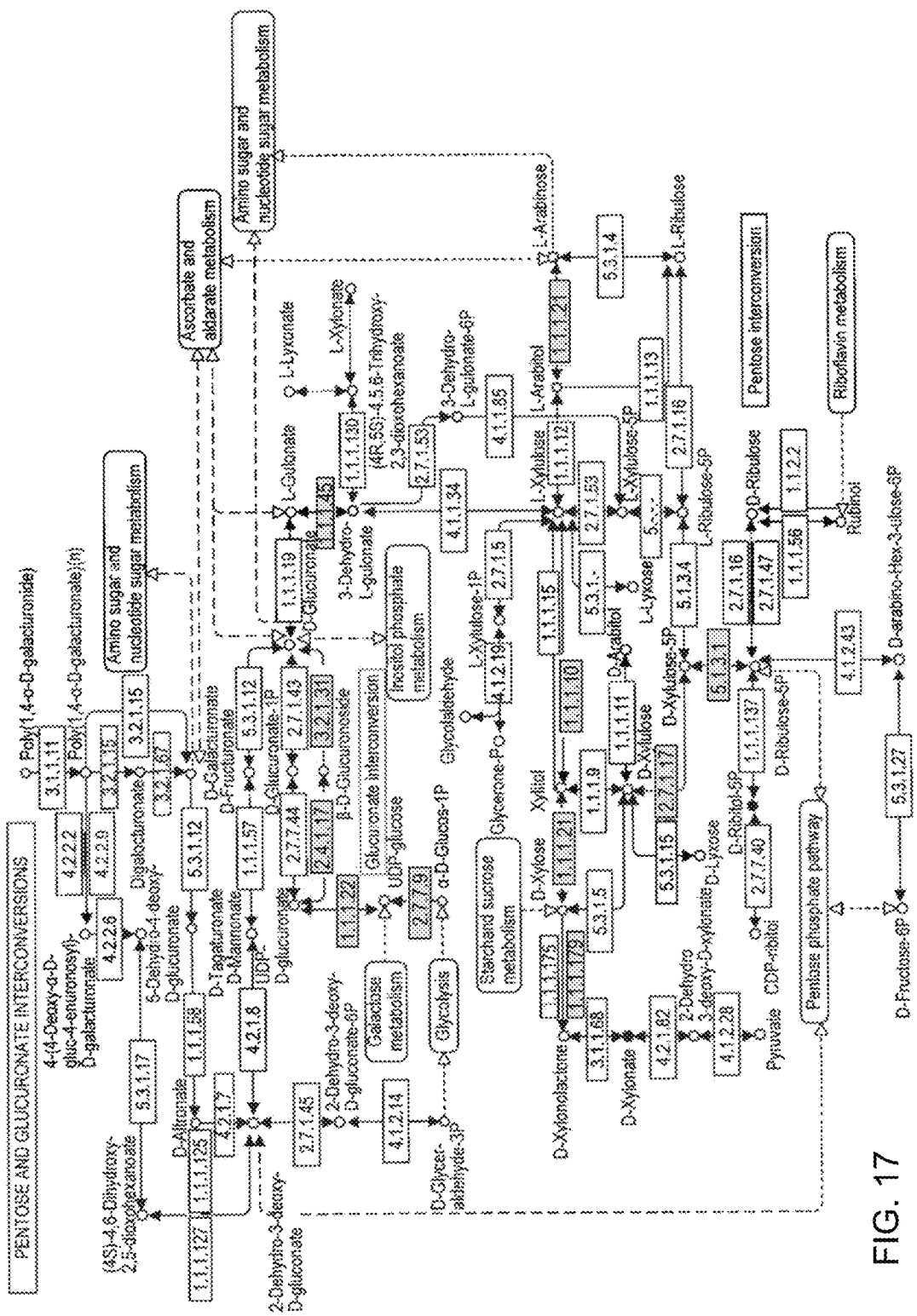

FIG. 17 depicts the pentose and glucoronate interconversions pathway, wherein the pathway is modified according to the present disclosure.

Figure 18:
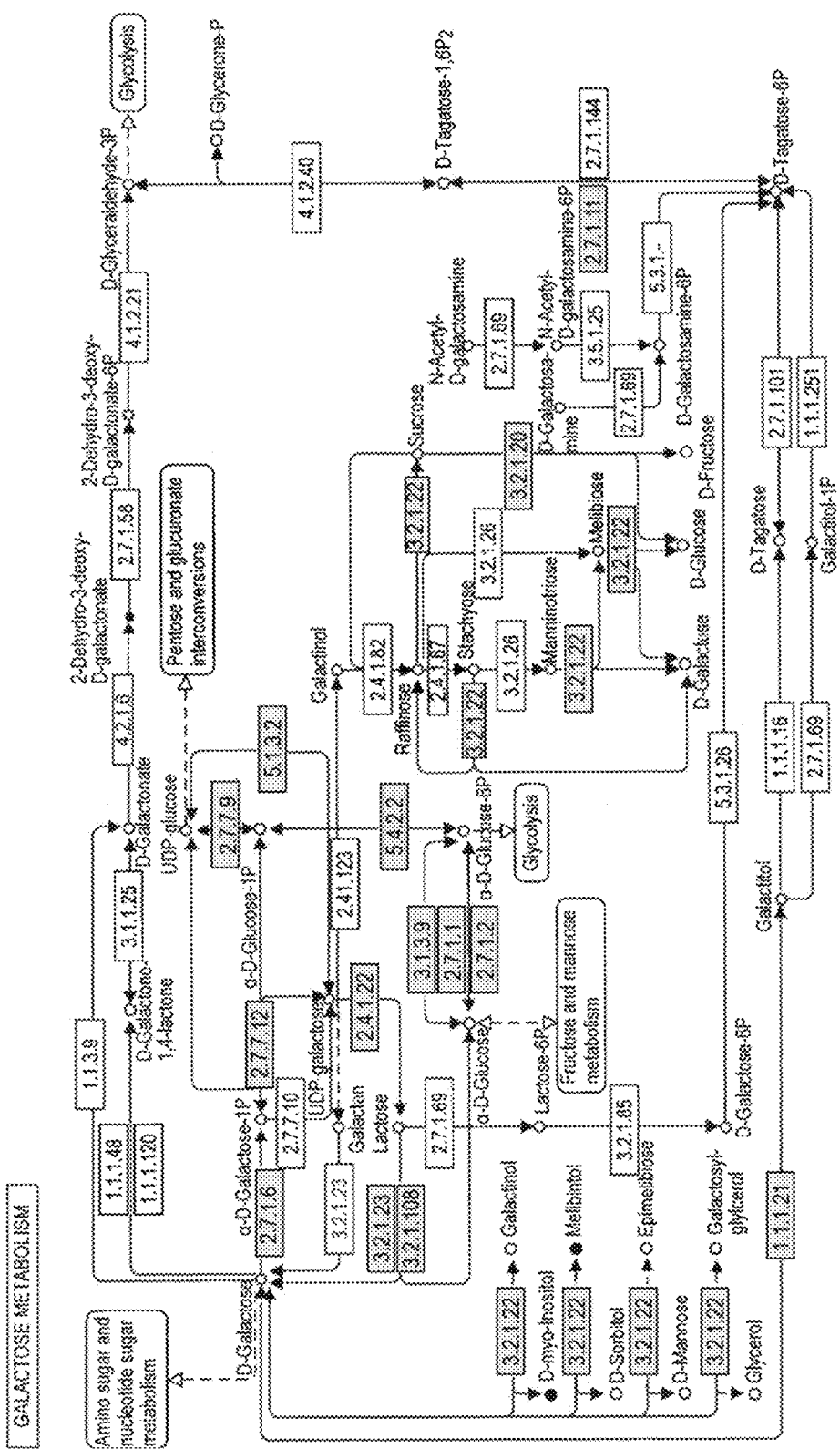

FIG. 18 depicts the galactose metabolic network, wherein the pathway is modified according to the present disclosure.

Figure 19:
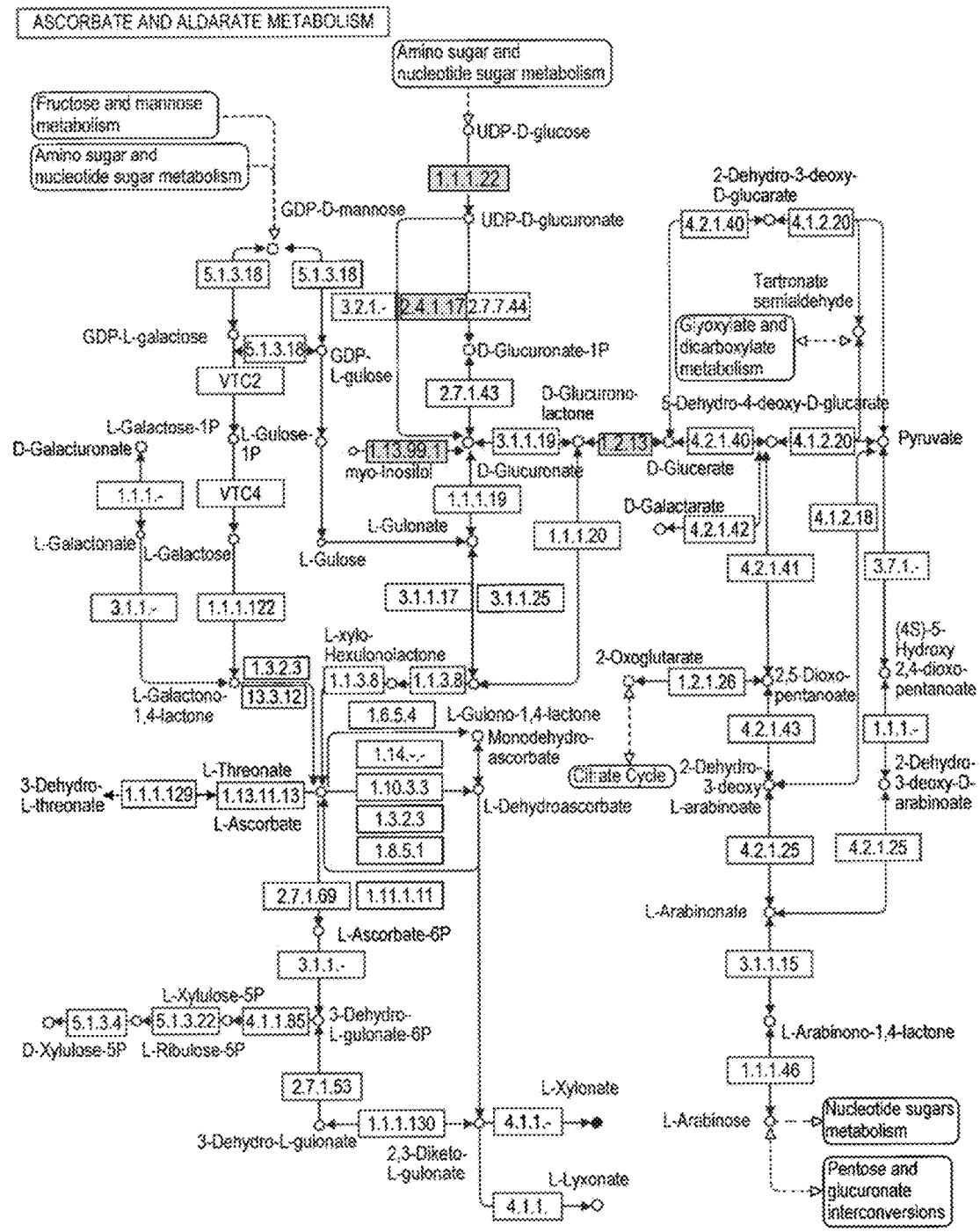

FIG. 19 depicts the ascorbate and aldarate metabolic network, wherein the pathway is modified according to the present disclosure.

Figure 20:
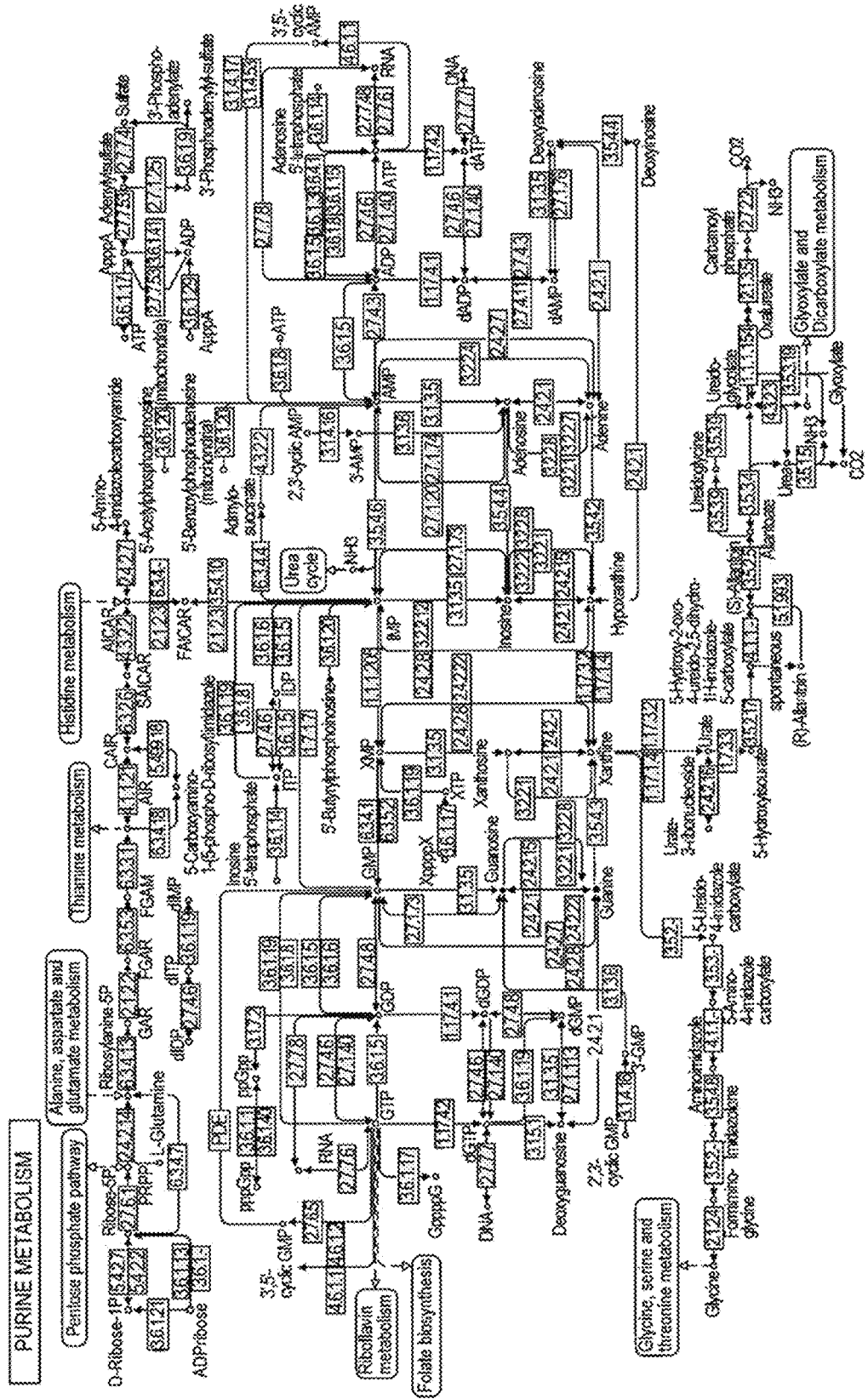
Figure 20:
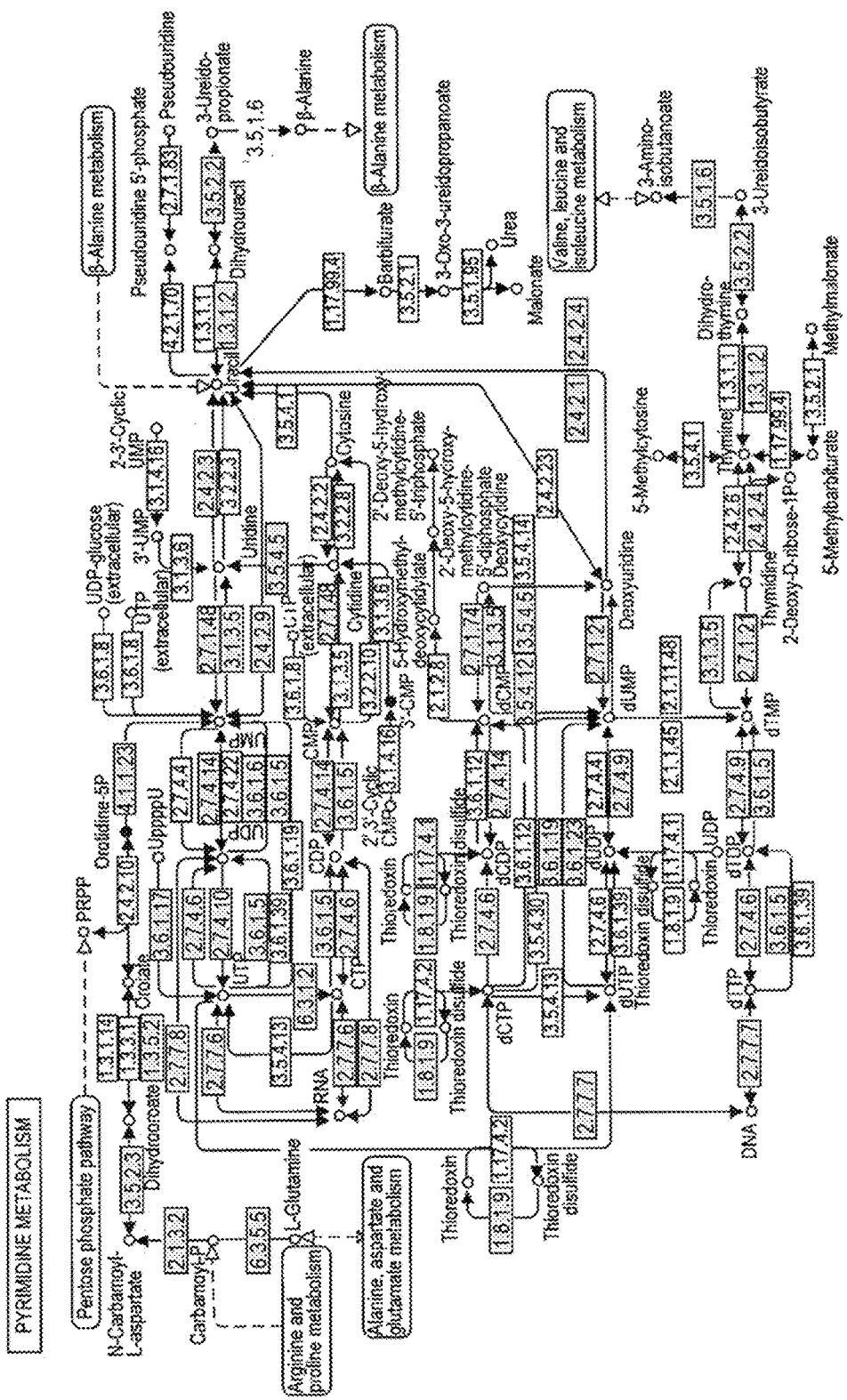

FIG. 20 depicts the purine and pyrimidine metabolic networks, wherein the pathway is modified according to the present disclosure.

Figure 21:
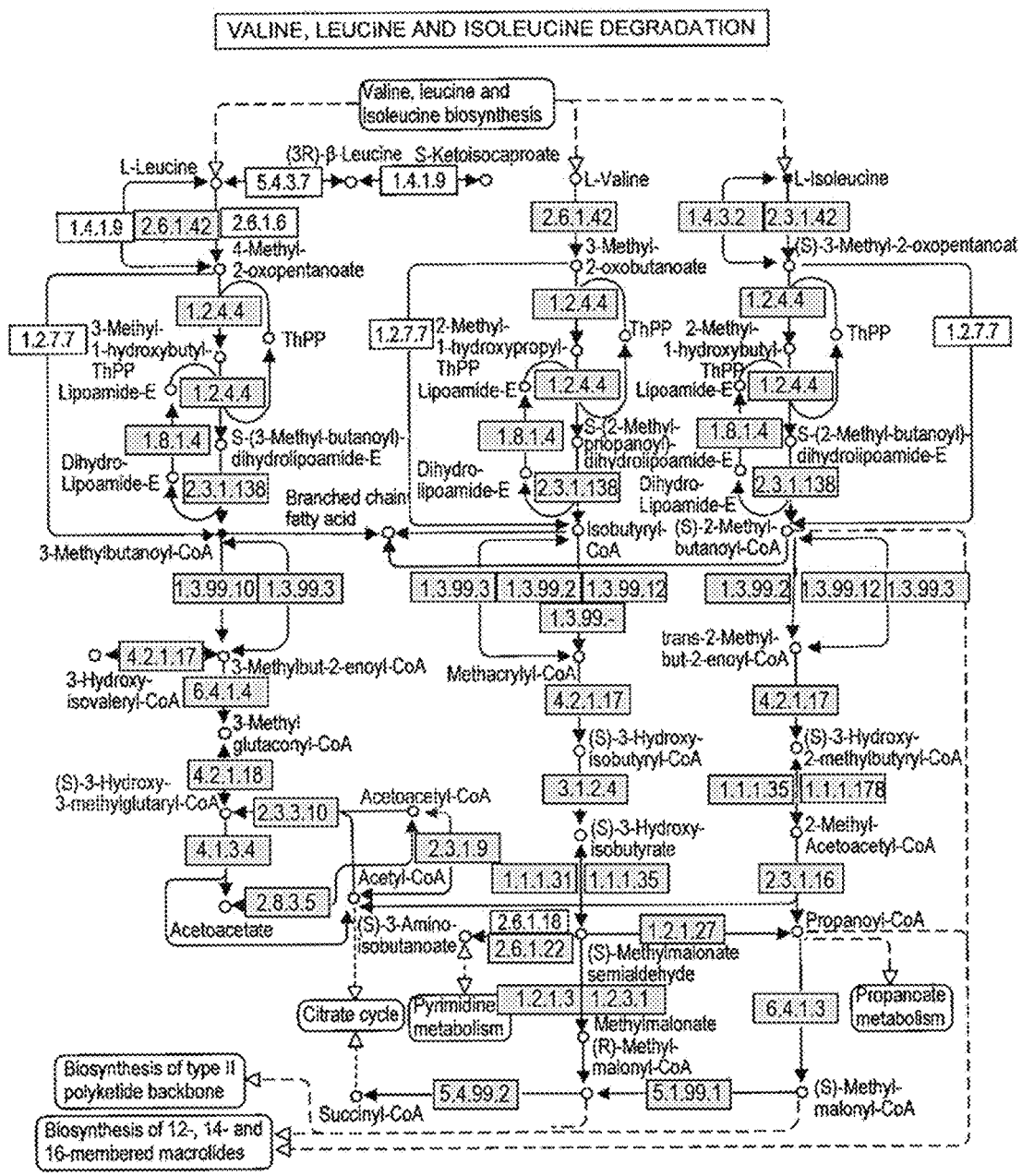

FIG. 21 depicts the valine, leucine, and isoleucine degradation pathway, wherein the pathway is modified according to the present disclosure.

Figure 22:
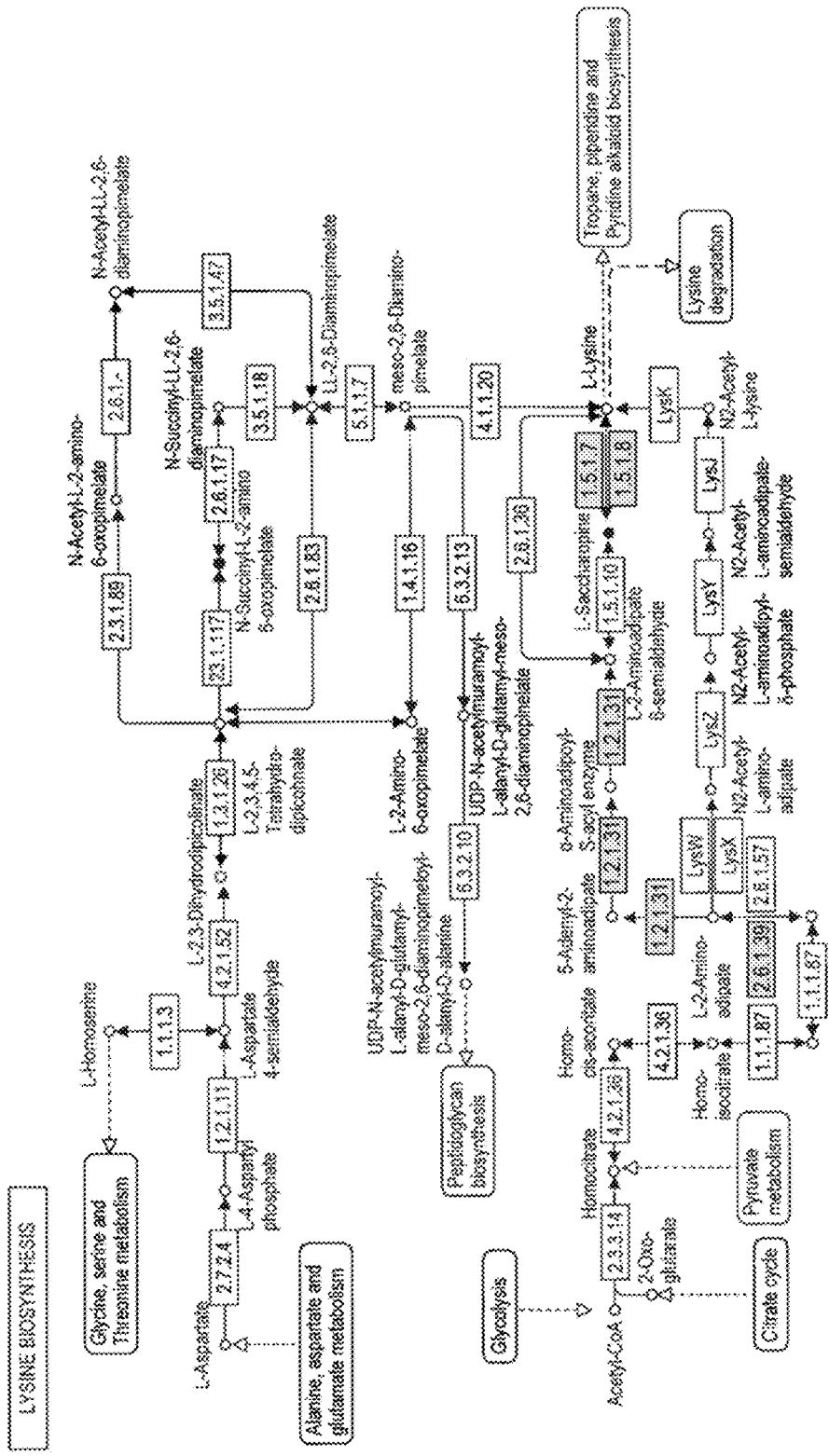
Figure 22:
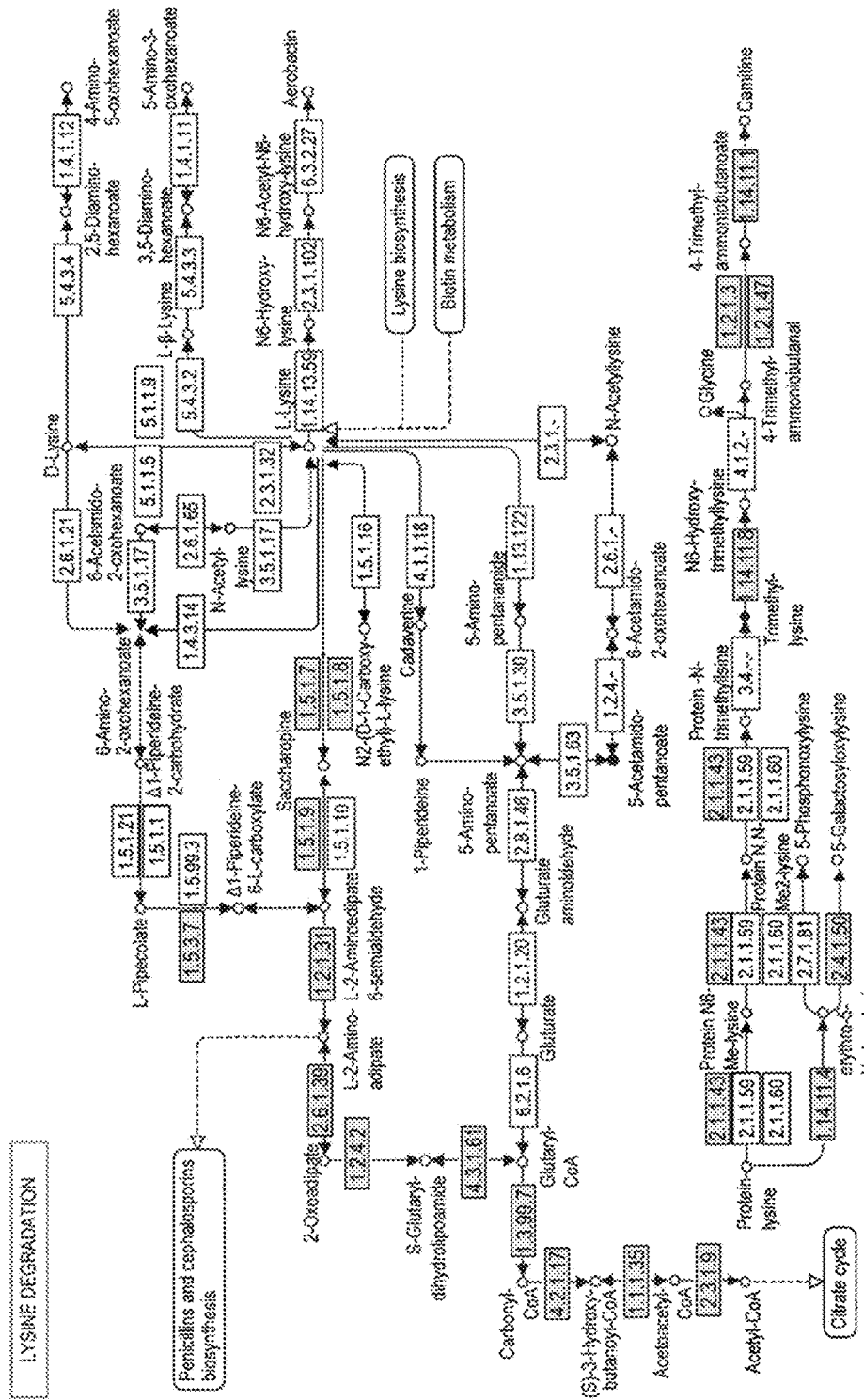

FIG. 22 depicts the lysine biosynthesis and lysine degradation pathways, wherein the pathway is modified according to the present disclosure.

Figure 23:
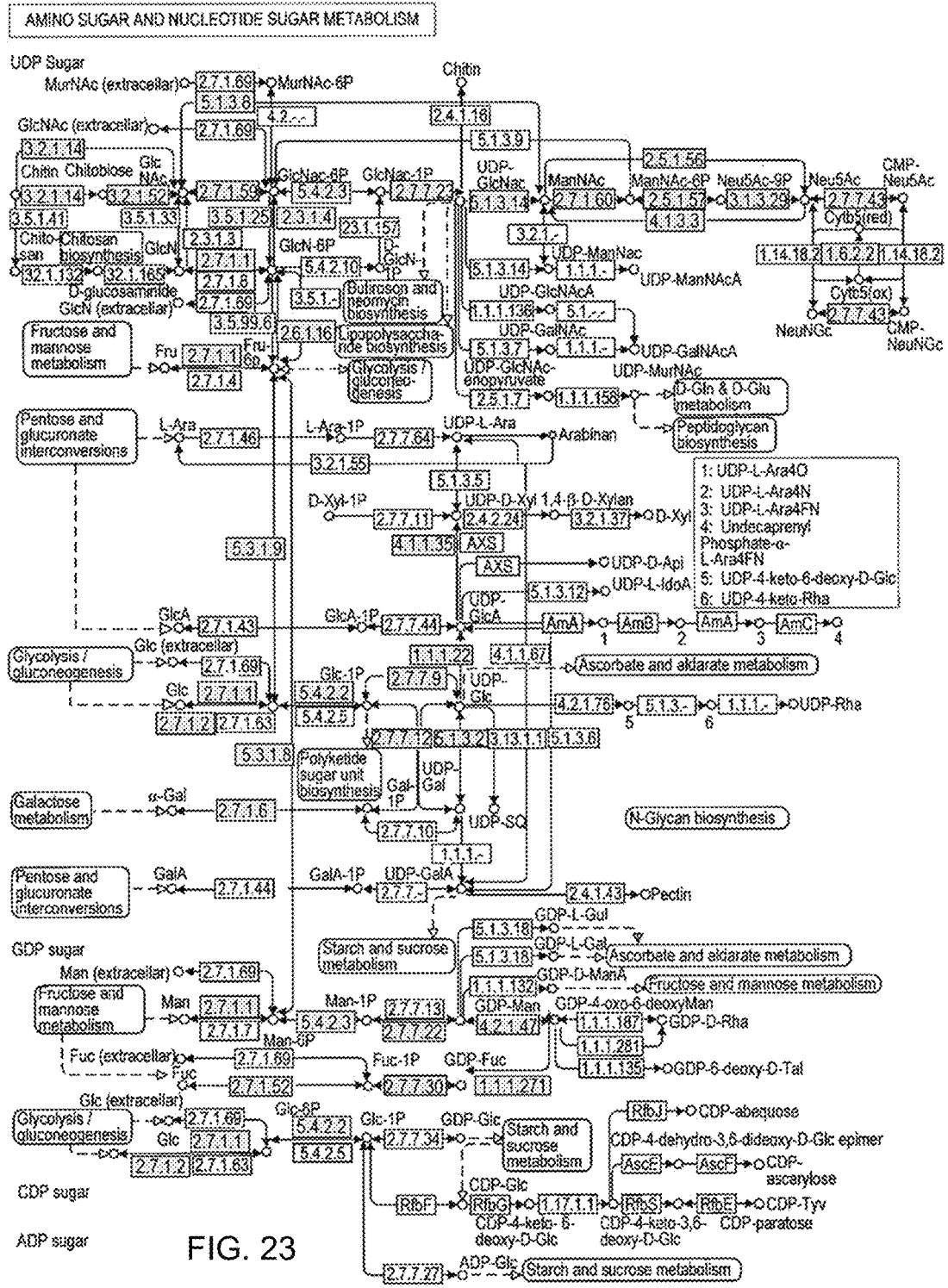

FIG. 23 depicts the amino sugar and nucleotide sugar metabolic network, wherein the pathway is modified according to the present disclosure.

Figure 24:
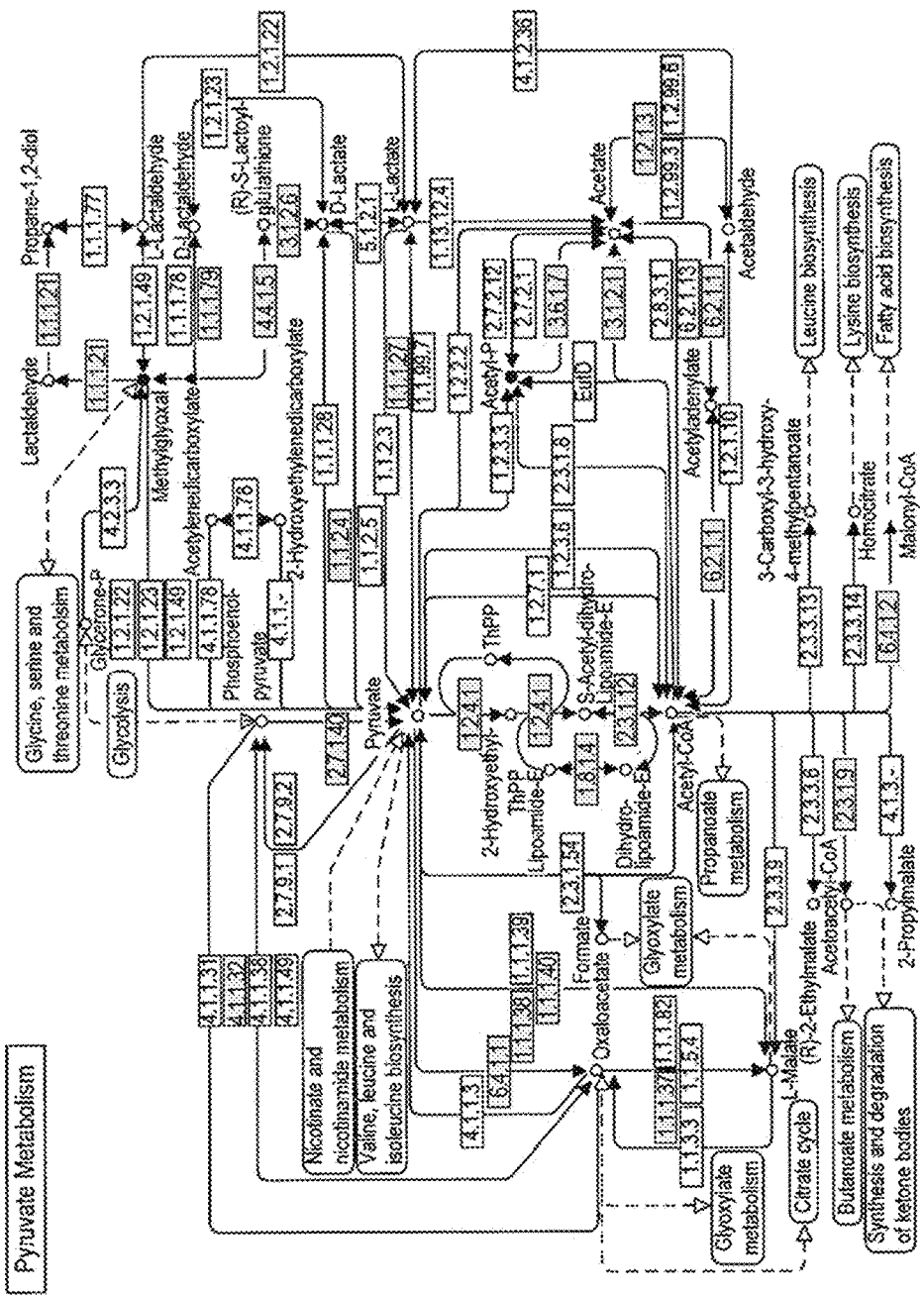

FIG. 24 depicts the pyruvate metabolic network, wherein the pathway is modified according to the present disclosure.

Figure 25:
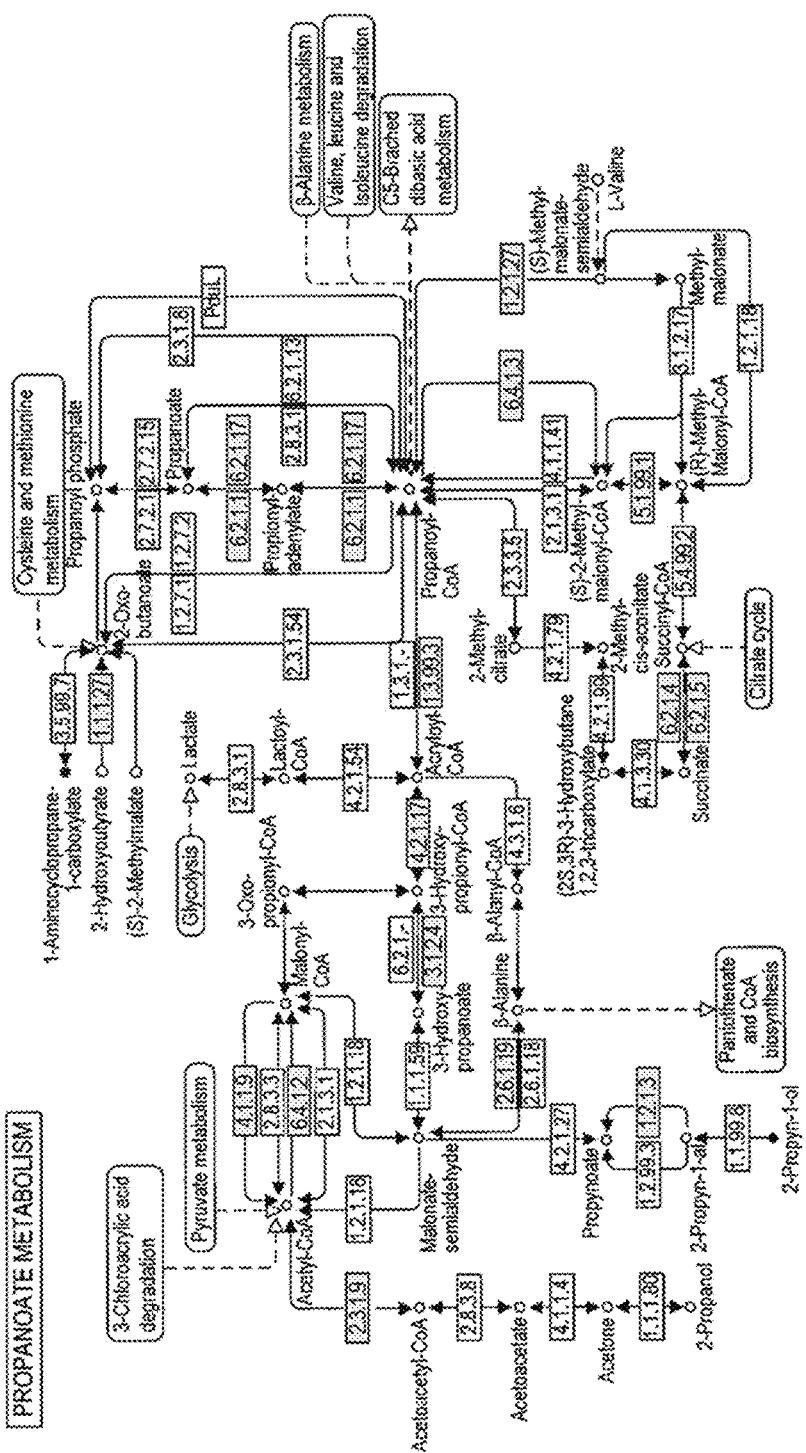
Figure 25:
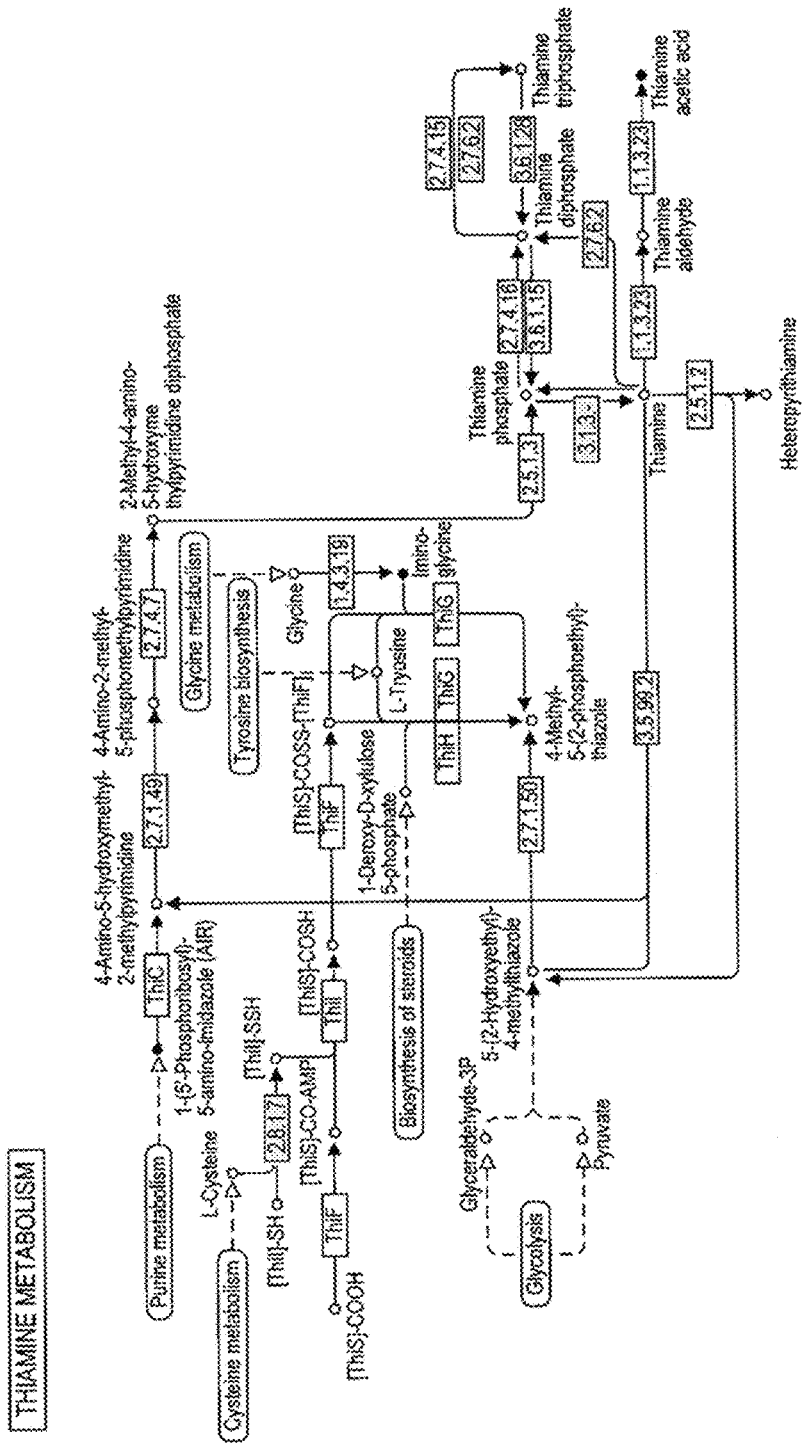

FIG. 25 depicts the propanoate metabolism and thiamine metabolic networks, wherein the respective pathways are modified as disclosed herein.

Figure 26:
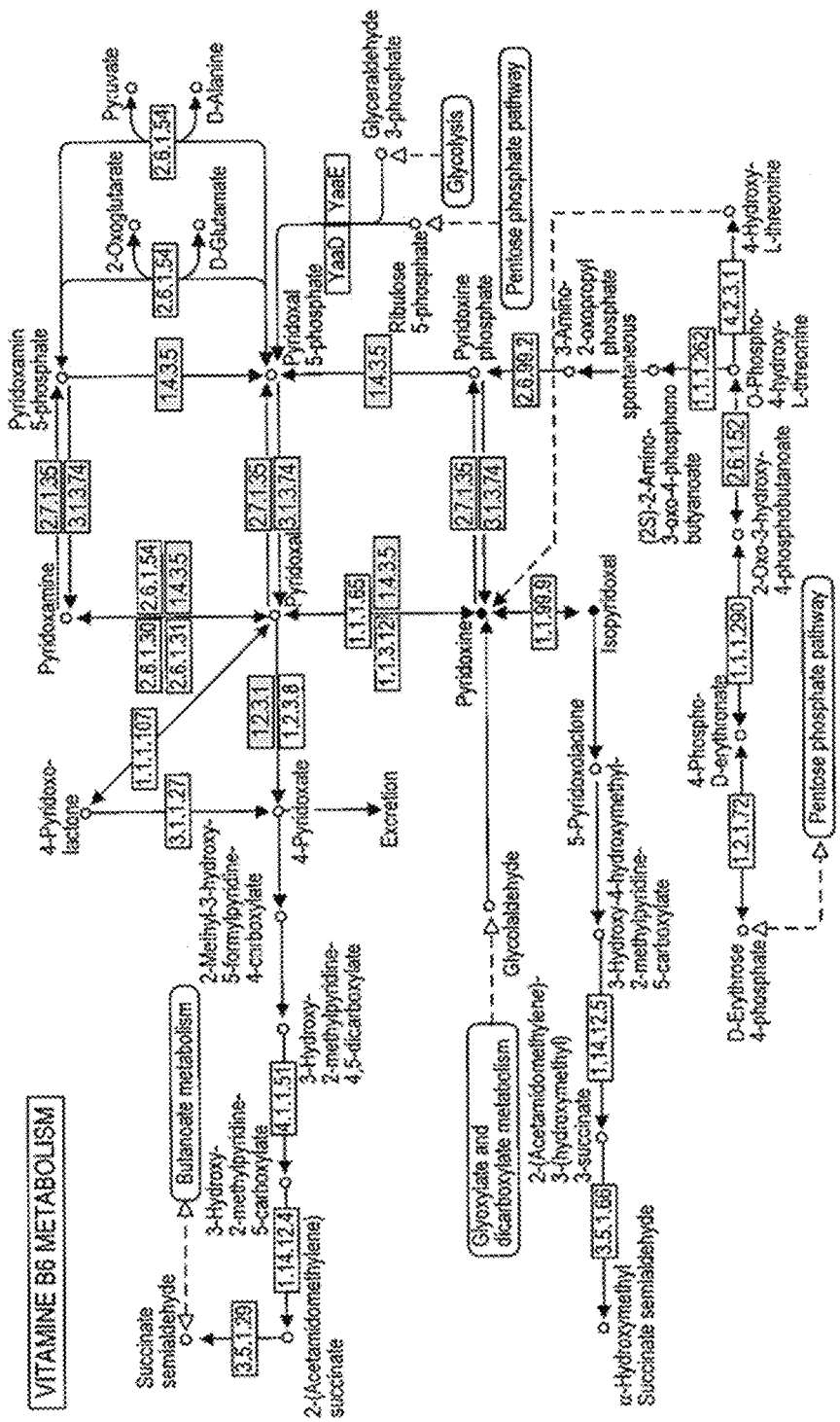

FIG. 26 depicts the vitamin B6 metabolic network, wherein the pathway is modified according to the present disclosure.

Figure 27:
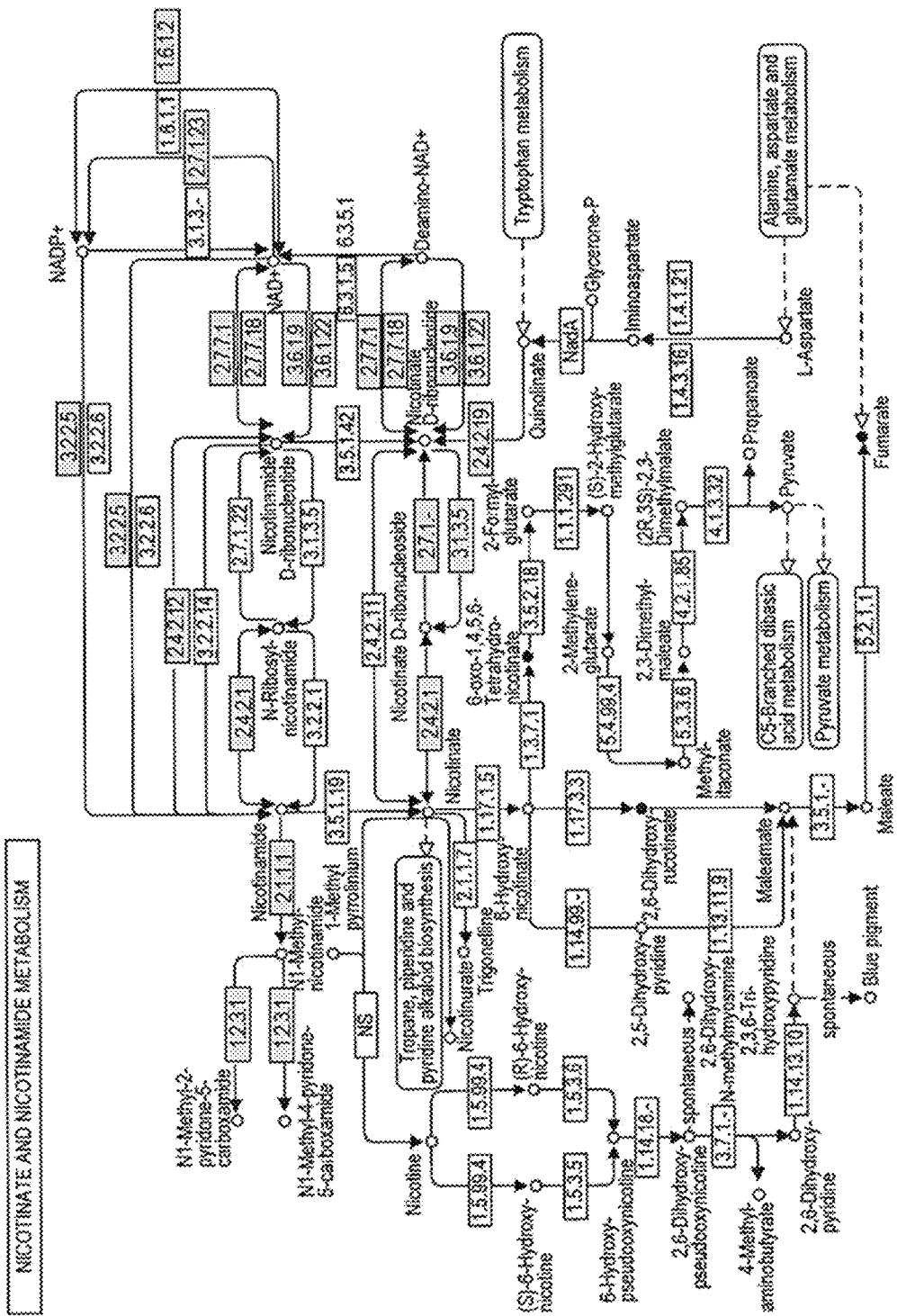

FIG. 27 depicts the nicotinate and nicotinamide metabolic networks, wherein the respective pathways are modified as disclosed herein.

Figure 28:
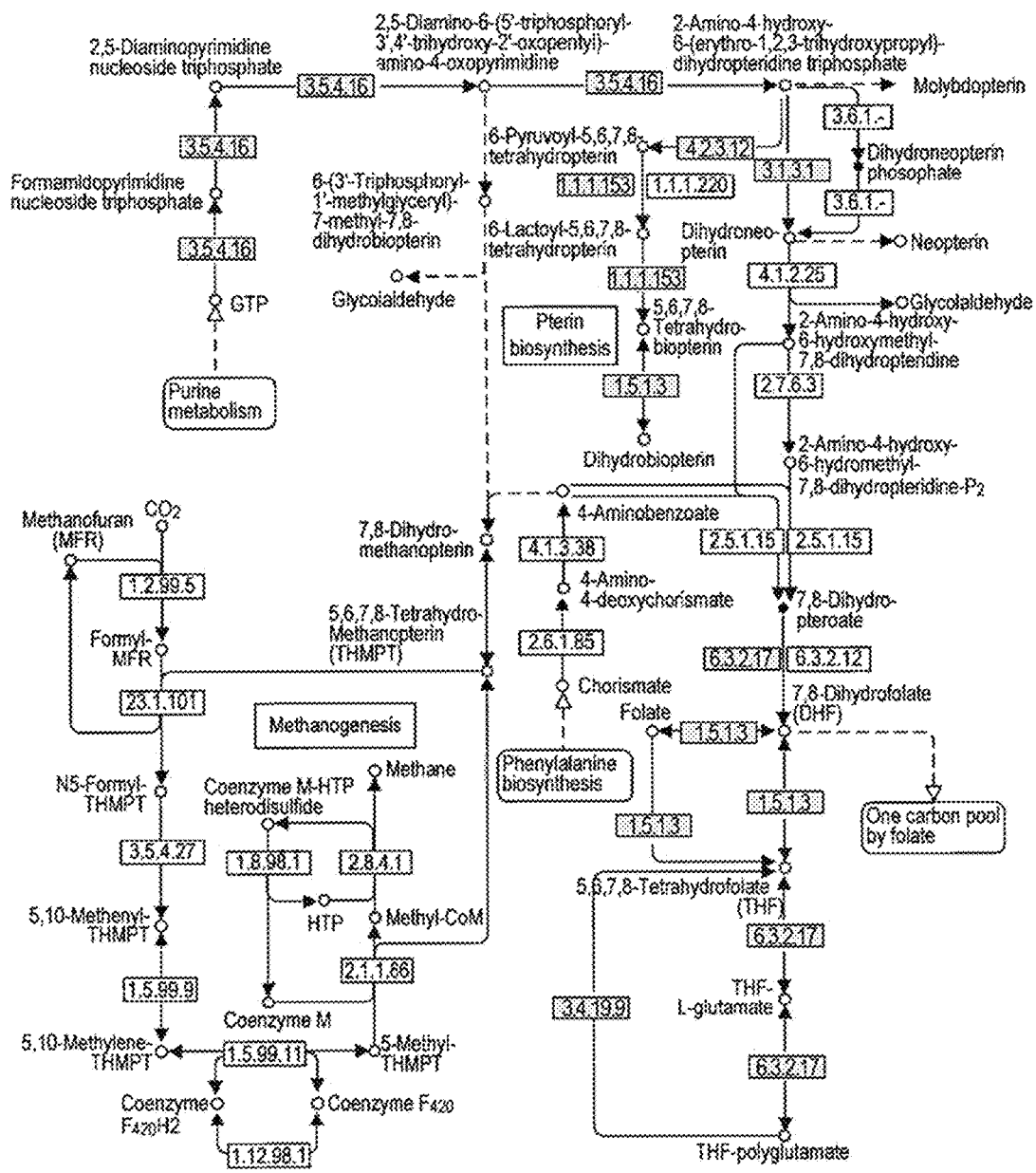

FIG. 28 depicts the folate biosynthesis pathway, wherein the pathway is modified according to the present disclosure.

Figure 29:
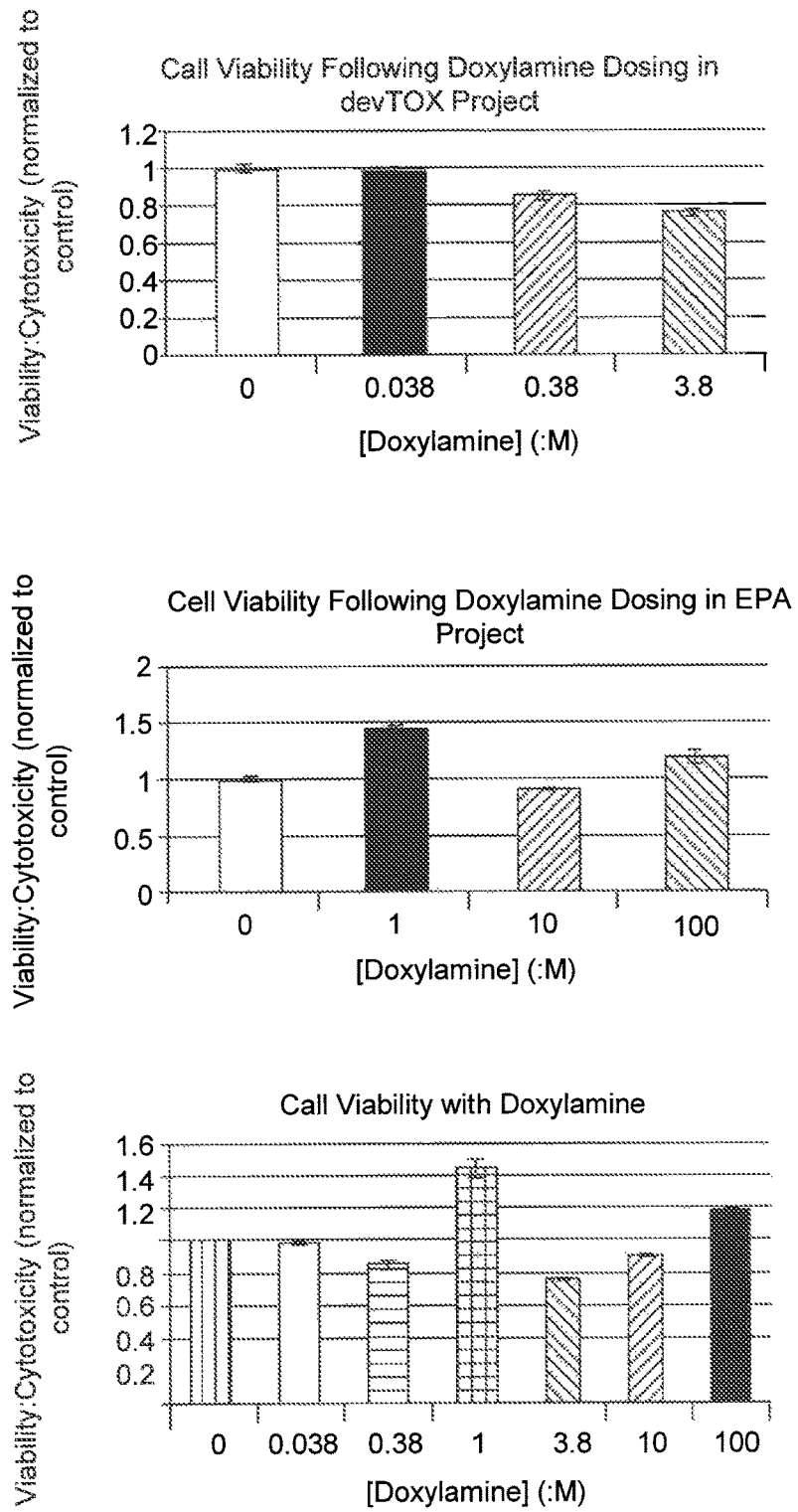

FIG. 29 illustrates cell viability data following doxylamine dosing of hES cells.

The present invention will now be described with reference to the accompanying drawings. It is understood that the drawings of the present application are not necessarily drawn to scale and that these figures and illustrations merely illustrate, but do not limit, the present invention.

DETAILED DESCRIPTION OF THE INVENTION

The invention provides reagents that are hSLCs, or hESC-derived lineage-specific cells, such as neural stem cells, neural precursor cells and neural cells produced therefrom, for assessing developmental toxicity using the human embryonic stem cell metabolome. hESCs are pluripotent, self-renewing cells isolated directly from preimplantation human embryos that recapitulate organogenesis in vitro. Lineage-specific precursor cells are derived from hESCs and have entered a specific cellular lineage, but yet remain multipotent with regard to cell type within that specific lineage. For example, neural precursors have committed to neural differentiation but yet remain unrestricted as to its neural cell type. Biochemical pathways of human development and disease are active in hSLCs, because they recapitulate differentiation into functional somatic cells. Disruption of these pathways during development contributes to disorders such as neural tube defects (NTDs) and cognitive impairment. Environmental agents, namely chemicals or drugs, participate in the ontogenesis of certain acquired congenital disorders.

This specification discloses one or more embodiments that incorporate the features of this invention. The disclosed embodiment(s) merely exemplify the invention. The scope of the invention is not limited to the disclosed embodiment(s). The invention is defined by the claims appended hereto.

In the following description, for purposes of explanation, specific numbers, parameters and reagents are set forth in order to provide a thorough understanding of the invention. It is understood, however, that the invention can be practiced without these specific details. In some instances, well-known features can be omitted or simplified so as not to obscure the present invention.

The embodiment(s) described, and references in the specification to "one embodiment", "an embodiment of the invention", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. For example, the description of a feature, a protein, a biological fluid, or a classifier may refer to a single feature, a protein, a biological fluid, or a classifier. Alternatively, the description of a feature, a protein, a biological fluid, or a classifier may refer to multiple features, proteins, biological fluids, or classifiers. Thus, as used herein, "a" or "an" may be singular or plural. Similarly, references to and descriptions of plural items may refer to single items.

It is understood that wherever embodiments are described herein with the language "comprising," otherwise analogous embodiments described in terms of "consisting of" and/or "consisting essentially of" are also provided.

The specification describes methods and kits for predicting and assaying teratogenicity of test compounds as well as methods for assaying test compounds for neural development disruption by detecting a specific set of purified cellular metabolites having a molecular weight of less than about 3000 Daltons that are differentially hSLCs cultured in the presence of known teratogenic compounds in comparison with hSLCs cultured in the absence the known teratogenic compounds. In certain embodiments, the metabolites have a molecular weight from about 50 to about 3000 Daltons. Specific exemplary embodiments for detecting marker proteins in the serum are provided herein. However, based on the teaching and guidance presented herein, it is understood that it is within the knowledge of one skilled in the art to readily adapt the methods described herein to.

Definitions

The metabolome, defined as the total dynamic set of cellular metabolites created through cellular metabolism, is a product of health or disease/insult states. Metabolites include but are not limited to sugars, organic acids, amino acids and fatty acids, particularly those species secreted, excreted, consumed, or identified by the cells, or those metabolites that are fluxed through the cells, that participate in functional mechanisms of cellular response to pathological or chemical insult. These metabolites serve as biomarkers of disease or toxic response and can be detected in biological fluids (Soga et al., 2006, J Biol Chem 281:16768-78; Zhao et al., 2006, Birth Defects Res A Clin Mol Teratol 76:230-6), including hSLC culture media. Importantly, metabolomic profiling may confirm functional changes that are often predicted by transcriptomics and proteomics.

Because it was known that hSLCs are highly sensitive to the culture microenvironment (Levenstein et al., 2005, Stem Cells 24: 568-574; Li et al., 2005, Biotechnol Bioeng 91:688-698), their application as a source of predictive biomarkers in response to chemical compounds, including toxins, teratogens and particularly pharmaceutical agents, drug lead compounds and candidate compounds in drug development, and their usefulness in establishing in vitro models of disease and development was uncertain, inter alia because those of skill in the art could anticipate that exposure to an exogenous chemicals could be highly detrimental to survival of hSLCs and preclude obtaining useful information from them. This concern has turned out not to be justified.

As used herein, the term "human stem-like cells (hSLCs)" is intended to include pluripotent, undifferentiated hESCs, as well as human induced pluripotent (iPS) cells, and human embryoid bodies.

As used herein, the term "human embryonic stem cells (hESCs)" is intended to include undifferentiated stem cells originally derived from the inner cell mass of developing blastocysts, and specifically pluripotent, undifferentiated human stem cells and partially-differentiated cell types thereof (e.g., downstream progenitors of differentiating hESC). As provided herein, in vitro cultures of hESCs are pluripotent and not immortalized, and can be induced to produce lineage-specific cells and differentiated cell types using methods well-established in the art. In preferred embodiments, hESCs useful in the practice of the methods of this invention are derived from preimplantation blastocysts as described by Thomson et al., in co-owned U.S. Pat. No. 6,200,806. Multiple hESC lines are currently available in US and UK stem cell banks.

As used herein, the term "human embryoid bodies" are aggregates of cells derived from human embryonic stem cells. Cell aggregation is imposed by hanging drop, plating upon non-tissue culture treated plates or spinner flasks; either method prevents cells from adhering to a surface to form the typical colony growth. Upon aggregation, differentiation is initiated and the cells begin to a limited extent to recapitulate embryonic development. Embryoid bodies are composed of cells from all three germ layers: endoderm, ectoderm and mesoderm.

As used herein, the term "human induced pluripotent stem cells", commonly abbreviated as iPS cells are a type of pluripotent stem cell artificially derived from a non-pluripotent cell, typically an adult somatic cell, by inducing a forced expression of certain genes. iPS cells are believed to be identical to natural pluripotent stem cells, such as embryonic stem cells in many respects, such as the expression of certain stem cell genes and proteins, chromatin methylation patterns, doubling time, embryoid body formation, teratoma formation, viable chimera formation, and potency and differentiability.

In one embodiment, the cells of the present invention can also include hSLC-derived lineage specific cells. The terms "hSLC-derived lineage specific cells", "stem cell progenitor," "lineage-specific cell," "hSLC derived cell" and "differentiated cell" as used herein are intended to encompass lineage-specific cells that are differentiated from hSLCs such that the cells have committed to a specific lineage of diminished pluripotency. For example, hSLC-derived lineage specific cells are derived from hSLCs and have entered a specific cellular lineage, but yet remain multipotent with regard to cell type within that specific lineage. The hSLC-derived lineage specific cells can include, for example, neural stem cells, neural precursor cells, neural cells, cardiac stem cells, cardiac precursor cells, cardiomyocytes, and the like. In some embodiments, these hSLC-derived lineage-specific cells remain undifferentiated with regard to final cell type. For example, neuronal stem cells are derived from hSLCs and have differentiated enough to commit to neuronal lineage. However, the neuronal precursor retains "stemness" in that it retains the potential to develop into any type of neuronal cell. Additional cell types include terminally-differentiated cells derived from hESCs or lineage-specific precursor cells, for example neural cells.

The term "cellular metabolite" and "metabolite" have been used herein interchangeably. The terms "cellular metabolite" or "metabolite" as used herein refer to any small molecule secreted, excreted or identified by hSLCs or any small molecule that is fluxed through hSLCs or lineage-specific precursor cells, for example, neural cells. In preferred embodiments, cellular metabolites or metabolites include but are not limited to sugars, organic acids, amino acids, fatty acids, hormones, vitamins, oligopeptides (less than about 100 amino acids in length), as well as ionic fragments thereof. Cells can also be lysed in order to measure cellular products present within the cell. In particular, said metabolites are less than about 3000 Daltons in molecular weight, and more particularly from about 50 to about 3000 Daltons.

The term "metabolic effect" of a teratogenic compound as used herein refers to the difference in a plurality of metabolites of one or more metabolic networks in hSLCs cultured in presence of the teratogenic compound in comparison with hSLCs cultured in absence of the teratogenic compound, or hSLCs cultured in presence of a known non-teratogenic compound, wherein the plurality of metabolites are identical to metabolites affected by a known disruption of the one or more metabolic networks. In one embodiment, the metabolites can be differentially expressed. In one aspect, for example, the expression of the metabolites is increased when exposed to a teratogenic compound and decreased when exposed to a non-teratogenic compound. In another aspect, for example, the metabolites are secreted when exposed to a teratogenic compound and not secreted when exposed to a non-teratogenic compound.

The term "metabolic response" as used herein refers to a change caused through alterations in enzyme activity (e.g. regulation by allosteric, covalent modification, or protein processing), enzyme abundance, non-enzymatic chemical reactions, cellular transporters, and action of enzymes in the extracellular space leading to changes in abundance of one or more metabolites or flux of media components in response to an experimental treatment. The response can be measured both by changes in abundance of one or more metabolites in the extracellular or intracellular environment.

In one embodiment, one or more of the measured metabolites is a metabolite secreted from the hSLCs.

In one embodiment, one or more of the measured metabolites is a metabolite excreted from the hSLCs.

In one embodiment, one or more of the measured metabolites is a metabolite consumed by the hSLCs.

In one embodiment, one or more of the measured metabolites is a metabolite identified by the hSLCs.

In one embodiment, the difference in metabolic response for the secreted, excreted, consumed, or identified metabolite associated with hSLCs cultured in the presence of a test compound or a known teratogenic compound in comparison with hSLCs cultured in the absence of a test compound or a known teratogenic compound is determined by measuring the flux of the metabolite through the hSLCs.

The term "flux" as used herein refers to the turnover of metabolites by catabolism and/or anabolism through the metabolic networks and networks of an organism. The metabolic footprint observed by measuring the differential utilization of media components following treatments of cultures is an example of metabolic flux.

The term "identified" as used herein refers to cellular metabolites that are secreted or consumed by hSLCs. The term also encompasses cellular metabolites that are fluxed through hSLCs.

hSLCs are cultured according to the methods of the invention using standard methods of cell culture well-known in the art, including, for example those methods disclosed in Ludwig et al. (2006, Feeder-independent culture of human embryonic stem cells, Nat Methods 3: 637-46). In preferred embodiments, hSLCs are cultured in the absence of a feeder cell layer during the practice of the inventive methods; however, hSLCs can be cultured on feeder cell layer prior to the practice of the methods of this invention.

The terms "administering" or "dosing" as used herein refer to contacting in vitro cultures of hSLCs with a toxic, teratogenic, or test chemical compound. In a preferred embodiment the dosage of the compound is administered in an amount equivalent to levels achieved or achievable in vivo, for example, in maternal circulation.

The phrases "identifying metabolites that are differentially produced" or "detecting alterations in the cells or alternations in metabolism" as used herein include but are not limited to comparisons of treated hSLCs to untreated (control) cells (i.e., cells cultured in the presence (treated) or absence (untreated) of a toxic, teratogenic, or test chemical compound. Detection or measurement of variations in cellular metabolites, excreted or secreted or metabolized in the medium therefrom, between treated and untreated cells is included in this definition. In a preferred embodiment, alterations in cells or cell activity are measured by determining a profile of changes in cellular metabolites having a molecular weight of less than 3000 Daltons, more particularly between 50 and 3000 Daltons, in a treated versus untreated cell.

The terms "metabolic pathway" or "metabolic network" or "metabolism pathway" as used herein refers to a series of chemical reactions occurring within a cell. In each pathway, a principal compound is modified by one or more chemical or enzymatic reactions. Moreover, a metabolic pathway can be composed of a series of biochemical reactions connected by their intermediates. The reactants (or substrates) of one reaction can be the products of a previous reaction, and so on. Metabolic pathways are usually considered in one direction (although most reactions are reversible, conditions in the cell are such that it is thermodynamically more favorable for flux to be in one of the directions). Enzymes catalyze the reactions of a metabolic pathway, and often require dietary minerals, vitamins, and other cofactors in order to function properly. Because of the many compounds that may be involved, pathways can be quite elaborate. In addition, many pathways can exist within a cell. This collection of pathways is called the metabolic network. Metabolic pathways and networks are important to the maintenance of homeostasis within an organism. In one embodiment, a compound comprises one or more biological molecules of a metabolic pathway or network that are modified by one or more chemical or enzymatic reactions. In another embodiment a compound comprises one or more products of a metabolic pathway or network that are modified by one or more chemical or enzymatic reactions. In another aspect a compound comprises one or more intermediates of a metabolic pathway or network that are modified by one or more chemical or enzymatic reactions. In yet another embodiment a compound comprises one or more reactants of a metabolic pathway or network that are modified by one or more chemical or enzymatic reactions. Any person of skill in the art would understand that a metabolic pathway or metabolic network, as defined herein, includes one or more compounds associated with anabolic and/or catabolic metabolism of a particular metabolite. For example, glutathione pathway comprises products or reactants associated with anabolic and/or catabolic metabolism of glutathione.

The term "correlating" or "associating" or "pattern matching" as used herein refers to the positive correlation, or association, or matching of alterations of patterns in cellular metabolites including but not limited to sugars, organic acids, amino acids, fatty acids, and low molecular weight compounds excreted or secreted from hSLCs, to an in vivo toxic response. The screened cellular metabolites can be involved in a wide range of biochemical pathways in the cells and related to a variety of biological activities including, but not limited to inflammation, anti-inflammatory response, vasodilation, neuroprotection, oxidative stress, antioxidant activity, DNA replication and cell cycle control, methylation, and biosynthesis of, inter alia, nucleotides, carbohydrates, amino acids and lipids, among others. Alterations in specific subsets of cellular metabolites can correspond to a particular metabolic or developmental pathway and thus reveal effects of a test compound on in vivo development.

In one embodiment, cellular metabolites are identified using a physical separation method.

The term "physical separation method" as used herein refers to any method known to those with skill in the art sufficient to produce a profile of changes and differences in small molecules produced in hSLCs, contacted with a toxic, teratogenic or test chemical compound according to the methods of this invention. In a preferred embodiment, physical separation methods permit detection of cellular metabolites including but not limited to sugars, organic acids, amino acids, fatty acids, hormones, vitamins, and oligopeptides, as well as ionic fragments thereof and low molecular weight compounds (preferably with a molecular weight less than 3000 Daltons, and more particularly between 50 and 3000 Daltons). For example, mass spectrometry can be used. In particular embodiments, this analysis is performed by liquid chromatography/electrospray ionization time of flight mass spectrometry (LC/ESI-TOF-MS), however it will be understood that cellular metabolites as set forth herein can be detected using alternative spectrometry methods or other methods known in the art for analyzing these types of cellular compounds in this size range.

The term "biomarker" as used herein refers to metabolites that exhibit significant alterations between hSLCs cultured in the presence of a test compound or a known teratogenic compound in comparison with hSLCs cultured in the absence of the test compound or the known teratogenic compound. In one embodiment, at least one of the metabolites is secreted or excreted from the hSLCs or consumed or identified by hSLCs in greater amounts in the presence of the test compound or known teratogenic compound than in the absence of the test compound or the known teratogenic compound. In another embodiment, at least one of the cellular metabolites is secreted or excreted from the hSLCs in lower amounts in the presence of the test compound or known teratogenic compound than in the absence of the test compound or the known teratogenic compound.

In preferred embodiments, biomarkers are identified by methods including LC/ESI-TOF-MS and QTOF-MS. Metabolomic biomarkers are identified by their unique molecular mass and consistency with which the marker is detected in response to a particular toxic, teratogenic or test chemical compound; thus the actual identity of the underlying compound that corresponds to the biomarker is not required for the practice of this invention.

Alternatively, certain biomarkers can be identified by, for example, gene expression analysis, including real-time PCR, RT-PCR, Northern analysis, and in situ hybridization.

In addition, biomarkers can be identified using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry (e.g., MS/MS, MS/MS/MS, ESI-MS/MS etc.), secondary ion mass spectrometry (SIMS), or ion mobility spectrometry (e.g. GC-IMS, IMS-MS, LC-IMS, LC-IMS-MS etc.).

Mass spectrometry methods are well known in the art and have been used to quantify and/or identify biomolecules, such as proteins and other cellular metabolites (see, e.g., Li et al., 2000; Rowley et al., 2000; and Kuster and Mann, 1998).

In certain embodiments, a gas phase ion spectrophotometer is used. In other embodiments, laser-desorption/ionization mass spectrometry is used to identify biomarkers. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI").

In MALDI, the analyte (e.g. biomarkers) is mixed with a solution containing a matrix, and a drop of the liquid is placed on the surface of a substrate. The matrix solution then co-crystallizes with the biomarkers. The substrate is inserted into the mass spectrometer. Laser energy is directed to the substrate surface where it desorbs and ionizes the proteins without significantly fragmenting them. However, MALDI has limitations as an analytical tool. It does not provide means for fractionating the biological fluid, and the matrix material can interfere with detection, especially for low molecular weight analytes.

In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the biomarker of interest and that contain a photolytic bond that is broken upon application of the laser. In each of these methods, the derivatizing agent generally is localized to a specific location on the substrate surface where the sample is applied. The two methods can be combined by, for example, using a SELDI affinity surface to capture an analyte (e.g. biomarker) and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4$^{th}$ ed. Vol. 15 (John Wiley & Sons, New York 1995), pp. 1071-1094.

In some embodiments, the data from mass spectrometry is represented as a mass chromatogram. A "mass chromatogram" is a representation of mass spectrometry data as a chromatogram, where the x-axis represents time and the y-axis represents signal intensity. In one aspect the mass chromatogram is a total ion current (TIC) chromatogram. In another aspect, the mass chromatogram is a base peak chromatogram. In other embodiments, the mass chromatogram is a selected ion monitoring (SIM) chromatogram. In yet another embodiment, the mass chromatogram is a selected reaction monitoring (SRM) chromatogram. In a preferred embodiment, the mass chromatogram is an extracted ion chromatogram (EIC).

In an EIC, a single feature is monitored throughout the entire run. The total intensity or base peak intensity within a mass tolerance window around a particular analyte's mass-to-charge ratio is plotted at every point in the analysis. The size of the mass tolerance window typically depends on the mass accuracy and mass resolution of the instrument collecting the data. As used herein, the term "feature" refers to a single small metabolite, or a fragment of a metabolite. In some embodiments, the term feature may also include noise upon further investigation.

Detection of the presence of a biomarker will typically involve detection of signal intensity. This, in turn, can reflect the quantity and character of a biomarker bound to the substrate. For example, in certain embodiments, the signal strength of peak values from spectra of a first sample and a second sample can be compared (e.g., visually, by computer analysis etc.) to determine the relative amounts of particular biomarkers. Software programs such as the Biomarker Wizard program (Ciphergen Biosystems, Inc., Fremont, Calif.) can be used to aid in analyzing mass spectra. The mass spectrometers and their techniques are well known.

A person skilled in the art understands that any of the components of a mass spectrometer, e.g., desorption source, mass analyzer, detect, etc., and varied sample preparations can be combined with other suitable components or preparations described herein, or to those known in the art. For example, in some embodiments a control sample may contain heavy atoms, e.g. $^{13}C$, thereby permitting the test sample to be mixed with the known control sample in the same mass spectrometry run. Good stable isotopic labeling is included.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In one embodiment of the invention, levels of biomarkers are detected by MALDI-TOF mass spectrometry.

Methods of detecting biomarkers also include the use of surface plasmon resonance (SPR). The SPR biosensing technology has been combined with MALDI-TOF mass spectrometry for the desorption and identification of biomarkers.

Data for statistical analysis can be extracted from chromatograms (spectra of mass signals) using softwares for statistical methods known in the art. "Statistics" is the science of making effective use of numerical data relating to groups of individuals or experiments. Methods for statistical analysis are well-known in the art.

In one embodiment a computer is used for statistical analysis.

In one embodiment, the Agilent MassProfiler or MassProfilerProfessional software is used for statistical analysis. In another embodiment, the Agilent MassHunter software Qual software is used for statistical analysis. In other embodiments, alternative statistical analysis methods can be used. Such other statistical methods include the Analysis of Variance (ANOVA) test, Chi-square test, Correlation test, Factor analysis test, Mann-Whitney U test, Mean square weighted derivation (MSWD), Pearson product-moment correlation coefficient, Regression analysis, Spearman's rank correlation coefficient, Student's T test, Welch's T-test, Tukey's test, and Time series analysis.

In different embodiments signals from mass spectrometry can be transformed in different ways to improve the performance of the method. Either individual signals or summaries of the distributions of signals (such as mean, median or variance) can be so transformed. Possible transformations include taking the logarithm, taking some positive or negative power, for example the square root or inverse, or taking the arcsin (Myers, Classical and Modern Regression with Applications, $2^{nd}$ edition, Duxbury Press, 1990).

In different embodiments, statistical classification algorithms are used to create a classification model in order to predict teratogenicity and non-teratogenicity of test compounds. Machine learning-based classifiers have been applied in various fields such as machine perception, medical diagnosis, bioinformatics, brain-machine interfaces, classifying DNA sequences, and object recognition in computer vision. Learning-based classifiers have proven to be highly efficient in solving some biological problems.

As used herein, "classification" is the process of learning to separate data points into different classes by finding common features between collected data points which are within known classes. In statistics, classification is the problem of identifying the sub-population to which new observations belong, where the identify of the sub-population is unknown, on the basis of a training set of data containing observations whose sub-population is known. Thus the requirement is that new individual items are placed into groups based on quantitative information on one or more measurements, traits or characteristics, etc) and based on the training set in which previously decided groupings are already established. Classification problem has many applications. In some cases, it is employed as a data mining procedure, while in others more detailed statistical modeling is undertaken.

As used herein, a "classifier" is a method, algorithm, computer program, or system for performing data classification. Examples of widely used classifiers include, but are not limited to, the Neural network (multi-layer perceptron), Support vector machines, k-nearest neighbors, Gaussian mixture model, Gaussian, naive Bayes, Decision tree, and RBF classifiers.

In some embodiments, classification models to predict teratogenicity and non-teratogenicity of test compounds are created using either Linear classifiers (for e.g., partial least squares determinant analysis (PLS-DA), Fisher's linear discriminant, Logistic regression, Naive Bayes classifier, Perceptron), Support vector machines (for e.g., least squares support vector machines), quadratic classifiers, Kernel estimation (for e.g., k-nearest neighbor), Boosting, Decision trees (for e.g., Random forests), Neural networks, Bayesian networks, Hidden Markov models, or Learning vector quantization.

In a preferred embodiment, the Random forest model is used to create a classification model in order to predict teratogenicity and non-teratogenicity of test compounds.

Random forest (or random forests) is an ensemble classifier that consists of many decision trees and outputs the class that is the mode of the class's output by individual trees. A "decision tree" is a decision support tool that uses a tree-like graph or model of decisions and their possible consequences, including chance event outcomes, resource costs, and utility. It is one way to display an algorithm. Decision trees are commonly used in operations research, specifically in decision analysis, to help identify a strategy most likely to reach a goal. Another use of decision trees is as a descriptive means for calculating conditional probabilities. Decision tree learning, used in statistics, data mining and machine learning, uses a decision tree as a predictive model which maps observations about an item to conclusions about the item's target value. More descriptive names for such tree models are classification trees or regression trees. In these tree structures, leaves represent classifications and branches represent conjunctions of features that lead to those classifications.

As used herein, a "training set" is a set of data used in various areas of information science to discover potentially predictive relationships. Training sets are used in artificial intelligence, machine learning, genetic programming, intelligent systems, and statistics. In all these fields, a training set has much the same role and is often used in conjunction with a test set.

As used herein, a "test set" is a set of data used in various areas of information science to assess the strength and utility of a predictive relationship. Test sets are used in artificial intelligence, machine learning, genetic programming, intelligent systems, and statistics. In all these fields, a test set has much the same role.

As used herein, "regression analysis" includes any techniques for modelling and analyzing several variables, when the focus is on the relationship between a dependent variable and one or more independent variables. More specifically, regression analysis helps understand how the typical value of the dependent variable changes when any one of the independent variables is varied, while the other independent variables are held fixed. Most commonly, regression analysis estimates the conditional expectation of the dependent variable given the independent variables—that is, the average value of the dependent variable when the independent variables are held fixed. Less commonly, the focus is on a quantile, or other location parameter of the conditional distribution of the dependent variable given the independent variables. In all cases, the estimation target is a function of the independent variables called the regression function. In regression analysis, it is also of interest to characterize the variation of the dependent variable around the regression function, which can be described by a probability distribution. Regression analysis is widely used for prediction and forecasting, where its use has substantial overlap with the field of machine learning. Regression analysis is also used to understand which among the independent variables are related to the dependent variable, and to explore the forms of these relationships. In restricted circumstances, regression analysis can be used to infer causal relationships between the independent and dependent variables. A large body of techniques for carrying out regression analysis has been developed. Familiar methods such as linear regression and ordinary least squares regression are parametric, in that the regression function is defined in terms of a finite number of unknown parameters that are estimated from the data. Nonparametric regression refers to techniques that allow the regression function to lie in a specified set of functions, which may be infinite-dimensional.

"Sensitivity" and "specificity" are statistical measures of the performance of a binary classification test. Sensitivity (also called recall rate in some fields) measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction can achieve 100% sensitivity (i.e. predict all people from the sick group as sick) and 100% specificity (i.e. not predict anyone from the healthy group as sick). A specificity of 100% means that the test recognizes all actual negatives—for example, in a test for a certain disease, all disease free people will be recognized as disease free. A sensitivity of 100% means that the test recognizes all actual positives—for example, all sick people are recognized as being ill. Thus, in contrast to a high specificity test, negative results in a high sensitivity test are used to rule out the disease. A positive result in a high specificity test can confirm the presence of disease. However, from a theoretical point of view, a 100%-specific test standard can also be ascribed to a 'bogus' test kit whereby the test simply always indicates negative. Therefore the specificity alone does not tell us how well the test recognizes positive cases. A knowledge of sensitivity is also required. For any test, there is usually a trade-off between the measures. For example, in a diagnostic assay in which one is testing for people who have a certain condition, the assay may be set to overlook a certain percentage of sick people who are correctly identified as having the condition (low specificity), in order to reduce the risk of missing the percentage of healthy people who are correctly identified as not having the condition (high sensitivity). This trade-off can be represented graphically using a receiver operating characteristic (ROC) curve.

The "accuracy" of a measurement system is the degree of closeness of measurements of a quantity to its actual (true) value. The "precision" of a measurement system, also called reproducibility or repeatability, is the degree to which repeated measurements under unchanged conditions show the same results. Although the two words can be synonymous in colloquial use, they are deliberately contrasted in the context of the scientific method. A measurement system can be accurate but not precise, precise but not accurate, neither, or both. For example, if an experiment contains a systematic error, then increasing the sample size generally increases precision but does not improve accuracy. Eliminating the systematic error improves accuracy but does not change precision.

The term "predictability" (also called banality) is the degree to which a correct prediction or forecast of a system's state can be made either qualitatively or quantitatively. Perfect predictability implies strict determinism, but lack of predictability does not necessarily imply lack of determinism. Limitations on predictability could be caused by factors such as a lack of information or excessive complexity.

In one embodiment, the relative amounts of one or more biomarkers present in a first or second sample of a biological fluid are determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomarker that is present in the first and second samples. A standard containing a known amount of a biomarker can be analyzed as the second sample to provide better quantify the amount of the biomarker present in the first sample. In certain embodiments, the identity of the biomarkers in the first and second sample can also be determined The basal metabolome of undifferentiated hSLCs serve as a collection of biochemical signatures of functional pathways that are relevant for stemness and self-renewal. Metabolite profiling can be conducted on excreted, secreted or consumed or identified cellular metabolites as opposed to intracellular compounds. Ultimately, biomarkers discovered in vitro are expected to be useful for analyzing in vivo biofluids that contain complex mixtures of extracellular biomolecules. Such biofluids include but are not limited to serum, whole blood, plasma, sputum, cerebrospinal fluid, pleural fluid, amniotic fluid, urine and the like. This is advantageous over invasive procedures such as tissue biopsies because small molecules in biofluids can be detected non-invasively (in contrast to intracellular compounds). In addition, processing cellular supernatant for mass spectrometry is more robust and less laborious than cellular extracts. However, cellular extracts (from, for example, lysed cells) can be utilized in the methods of the invention.

The term "biomarker profile" as used herein refers to a plurality of biomarkers identified by the inventive methods. Biomarker profiles according to the invention can provide a molecular "fingerprint" of the toxic and teratogenic effects of a test compound and convey what cellular metabolites, specifically excreted and secreted cellular metabolites, are significantly altered following test compound administration to hSLCs. In these embodiments, each of the plurality of biomarkers is characterized and identified by its unique molecular mass and consistency with which the biomarker is detected in response to a particular toxic, teratogenic or test chemical compound; thus the actual identity of the underlying compound that corresponds to the biomarker is not required for the practice of this invention.

The term "biomarker portfolio" as used herein refers to a collection of individual biomarker profiles. The biomarker portfolios can be used as references to compare biomarker profiles from novel or unknown compounds. Biomarker portfolios can be used for identifying common pathways, particularly metabolic or developmental pathways, of toxic or teratogenic response.

The results set forth herein demonstrate that hSLC metabolomics can be used in biomarker discovery and pathway identification. Metabolomics detected small molecules secreted or excreted by hSLCs, consumed by hSLCs, or the flux of metabolites through hSLCs. The identified biomarkers can be used for at least two purposes: first, to determine specific metabolic or biochemical pathways or networks that respond to or are affected by toxin or teratogen exposure, particularly said pathways utilized or affected during early development that are sensitive to toxic, teratogenic or test chemical compounds that are developmental disruptors and participate in the ontogenesis of birth defects; and second, to provide metabolites that can be measured in biofluids to assist management and diagnosis of toxic exposure, birth defects or other disease.

In one embodiment, the metabolites of a biomarker portfolio are mapped to one or more metabolic networks in order to determine key developmental pathways affected by a test compound. In one aspect, online databases are used to map the metabolites to one or more developmental pathways. These online databases include, but are not limited to, HMDB, KEGG, PubChem Compound, and METLIN. In another embodiment, one or more developmental processes associated with the one or more metabolic networks are identified in order to determine one or more developmental processes or pathways disrupted by a test compound.

In a further embodiment, the potential specific effect of a teratogenic compound can be identified with further consideration. Specifically, by way of example, it is known that certain developmental or biological defects are correlated to disruptions in one or more metabolic networks, and by not just identifying the existence of the metabolites affected by the disruption of these metabolic networks, but further comparing the affected metabolites to their normal metabolic network profiles, a person of skill in the art would be able to correlate the specific effect of the teratogenic compound to its potential specific biological effect on a patient. This type of information helps to elucidate specific developmental pathways that may be affected by exposure to a teratogenic compound.

A biomarker portfolio from hSLCs can also serve as a high throughput screening tool in preclinical phases of drug discovery. In addition, this approach can be used to detect detrimental effects of environmental (heavy metals, industrial waste products) and nutritional chemicals (such as alcohol) on human development. Ultimately, the methods of this invention utilizing the hSLC metabolome can assist pharmaceutical, biotechnology and environmental agencies on decision-making towards development of compounds and critical doses for human exposure. The integration of chemical biology to embryonic stem cell technology also offers unique opportunities to strengthen understanding of human development and disease. Metabolomics of cells differentiated from hSLCs should serve similar roles and be useful for elucidating mechanisms of toxicity and disease with greater sensitivity for particular cell or tissue types, and in a human-specific manner.

For example, key metabolic networks, including as set forth herein arginine, aspartic acid, gamma aminobutyric acid (GABA), glutamate and isoleucine synthesis and degradation, may be differentially disrupted in earlier versus later stages of human development. In addition, metabolite profiles of neural precursor cells or neuronal cell populations can reveal biomarkers of neurodevelopmental disorders in target cell types. The association of metabolomics to stem cell biology can inform the mechanisms of action of folic acid and neural tube defects in the early human embryo.

Biomarker portfolios produced using the hSLC-dependent methods of this invention can also be used in high throughput screening methods for preclinical assessment of drug candidates and lead compounds in drug discovery. This aspect of the inventive methods produces minimal impact on industry resources in comparison to current developmental toxicology models, since implementation of this technology does not require experimental animals. The resulting positive impact on productivity enables research teams in the pharmaceutical industry to select and advance compounds into exploratory development with greater confidence and decreased risk of encountering adverse developmental effects.

The term "developmental pathway" or "developmental process" or "developmental network" as used herein refers to biochemical or metabolic networks involved in embryonic and fetal development.

"Supernatant" as used herein can include but is not limited to extracellular media, co-cultured media, cells, or a solution of fractionated or lysed cells.

Metabolite profiles obtained from analysis of toxins, teratogens, alcohol, and test chemical compounds can be used to compose a library of biomarker portfolios. These portfolios can then be used as a reference for toxicological analysis of unknown chemical compounds. Metabolic profiles of novel compounds can be compared to known biomarker portfolios to identify common mechanisms of toxic response. This approach can reveal functional markers of toxic response, which serve as screening molecules that are shared at least in part as a consequence of exposure to various different toxic and teratogenic compounds. Such hSLC-derived small molecules can be used as measurable mediators of toxic response that refine or replace costly and complex screening systems (such as in vivo animal models) and have the additional advantage of being specific for human cells and human metabolic and developmental pathways.

Kits

As a matter of convenience, the method of this invention can be provided in the form of a kit. Such a kit is a packaged combination comprising the basic elements of: a) a first container comprising, in solid form, a specific set of purified metabolites having a molecular weight of less than about 3000 Daltons, wherein a difference in the specific set of purified metabolites associated with hSLCs cultured in the presence of known teratogenic compounds versus hSLCs cultured in the absence of known teratogenic compounds indicates a difference in metabolic response of hSLCs cultured in the presence of the known teratogenic compounds in comparison with hSLCs cultured in the absence the known teratogenic compounds; and b) a second container comprising a physiologically suitable buffer for resuspending the specific subset of purified metabolites.

In one embodiment, the kit can further include an instruction sheet, describing how to carry out the assay of the kit.

In another embodiment, the kit can also encompass one or more reagents to analyze fluctuations of expression and/or activity of one or more enzymes which are involved in the endogenous biological reactions which result in the synthesis and/or conversion of one or more metabolites disclosed herein. Thus, the kit is not limited to the analysis and detection of small molecule biomarkers, but also of the enzymes which are inherent components of the metabolic neworks described herein. In one embodiment, analysis of enzyme activity and/or concentration in the kit, as an indicator of metabolite changes can be performed by assays including but not limited to gene expression analysis, ELISA and other immunoassays as well as enzyme substrate conversion.

In another embodiment, the invention discloses a method for validating a test compound as a teratogen. In one embodiment, the method comprises providing a set of metabolites having a molecular weight of less than about 3000 Daltons. In one aspect, the metabolites are provided in the same container. Ina another aspect, each metabolite is provided in a separate container. In one aspect, the metabolites are differentially metabolized by hSLCs cultured in the presence of one or more known teratogenic compounds in comparison with hSLCs cultured in the absence of a teratogenic compound. In one aspect, the metabolitres are provided in a solid form. In another aspect, the metabolites are provided in a liquid form. Thus, in one embodiment, the method comprises resuspending the set of metabolites. In one aspect, the metabolites are resuspended in a buffer. In another aspect, metabolites are resuspended in any suitable liquid. In another aspect, the buffer is a physiologically suitable buffer. In one aspect, the metabolites are resuspended in a predetermined volume of the buffer. In another aspect, the final concentration of each metabolite in the buffer is identical to the concentration of that metabolite associated with hSLCs cultured in the presence of one or more known teratogenic compounds. In another embodiment, the method comprises generating a reference profile of the metabolites by method disclosed herein. In yet another embodiment, the method comprises comparing a profile of mass features generated upon exposure of hSLCs to the test compound with the reference profile of metabolites in order to validate the teratogenicity of the test compound.

Advantages of a hSLC Developmental Toxicity Prediction Model

The hSLC-based assay reported herein has several distinct advantages over other standard approaches, namely: 1) Alterations to the metabolites in response to a toxicant is a sensitive and quantitative measurement, which enables more objective data-driven decisions. 2) Multiple biochemical pathways can be assessed simultaneously, which reinforces the robustness of the model when applied to drugs with a variety of mechanisms of toxicity. 3) Metabolic endpoints are a measure of functional biochemical pathways that can be rapidly integrated with protein, DNA, and RNA targets for further pathway-based investigation. 4) Because the prediction is based on multiple independent variables, it is possible to detect teratogens exhibiting complex changes in metabolic patterns. 5) The assay is independent of cell death outcomes and is trained on circulating doses known to cause human developmental toxicity, which increases the probability of finding developmental toxicants that are not just toxic to dividing cells. 6) Testing and analysis is higher throughput, less labor intensive and automatable.

Comparison of hSLC Developmental Toxicity Prediction Model to Other Models

Developmental toxicity testing in cells derived from human embryos is highly likely to generate more reliable in vitro prediction endpoints than those currently available through the use of animal models, or other in vitro non-human assays such as zebra fish models, the EST, and whole embryo culture (WEC) given the physiological relevance of hSLC to human development.

The hSLC model has important biological features in comparison to zebrafish assay systems. First, it is a human system, providing species specificity to predict human outcomes. Zebrafish developmental and biochemical pathways can be quite distinct from those that are critical to human development, for example the absence of placentation and pulmonary differentiation and development, as well as different mechanisms for cardiogenesis. Moreover, the screening throughput of zebrafish assays is somewhat limited due to the high degree of developmental defects associated with small well size (Selderslaghs et al. 2009). The fish are also sensitive to very low concentrations of DMSO, where levels greater than 0.25% cause increased deformities. The determination of a specific defect, by visual inspection of changes in morphology, can also be highly subjective while perturbation to the abundance of small molecule metabolites is a quantitative endpoint measured by a highly sensitive analytical chemistry technique (LC-ESI-QTOF-MS).

TABLE 1

Accuracy of Developmental Toxicity Models

| Model | # Drugs | Accuracy |
|---|---|---|
| Zebra Fish (McGrath 2008) | 12 | 91 |
| devTOX (hSLCs) | 8 | 88 |
| EST (Paquette 2008) | 63 | 83 |
| WEC (Genschow 2002) | 14 | 80 |
| EST (Genschow 2002) | 20 | 78 |
| Zebra Fish Embryos (Chapin 2008) | 18 | 72 |
| MM (Genschow 2002) | 20 | 70 |
| WEC (Genschow 2002) | 14 | 68 |

In comparison to those reported for the EST, which measures cytotoxicity and the ability of chemicals to disrupt proper differentiation of mES cells into cardiomyocytes, the overall reliability of the hSLC assay reported here, based on a metabolic signature of toxicity, was superior to the EST. The EST predictive model is strongly correlated with cytotoxicity, given that two EST variables result from the IC50 concentrations observed in fibroblasts compared to mES cells. These variables make the assumption that developmental toxicants cause cell death at lower concentrations in embryonic cells compared to the "adult" fibroblast cells, which may not be valid for many mechanisms of toxicity (for example—Thalidomide). The dose required to reach an IC50 may also be much higher than the typical circulating dose or that which may be encountered by the fetus in utero leading to large numbers of false positives. It is also likely that changes in cell viability may be observed in vitro which will not occur in vivo.

Further, the hSLC based assay correctly classifies thalidomide as a teratogen while the EST does not (Nieden et al. 2001). The hSLC model is also considerably more predictive than either WEC or micro mass (MM) (Table 1). Further, the hSLC and metabolomics based model offers an opportunity to understand the mechanisms of developmental toxicity in an all human system.

In one embodiment, a virtual library containing all the biomarkers discovered in this study can be established. Such a library provides a repository of human biomarkers useful in assessing developmental toxicity, not only of pharmaceutical agents, but also of other chemicals, the latter subject to increased attention from regulatory directives, namely REACH, in Europe. By integrating a larger number of pharmaceutical compounds in addition to other chemicals that are known to disrupt human development (such as chlorpyrifos, organophosphates, methylmercury) one can further expand the biomarker library and the robustness of metabolomics biomarkers across very diverse collections of chemicals. Although exemplified in a six-well format, metabolomics of hSLCs in a 96-well format are contemplated to enable high-throughput screening of chemical collections such as those available at the Molecular Libraries Program (NIH) or NTP (National Toxicology Program, NIEHS). In addition, a targeted metabolomics approach employing the use of triple quadrupole MS for ultra fast, sensitive and more specific quantitation of metabolites is expected to improve throughput.

The present invention illustrates the ability to utilize hSLCs and metabolomics to provide a predictive, quantitative, all-human in vitro screening method for predicting developmental toxicity of compounds. The model also provides the opportunity to investigate mechanisms of toxicity of compounds by studying the metabolite response of hSLCs exposed to those compounds. Thus, this method has the potential to aid in the prevention of birth defects induced by chemical compounds and to reduce animal testing.

In one embodiment, the present invention provides a more predictive in vitro assay than those currently available in order to further identify biomarkers that are specific to humans, rather than to rodents or other non-human biological systems. Therefore, in one embodiment, the invention provides assays that are more accurate, sensitive, and/or specific than available assays.

In one embodiment, the invention discloses a method for predicting the teratogenicity of a test compound with at least about 80% accuracy, and more particularly with at least about 85% accuracy. In preferred embodiments, the invention discloses a method for predicting the teratogenicity of a test compound with at least about 90% accuracy.

In another embodiment, the invention discloses a method for predicting the teratogenicity of a test compound with at least about 80% sensitivity, more particularly with at least about 85% sensitivity, and even more particularly with at least about 95% sensitivity.

In still another embodiment, the invention discloses a method for predicting the teratogenicity of a test compound with at least about 80% specificity, and more particularly with at least about 85% specificity. In preferred embodiments, the invention discloses a method for predicting the teratogenicity of a test compound with at least about 95% specificity.

In one embodiment, the invention uses a machine learning model to develop a highly accurate, sensitive, and specific assay to determine teratogenicity of test compounds. Accordingly, in one embodiment, the invention provides an initial training set of known teratogenic and non-teratogenic compounds to dose hSLCs. In another embodiment, the invention adds a test compound identified as a teratogen to the initial training set to obtain an expanded training set. In one embodiment, the expanded training set allows for a more accurate, sensitive, and specific model for predicting teratogenicity of test compounds.

In one embodiment, dosing compounds were dosed at concentrations corresponding to their IC50 or EC50 dose levels. In another embodiment dosing compounds were dosed at concentrations corresponding to two doses below their IC50 or EC50 dose levels. In another embodiment, dosing compounds were dosed at concentrations corresponding to their circulating dose. In one aspect, dosing compounds at concentrations corresponding to their circulating dose recapitulates the exposure level to a developing human embryo in vivo and the toxic or teratogenic effect of the dosing compound on human development.

In one embodiment, determination of teratogenicity of a test compound involves comparing the metabolic response of hSLCs cultured in the presence of a test compound with the metabolic response of hSLCs cultured in the absence of the test compound. In another embodiment, determination of teratogenicity of a test compound involves comparing the metabolic response of hSLCs cultured in the presence of a test compound with the metabolic response of hSLCs cultured in the presence of a known non-teratogenic compound. In one aspect, the comparison of metabolic response of hSLCs cultured in the presence of a test compound with the metabolicresponse of hSLCs cultured in the presence of a known non-teratogenic compound allows for a more specific, sensitive, and accurate assay to predict teratogenicity of a test compound. In one embodiment, a non-teratogenic compound is any compound that, upon exposure to hSLCs, does not alter the normal metabolism of hSLCs. Examples of non-teratogenic compounds or agents include, but are not limited to, sugars, fatty acids, spermicides, acetaminophens, prenatal vitamins, and the like.

EXAMPLES

The Examples which follow are illustrative of specific embodiments of the invention, and various uses thereof. They are set forth for explanatory purposes only, and are not to be taken as limiting the invention.

Example 1 hES Cell Culture

WA09 hESCs, obtained from WiCell Research Institute (NIH National Stem Cell Bank, Madison, Wis.) were cultured in 6-well plates on Matrigel (BD Biosciences, San Jose, Calif.), in mTeSR1 medium (Stem Cell Technologies, Vancouver, BC) incubated at 37° C. under 5% $CO_2$ in a Thermo Electron Form a Series II Water Jacket CO2 Incubator. hESCs were passaged every three or four days at a 1:3 or 1:6 seeding density for routine culture conditions. For dosing experiments, hESCs were passaged at a low density of 1:10 or 1:12 so that they would not require passaging during the seven-day dosing protocol. To passage hES cells, the StemPro® EZPassage™ disposable stem cell passaging tool (Invitrogen, Carlsbad, Calif.) was used to detach the cells from the wells. Detached cells were removed with a pipette and distributed to new Matrigel plates.

Example 2 hES Cell Dosing

A training set of established teratogens and non-teratogens (Table 2) was used to dose hESCs. The training set is a collection of chemical standards that includes compounds that had been previously used in multicenter efforts aimed at developing and validating novel alternatives to predict developmental toxicity, such as the EST, proposed by the ECVAM agency.

Figure 1:
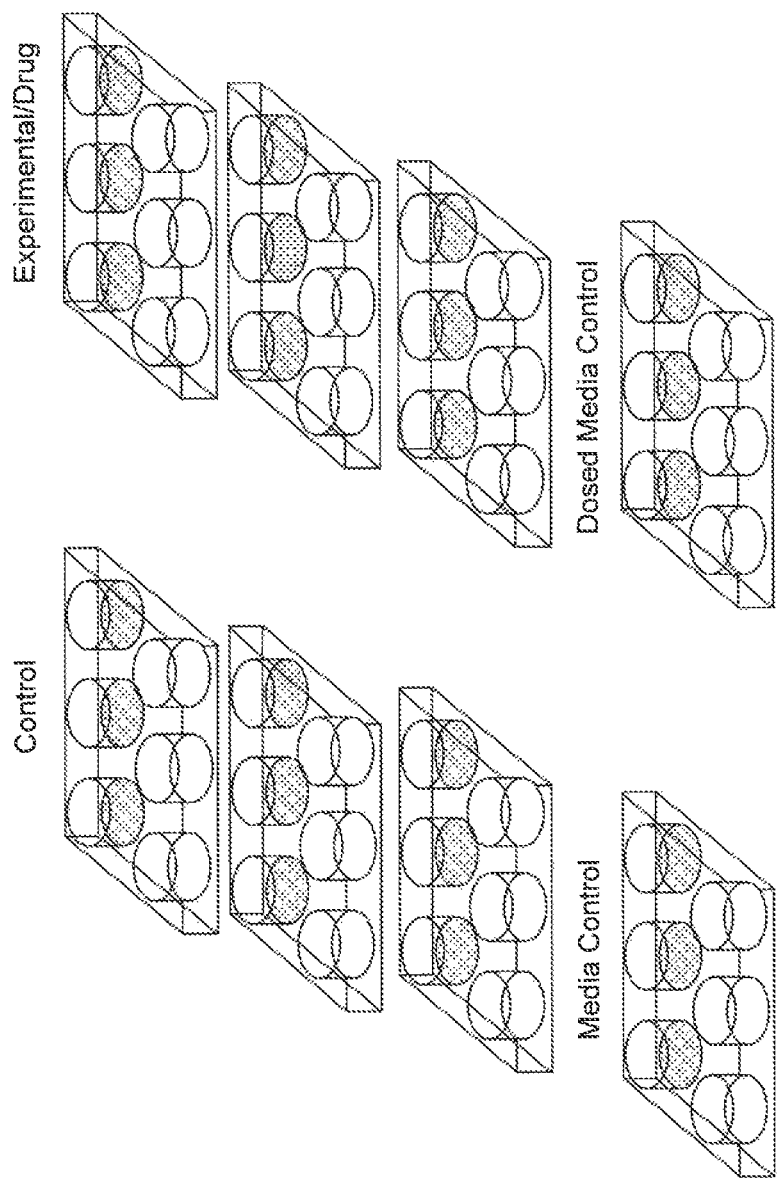

All tested chemicals were purchased from Sigma-Aldrich (St. Louis, Mo.). Cells were dosed with drugs at a concentration equivalent to their published serum circulating therapeutic dosages. Dosing was performed on hESCs in 6-well plates in triplicate, i.e. three wells per plate. The plates were dosed in triplicate, so there were a total of nine dosed wells. In parallel, there were nine "control" wells, in which hESCs were cultured with mTeSR1 containing no drug, and three wells containing Matrigel with mTeSR1 medium without hESCs that served as medium controls. Lastly, three wells of dosed medium controls were prepared, containing Matrigel, mTeSR1 and drug, but no hESCs (FIG. 1). These medium controls provided baseline mass spectral data. On the first day of dosage, the determined concentration of drug was dissolved in mTeSR1, and then 2.5 mL of this solution was added to each dosed well of hESCs. Each day, for four days, the medium was removed and new dosed medium was added. On the fourth day, the medium was removed and added to acetonitrile to make a 40% acetonitrile solution, as outlined in the Sample Preparation section below.

Since it is the goal of the present study to develop a more predictive in vitro assay than those currently available, and to further identify biomarkers that are specific to humans, rather than to rodents or other non-human biological systems, the ECVAM test set was replicated in this study. Additional drugs were included in the training set to increase the number of the non-teratogen chemicals, as well as to supplement the strong teratogens.

TABLE 2

Chemical compounds in the training and test set (blinds) used for dosing, their classification according to teratogenicity and prediction model incorporation. TS1 and TS2 indicate Training Set 1 and 2 respectively.

| Stemina Classification | Compound | Model Training Set | ECVAM Classification |
|---|---|---|---|
| Non-Teratogens | Ascorbic Acid | TS1, 2 | Non-Teratogens |
| | Doxylamine (Blind 2) | TS2 | |
| | Isoniazid | TS1, 2 | |
| | Levothyroxine | TS1, 2 | |
| | Penicillin G | TS1, 2 | |
| | Folic Acid | TS1, 2 | |
| | Retinol (Blind 1) | TS2 | |
| | Thiamine (Blind 8) | TS2 | |
| | Aspirin | TS2 | Weak/Moderate Teratogens |
| | Caffeine | TS2 | |
| | Dexamethasone | | |
| | Diphenhydramine | TS2 | |
| Teratogens | Diphenylhydantoin | TS2 | |
| | Methotrexate | TS2 | |
| | 5-Fluorouracil | TS1, 2 | Strong Teratogens |
| | Accutane (Blind 6) | TS2 | |
| | Amiodarone (Blind 3) | TS2 | |
| | Busulfan | TS1, 2 | |
| | Carbamazepine (Blind 5) | TS2 | |
| | Cyclophosphamide (Blind 7) | TS2 | |
| | Cytosine Arabinoside | TS1, 2 | |
| | Hydroxyurea | TS1, 2 | |
| | Retinoic Acid | TS1, 2 | |
| | Rifampicin (Blind 4) | TS2 | |
| | Thalidomide | TS1, 2 | |
| | Valproic Acid | TS1, 2 | |

Compounds were dosed at concentrations corresponding to their circulating dose rather than IC50 or EC50 dose levels. Dosing was done at the circulating maternal dose as published in the literature in an effort to recapitulate the exposure level to the developing human embryo in vivo and the toxic effect on human development rather than creating a model which measures toxic effect on hESCs in culture. It is noteworthy to mention that the substances employed in this screen (the ECVAM test set) exert their developmental toxicity in a manner that is independent of maternal metabolism.

In other words, this test set was established and employed in multicenter, randomized trials due to the fact that the parent compound, and not reactive metabolites, impair proper human development and are thus suitable to develop novel means for in vitro screening.

Example 3 hES Cell Viability Assays

In addition to determining teratogenicity by molecular endpoints, with metabolomics, cell viability was examined using a subset of the drugs to determine if a correlation exists between cell death and compound teratogenicity. In particular, the viability assay was conducted to address the concern that the metabolic endpoints may be strongly correlated with cell death rather than developmental toxicity since dosing with the antineoplastic drugs cytosine arabinoside and 5-fluorouracil often resulted in the most profound changes in many metabolites.

Cell viability assessment in response to exposure to chemical compounds was examined using the MultiTox-Fluor Assay (Promega, Madison, Wis.), which simultaneously measures cell viability and cytotoxicity. WA09 hESCs were seeded at a density of 250,000 cells/well in a 96-well plate. Cells were fed with dosed media daily, for four days. On the fourth day, spent medium was removed, 100 μL of fresh medium was added along with 100 μL of the MultiTox-Fluor reagent. The plate was incubated at 37° C., 5% $CO_2$ for 30 minutes and measured. The ratios of live to dead cells were normalized to the control cells (no treatment) in order to report relative cell viability.

Figure 2:
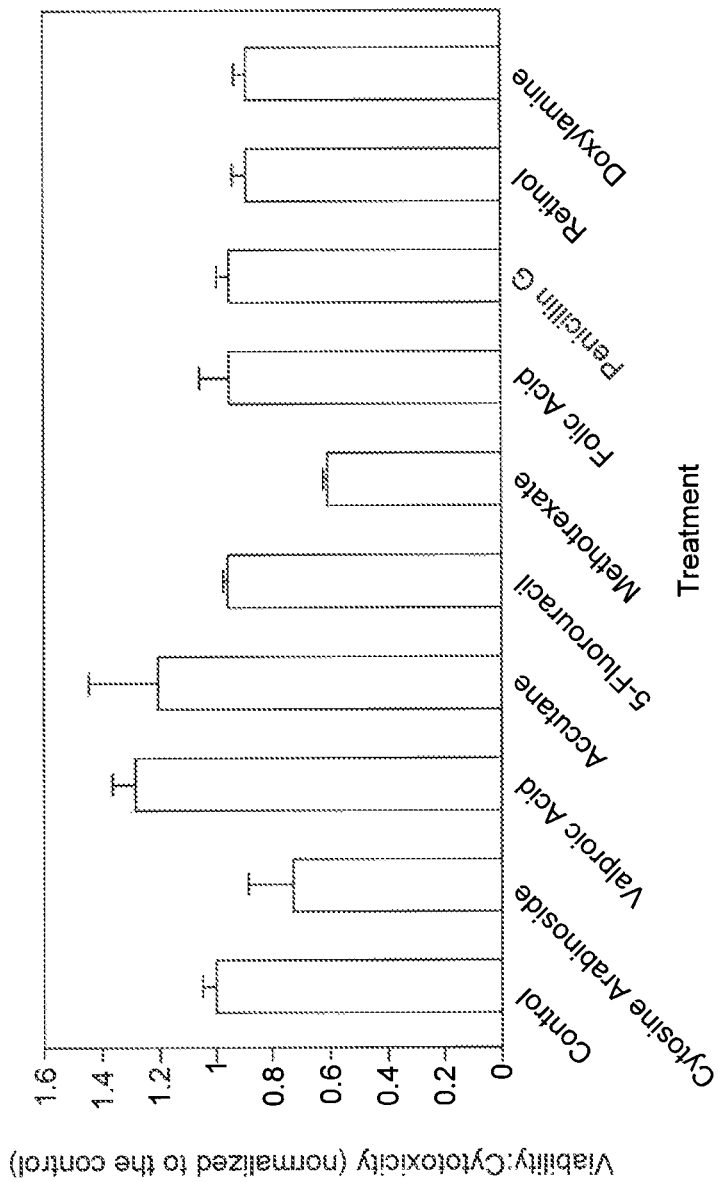

Cell viability data (FIG. 2) showed no discernable correlation between teratogenicity and cell death relative to control cells. Thus, therapeutic concentrations of teratogens are not correlated with cell death in a significant manner, despite the evidence of statistically significant metabolomic changes. This finding suggests that metabolomics has a lower threshold, or increased sensitivity to detect molecular changes associated with developmental toxicity and specific biomarkers in comparison to standard cell death assays, which should provide a more predictive and sensitive screen for developmental toxicity.

Example 4

Developmental Toxicology Screening

Sample Preparation

The 2.5 mL of spent media per well from Example 1 was added to 1.67 mL acetonitrile to make a 40% acetonitrile solution. The acetonitrile acts to "quench" the spent media sample, slowing or halting many metabolic processes and aiding in precipitation of cellular proteins. Samples were either stored at −80° C. for later analysis, or for immediate analysis, 250 μL of the quenched solution was mixed with 250 μL of water, to a final concentration of 20% acetonitrile, then added to a 3 kDa molecular weight cut-off filter spin column (Microcon YM-3 Centrifugal Filter, Millipore, Billerica, Mass.). Each sample was then centrifuged in an IEC CL31R Multispeed Centrifuge (Thermo Scientific, Waltham, Mass.) at 13,000×g at 4° C. for 200 minutes. Following centrifugation, the flow-through was saved then dried for several hours in a Savant High Capacity Speedvac Plus Concentrator. The concentrated sample was then dissolved in 50 μL of 0.1% formic acid prior to LC-MS analysis.

Mass Spectrometry

Mass spectrometry was performed using an Agilent QTOF LC/MS system consisting of a G6520 AA QTOF high resolution mass spectrometer capable of exact mass MS and MS/MS. In order to facilitate separation of small molecules with a wide range of polarity and to allow increased retention of hydrophilic species, Hydrophilic Interaction Liquid Chromatography (Alpert 1990) was employed. Each sample was run for 30 minutes with the gradient shown in Table 3 at a flow rate of 0.5 mL/min, using 0.1% formic acid in water (Solvent A) and 0.1% formic acid in acetonitrile (Solvent B). Electrospray ionization was employed using a dual ESI source, with an Agilent isocratic pump continuously delivering an internal mass reference solution into the source at approx. 0.01 mL/min. The mass range of the instrument was set to 100-1700 Da. A Phenomenex Luna HILIC column with dimensions 3×100 mm 3 μm particle size was used and maintained at 30° C. 5 μL of each sample was injected. Data acquisition was performed with Agilent MassHunter using high-resolution exact mass conditions.

TABLE 3

| | HILIC gradient | |
|---|---|---|
| Time (min) | % A 0.1% formic acid (aq) | % B Acetonitrile with 0.1% formic acid |
| 0.0 | 5 | 95 |
| 1.5 | 5 | 95 |
| 16.0 | 40 | 60 |
| 17.0 | 95 | 5 |
| 21.0 | 95 | 5 |
| 22.0 | 5 | 95 |
| 30.0 | 5 | 95 |

Mass Spectral Data Preprocessing

Following LC-MS, chromatograms were inspected for reproducibility. LC-MS runs with total ion counts that vary by more than 25% were repeated to ensure that samples could be accurately compared. These runs were then used to create mass features that correspond to molecules detected across the different LC-MS runs. Mass features were extracted from the LC-MS data using MassHunter Qualitative Analysis software (Agilent Technologies). The following criteria were used as general guidelines, however some flexibility and optimization was needed. m/z values within the range of 75-1500, with a charge of +1 or −1, and a centroid height greater than 1000 were used to generate "mass features." The mass peaks that pass these criteria were used to fit isotope and adduct ($Na^+$, $K^+$, and $NH4^+$) patterns corresponding to individual molecules, and to establish the abundance of each mass feature. The abundance is calculated by MassHunter software as the sum of the isotopic and adduct peaks that correspond to a single molecular feature. After data deconvolution, mass features showing at least two ions (e.g. $(M^+H)^+$ and $(M^+H)^{+}1$ or $(M^+H)^+$ and $(M^+Na)^+$) and an abundance value greater than 50000 for positive-ion mode data and 10000 in negative-ion mode data were included in the data set used for binning of the mass features.

Following feature selection by MassHunter, the data was further preprocessed by MassProfiler (Agilent) software which aligns mass features across multiple LC-MS data files. Mass features were generated for data from each drug treatment experiment (dosed and control) using the default alignment settings in MassProfiler with the requirement that a feature be present in at least 80% of the samples in one treatment. The mass feature datasets for each drug treatment experiment were further processed in a global manner using custom analysis scripts executed in the R statistical software environment.

Files for each drug experiment were binned using an algorithm based on both exact mass and retention time in order to consider a mass feature the same across different LC/ESI-MS-QTOF runs. The binning criteria is based on both a sliding mass difference scale that allows for larger mass differences at lower molecular weights and a constant retention time window based on the reproducibility of the chromatography. Masses were ordered and considered to be the same feature if a mass under 175 Da differs by less than 18 ppm from the previous mass, while masses 176-300 Da were binned by 12 ppm, and 10 ppm when over 300 Da. These mass bins were ordered by retention time and if a difference in retention of the previous feature was less than twelve seconds it was considered to be the same feature across LC-MS runs. The binning process is used to create unique compound identities (cpdID) that are assumed to represent a single small molecule. If multiple features appeared to fall into the same bin their abundances were averaged.

Determination of Metabolic Flux, Secreted, Excreted, Consumed, or Identified Metabolites The media represents a major factor in the experimental system, in that it contributes many peaks to mass spectra. This can be accounted for in a data dependent manner to select for mass feature bins, which are present at significant levels above the media. Mass feature bins present solely in the presence of cells (not detected in media) or with average abundance levels different than uncultured media were considered to be secreted, excreted, consumed, or identified metabolites.

Validation of Small Molecule Metabolites

In validating the identities of specific metabolites, three criteria were used: 1) The exact mass of the metabolite must be within 10 ppm of the known mass of the compound. 2) The retention time of the metabolite detected in the cell media must be within + or −30 seconds of a reference standard on which MS data had been acquired under the same conditions. The reference standards were dissolved in mTeSR media and prepared in exactly the same manner (described above) as the samples from the cells, including the addition of acetonitrile, Centricon centrifugal filtration, drying then dissolution in formic acid prior to LC-MS analysis. 3) The MS-MS fragmentation spectra of the metabolite detected in the cell media must be a reasonable match with that of the reference standard, including abundances and m/z values of the fragment ions. If published MS-MS spectra are available, the MS-MS spectra must also be a reasonable match.

Example 5

The Random Forest Model

Teratogen Classification for the Random Forest Model

The classification of teratogenicity in previously published animal and cell culture models of developmental toxicity were trained using three different classes, non-teratogens, weak/moderate teratogens, and strong teratogens, based largely on embryotoxicity outcomes and developmental abnormalities observed in animal models (Marx-Stoelting et al. 2009, Chapin et al. 2008). In the present study a modified approach to compound classification since there are many species specific differences in developmental toxicity, focusing the compound teratogenicity classification strictly on observed human risk associated with each chemical.

Thus, the criteria of observed human teratogenicity risk led to a model with two categories of toxicity, teratogen or non-teratogen, which accurately reflects the ultimate intended outcome of the predictive model. This also reduces technical challenges associated with attempting to determine the potency of teratogens based on distantly related species. Additionally, such a focused classification schema (teratogens versus non-teratogens) leads to a more robust and predictive metabolic model of human developmental toxicity given the limited availability of reliable, quantitative data of human risk associated with exposure to weak or moderate teratogens.

Random Forest Modeling

Random Forest (Brieman 2001) was used to create a classification model in order to predict teratogenicity and non-teratogenicity using the median fold change of drug treatment versus its intra-experimental control for each feature (variable) included in the model. Bagging was performed on ⅓ of the samples by re-sampling with replacement 1000 bootstrap subsets from the training set data of known teratogens. Final prediction from the RF classifier on the blinded drugs was based on the majority vote of the ensemble of trees.

Feature Set Used for Random Forest Modeling

The dataset utilized for random forest modeling was a subset of high quality reproducible features. Features were selected if they had values present in at least 75% of the drug treatment experiments (blind and known drugs). This list of features was then filtered against a list of known contaminant molecules such as HEPES and PEG and their numerous adducts to remove features of non-biological interest. Finally, features with poor binning or grouping characteristics were removed.

Feature selection by variable importance was performed by selecting features with a mean decrease in accuracy greater than 0.5. Random forest based analysis was executed using the Random Forest library (Liaw & Wiener 2002). Model metrics were calculated based on the resulting random forest confusion matrix or the predictions of blinded drugs using the methods outlined in (Genschow et al. 2000).

The abundance values were then log base two transformed and the median value of each treatment (dosed and control) within each experiment (different drugs) was used. The data was then normalized by control for each drug treatment experiment. The resulting median log fold change values were used as the input data values for the random forest modeling. Missing median fold change data was replaced with a 0. The remaining positive and negative ESI mode features were combined creating a dataset with 142 features used for modeling.

Example 6

Random Forest Model Results

As discussed in Example 5, random forest model was trained using a filtered dataset consisting of reproducibly measured mass features from both ESI polarities. The median fold change value of a mass feature for the replicates for each drug versus its associated intra-experimental control were used as the variables to predict the teratogenicity of drugs.

The initial training set (TS1) contained 142 mass features resulting from exposure of hESCs to seven teratogens and five non-teratogens (see Table 2).

The detailed annotations for the 142 mass features is provided in Table 4. In comparing the retention times (RT) and mass averages (MASSavg) of each of the mass features with masses recorded in databases such as Kegg, Metlin, HMDB, CAS, PUBCHEMS, PUBCHEMC, CHEBI etc., one will find typically one or more putative candidate metabolites for each mass feature that match the retention times and mass averages. During the subsequent validation process, the identity of the metabolite corresponding to a specific retention time and mass average is determined The metabolite identities validated thus far are also provided in Table 4.

TABLE 4

Feature Table Summary

| newID | ESImode | RT | MASSavg | Metabolite |
|---|---|---|---|---|
| NEGM102T150 | NEG | 150 | 102.0317 | |
| neg11 | neg | 443 | 103.0631 | Gamma-Aminobutyric acid |
| neg12 | neg | 78 | 104.0473 | |
| neg15 | neg | 504 | 105.9670 | |
| NEGM116T150 | NEG | 150 | 116.0110 | |
| NEGM116T90 | NEG | 90 | 116.0110 | Fumaric acid |
| neg71 | neg | 81 | 118.0265 | Succinic acid |
| neg73 | neg | 76 | 118.0626 | Succinic acid |
| neg94 | neg | 655 | 121.0202 | |
| neg101 | neg | 103 | 129.0427 | |
| neg105 | neg | 103 | 129.1420 | |
| neg133 | neg | 75 | 132.0779 | Hydroxyisocaproic acid |
| ESIneg.M132T451 | NEG | 451 | 133.0375 | Aspartic Acid |
| NEGM134T120 | NEG | 120 | 134.0215 | Malic acid |
| neg158 | neg | 71 | 139.0626 | |
| NEGM147T450 | NEG | 450 | 147.0532 | L-Glutamic acid |
| neg198 | neg | 503 | 149.9571 | |
| NEGM155T288 | NEG | 288 | 155.0695 | |
| neg275 | neg | 441 | 169.0339 | |
| neg295 | neg | 320 | 173.0816 | |
| NEGM174T505 | NEG | 505 | 174.1117 | L-Arginine |
| neg360 | neg | 438 | 187.0445 | |
| neg360 | NEG | 445 | 187.0453 | |
| neg414 | neg | 496 | 200.0279 | |
| neg429 | neg | 436 | 203.0548 | |
| neg431 | neg | 80 | 203.1149 | |
| neg435 | neg | 506 | 204.0192 | |
| ESIneg.M215T293 | NEG | 293 | 216.0391 | |
| neg559 | neg | 445 | 231.0737 | |
| neg563 | neg | 73 | 231.9462 | |
| neg622 | neg | 655 | 240.0229 | L-Cystine |
| neg763 | neg | 441 | 260.0964 | |
| neg776 | neg | 655 | 262.0048 | |
| neg779 | neg | 504 | 263.9399 | |
| neg811 | neg | 320 | 267.0687 | |
| neg831 | neg | 435 | 271.0422 | |
| neg840 | neg | 502 | 273.9691 | |
| neg1095 | neg | 73 | 325.9324 | |
| neg1112 | neg | 495 | 328.0276 | |
| neg1121 | neg | 55 | 331.0842 | |
| neg1136 | neg | 90 | 333.1022 | |
| neg1149 | neg | 494 | 336.0678 | |
| neg1167 | neg | 435 | 339.0297 | |
| neg1192 | neg | 493 | 346.0948 | |
| neg1264 | neg | 487 | 360.1113 | |
| neg1366 | neg | 441 | 379.1370 | |
| neg1433 | neg | 448 | 393.1215 | |
| neg1458 | neg | 73 | 401.8984 | |
| neg1491 | neg | 434 | 407.0167 | |
| neg1568 | neg | 82 | 426.0714 | |
| neg1700 | neg | 83 | 453.2425 | |
| neg1728 | neg | 485 | 460.1752 | |
| neg1787 | neg | 434 | 475.0041 | |
| neg1932 | neg | 654 | 502.0281 | |
| neg2068 | neg | 482 | 528.1597 | |
| neg2115 | neg | 434 | 542.9914 | |
| neg2355 | neg | 434 | 610.9786 | |
| neg2606 | neg | 434 | 678.9659 | |
| neg3446 | neg | 88 | 1051.0609 | |
| neg3535 | neg | 73 | 1110.9571 | |
| pos48 | pos | 55 | 103.2278 | |
| pos69 | pos | 661 | 105.9789 | |
| pos102 | pos | 80 | 113.0843 | |
| pos102 | POS | 81 | 113.0844 | |
| pos134 | pos | 345 | 117.0787 | L-Valine |
| pos136 | pos | 54 | 117.1150 | |
| pos213 | pos | 43 | 129.1513 | |
| POSM131T330 | POS | 330 | 131.0946 | L-Isoleucine |
| pos368 | pos | 90 | 150.0898 | PEG (n = 3) |
| POSM155T288 | POS | 288 | 155.0695 | |
| pos422 | pos | 83 | 156.1256 | |
| pos446 | pos | 79 | 158.1412 | |
| pos477 | pos | 439 | 164.0466 | |
| pos518 | pos | 79 | 169.0740 | Pyridoxine |

TABLE 4-continued

Feature Table Summary

| newID | ESImode | RT | MASSavg | Metabolite |
|---|---|---|---|---|
| pos525 | pos | 89 | 170.0574 | |
| pos529 | pos | 72 | 170.1416 | |
| POSM174T505 | POS | 505 | 174.1117 | L-Arginine |
| pos563 | pos | 503 | 174.2275 | |
| pos593 | pos | 44 | 177.1264 | |
| pos625 | pos | 511 | 181.9569 | |
| pos628 | pos | 42 | 182.1780 | |
| pos681 | pos | 133 | 188.1885 | |
| pos687 | pos | 46 | 189.1261 | |
| pos687 | POS | 48 | 189.1264 | |
| pos698 | pos | 441 | 191.0167 | |
| pos744 | pos | 70 | 198.1728 | |
| POSM202T432 | POS | 432 | 202.1430 | Asymmetric Dimethyl-L-arginine |
| pos892 | pos | 88 | 219.1119 | Pantothenic Acid |
| pos917 | pos | 640 | 222.0666 | L-Cystathionine |
| pos922 | pos | 511 | 222.9821 | |
| pos962 | pos | 503 | 227.9989 | |
| pos970 | pos | 43 | 229.2402 | |
| pos1062 | pos | 655 | 240.0245 | |
| pos1084 | pos | 50 | 242.1753 | |
| pos1095 | pos | 96 | 244.0927 | |
| pos1113 | pos | 493 | 246.0704 | |
| ESIpos.M286T667 | POS | 667 | 285.0961 | |
| pos1471 | pos | 98 | 288.1188 | |
| pos1668 | pos | 437 | 312.0289 | |
| pos1684 | pos | 485 | 314.1091 | |
| pos1698 | pos | 42 | 315.2042 | |
| pos1698 | POS | 47 | 315.2050 | |
| pos1734 | pos | 597 | 320.0177 | |
| pos1773 | pos | 484 | 325.5943 | |
| pos1791 | pos | 506 | 328.0611 | |
| pos1820 | pos | 600 | 331.8777 | |
| pos1896 | pos | 495 | 342.1509 | |
| pos1975 | pos | 257 | 354.0566 | Phenol Red |
| pos2019 | pos | 434 | 361.0133 | |
| pos2094 | pos | 483 | 372.1079 | |
| pos2109 | pos | 498 | 374.0676 | |
| pos2178 | pos | 519 | 384.2048 | |
| pos2225 | pos | 438 | 393.0924 | |
| pos2284 | pos | 462 | 401.2065 | |
| pos2288 | pos | 688 | 402.0769 | |
| pos2489 | pos | 258 | 429.9682 | |
| pos2512 | pos | 69 | 434.1609 | |
| pos2527 | pos | 82 | 436.2287 | |
| pos2634 | pos | 83 | 452.2026 | |
| pos2693 | pos | 67 | 462.1915 | |
| pos2763 | pos | 771 | 474.0917 | |
| pos2786 | pos | 81 | 476.2248 | |
| pos2814 | pos | 655 | 478.1241 | |
| pos2823 | pos | 80 | 480.2554 | |
| pos3023 | pos | 495 | 510.1957 | |
| pos3095 | pos | 83 | 524.2812 | |
| pos3183 | pos | 82 | 540.2552 | |
| pos3308 | pos | 82 | 564.2780 | |
| pos3425 | pos | 83 | 584.2815 | |
| pos3627 | pos | 83 | 624.2771 | |
| pos3675 | pos | 77 | 633.3299 | |
| pos3728 | pos | 91 | 640.8206 | |
| pos3777 | pos | 82 | 652.3312 | |
| pos3795 | pos | 492 | 656.2567 | |
| pos3832 | pos | 92 | 662.8337 | |
| pos3871 | pos | 77 | 669.3682 | |
| pos3912 | pos | 625 | 677.2845 | |
| pos3978 | pos | 91 | 692.3328 | |
| pos3980 | pos | 91 | 692.8341 | |
| pos4039 | pos | 93 | 706.3583 | |
| pos4063 | pos | 83 | 712.3292 | |
| pos4079 | pos | 91 | 714.8472 | |
| pos4136 | pos | 93 | 728.3714 | |
| pos4178 | pos | 91 | 736.3593 | |
| pos4208 | pos | 81 | 740.3842 | |
| pos4250 | pos | 91 | 750.3846 | |
| pos4267 | pos | 83 | 756.3554 | |
| pos4283 | pos | 91 | 758.8738 | |
| pos4340 | pos | 91 | 772.3978 | |
| pos4343 | pos | 89 | 772.8994 | |
| pos4371 | pos | 91 | 780.3856 | |
| pos4435 | pos | 90 | 794.4109 | |
| pos4438 | pos | 90 | 794.9130 | |
| pos4513 | pos | 89 | 816.4240 | |
| pos4515 | pos | 90 | 816.9258 | |
| pos4543 | pos | 91 | 824.4121 | |
| pos4559 | pos | 79 | 828.4363 | |
| pos4594 | pos | 90 | 838.4372 | |
| pos4596 | pos | 90 | 838.9392 | |
| pos4617 | pos | 83 | 844.4077 | | newID: Stemina in house name for mass feature. This is a designation for each metabolite/mass feature produced during analysis. It designates a unique feature;
ESImode: electrospray ionization mode feature was detected in;
RT: average retention as measured across ~1000 LC-MS runs of mass feature;
MASSavg: average neutral mass as measured across ~1000 LC-MS runs of mass feature;
Metabolite: identity of the validated metabolite.

These mass features served as the basis for the model that was applied to predict the teratogenicity of chemical compounds in the blind studies and treatments. This model was able to correctly predict the teratogenicity of seven of eight blinded drug treatments, with a specificity of 100% and sensitivity of 80% and overall accuracy of 88% (Table 5).

TABLE 5

Results of the blind study where the teratogenicity was correctly predicted for 7 of 8 drugs using a random forest statistical model.

| Blind # | Drug | Actual | Predicted |
|---|---|---|---|
| B1 | Retinol | Non | Non |
| B2 | Doxylamine | Non | Non |
| B3 | Amiodarone | Ter | Ter |
| B4 | Rifampicin | Ter | Ter |
| B5 | Carbamazepine | Ter | Ter |
| B6 | Accutane | Ter | Non |
| B7 | Cyclophosphamide | Ter | Ter |
| B8 | Vitamin B1 | Non | Non |

Figure 3:
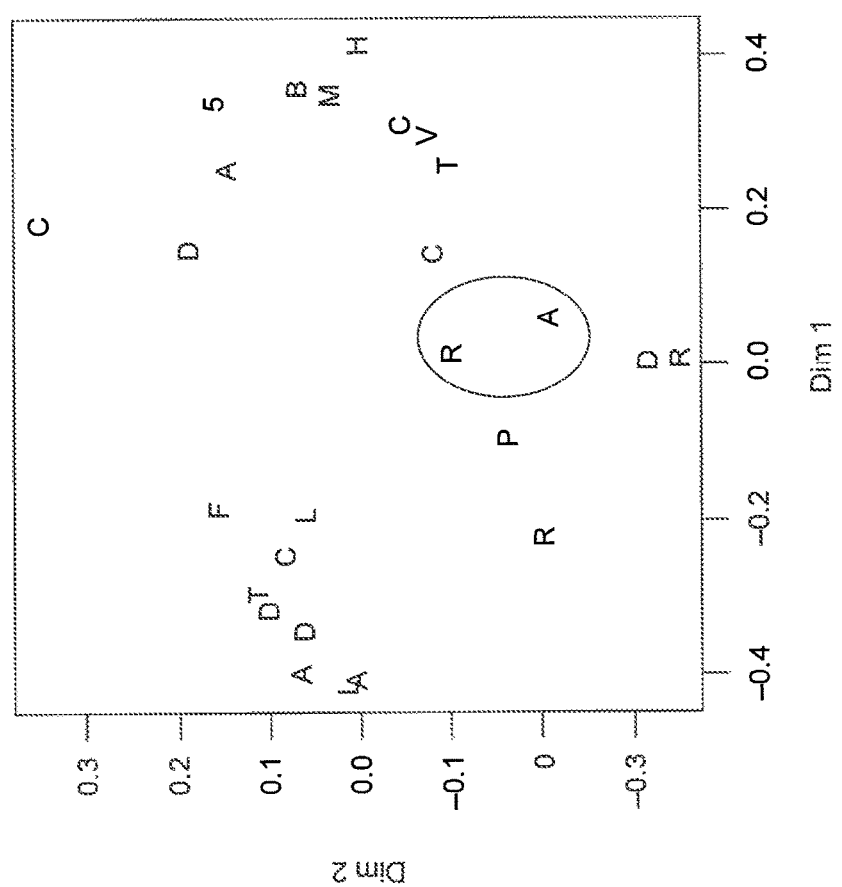

The random forest model was further refined by integrating outcomes from blinded drugs into the model as known classifiers thereby increasing the number of non-teratogens and teratogens in the model, so that the training set consisted of 26 drug treatment experiments. Feature selection based on the variable importance measure mean decrease in accuracy resulted in 18 features that were evaluated as a future predictive model. As a result, the overall accuracy of the model was ultimately increased to 92% (Table 6), i.e. the model was able to correctly predict 24 of the 26 drugs used in the training set. The model was clearly able to differentiate teratogens from non-teratogens into distinct clusters when evaluated by multidimensional scaling (FIG. 3) which reflects clear differences in metabolomics endpoints between treatment classes.

TABLE 6

Model metrics for the 18 feature set prediction model

| | | Accuracy | | |
|---|---|---|---|---|
| Specificity | Sensitivity | Teratogens | Non-Teratogens | Overall |
| 100 | 87 | 87 | 100 | 92 |

Figure 4:
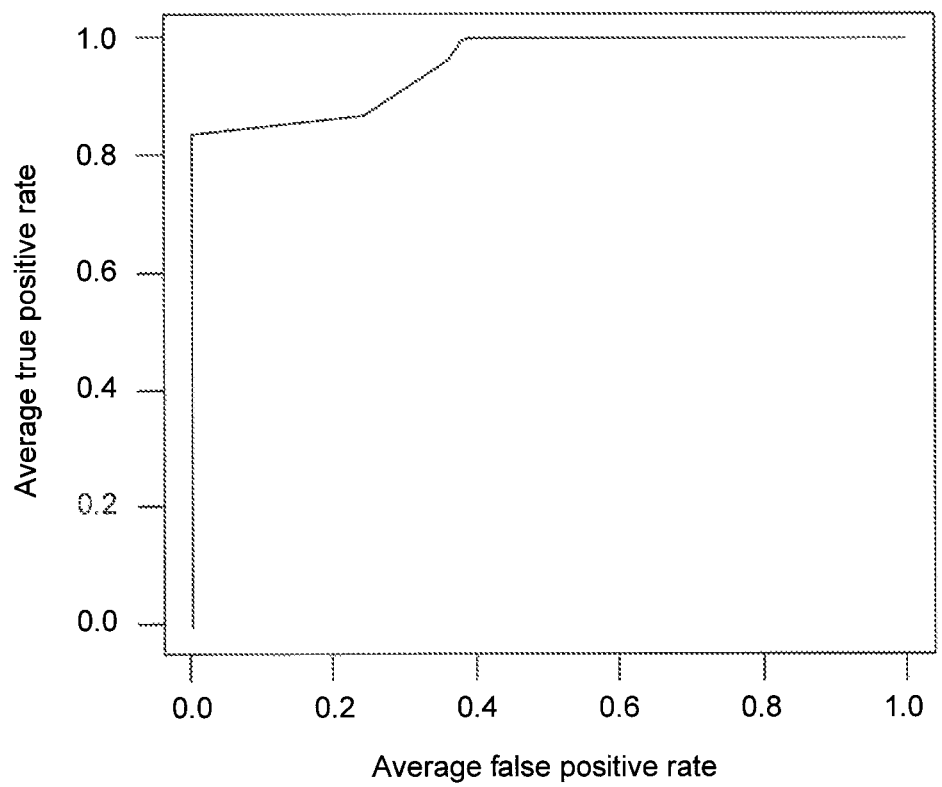

Following prediction of the blinds, a new model was created by incorporating the revealed blinds and more drugs into the training set (TS2, see Table 2). Evaluation of the receiver operating characteristic (ROC) curve of the model's performance demonstrated that the model performs in a robust manner (FIG. 4).

Thus, this model shows superior potential for future prediction of human developmental toxicity in comparison to currently available assays, and that using iterative modeling as more experiments are performed is a powerful benefit to the adoption of meaningful metabolic endpoints in a screen. The predictive ability of this model is subject to continuous monitoring in response to additional blinded drug treatments.

Figure 5:
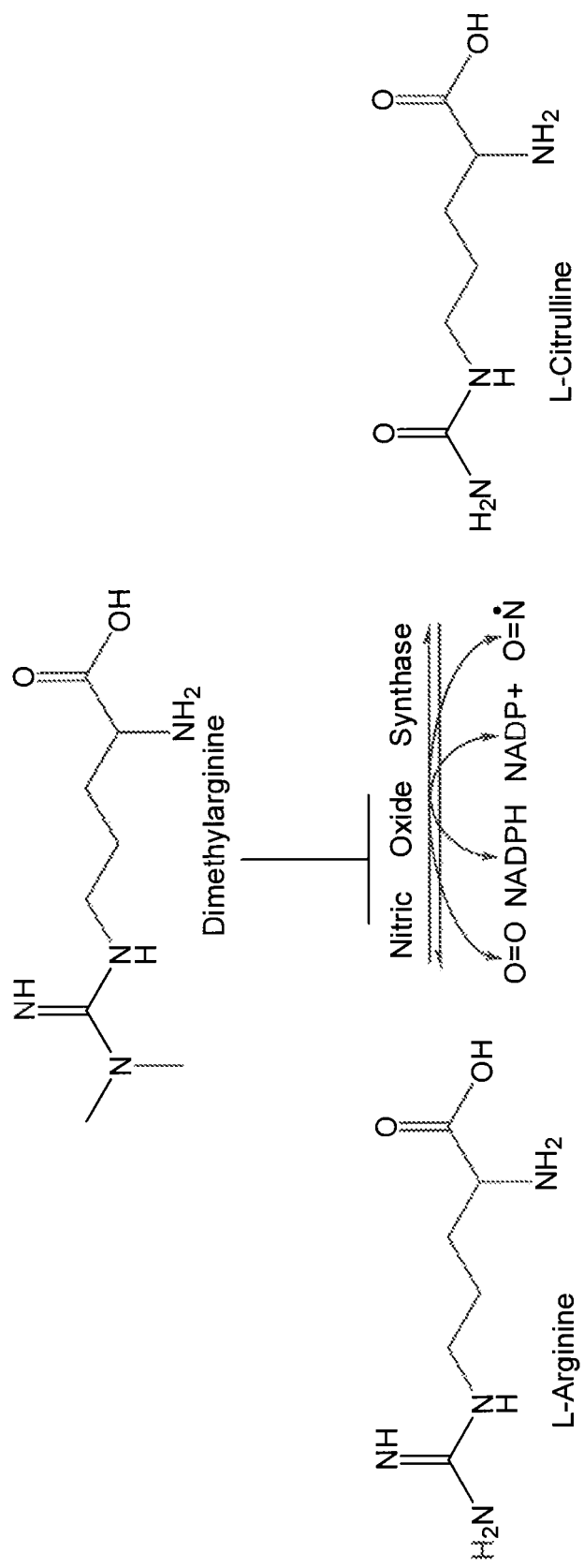

Statistically significant differences in the abundance of specific metabolites were detected in drug-treated and control samples. One such molecule, asymmetric dimethylarginine (ADMA), exhibited a significant fold decrease in its abundance in response to valproic acid treatment exhibiting similar changes for the strong teratogens: cytosine arabinoside, 5-fluorouracil, hydroxyurea, amiodarone and cyclophosphamide. ADMA is an inhibitor of nitric oxide synthase (NOS), an enzyme that converts L-arginine to L-citrulline which is necessary for neural tube closure (FIG. 5).

Valproate is known to cause neural tube defects (DiLiberti et al. 1984) while nitric oxide synthase activity is essential for neural tube closure (Nachmany et al. 2006). The novel alterations in the secretion of dimethylarginine, detected here, suggest that it can be an appropriate candidate biomarker for neural tube defects. Arginine levels were also monitored in our data and usually showed opposite fold changes to those of dimethylarginine in response to several strong teratogens. To quantify the perturbation of arginine and ADMA in the hESCs as a result of dosing, EICs (Extracted Ion Chromatograms) for these compounds were constructed and integrated, then the ratio of the resulting areas for controls vs. dosed were compared. These results indicate that the amount of perturbation may be directly related to the teratogenicity of the dosing compound. There are no false negatives resulting from these metrics, and only ascorbic acid and caffeine are false positives for teratogenicity (Table 7).

TABLE 7

Selected fold change ratios for arginine and dimethylarginine. EICs for these compounds were integrated, then the fold change of the resulting areas for controls vs. dosed were compared. Smaller fold change ratios (between 0.9 and 1.1) show a good correlation with non-teratogens, while greater changes (<0.9 and >1.1) correlate with teratogens. There are no false negatives for teratogenicity resulting from these metrics and only ascorbic acid and caffeine are false positives.

| Stemina Classification | Compound | Arg fold change/ADMA fold change | Arg/ADMA Prediction |
|---|---|---|---|
| Non-Teratogens | Ascorbic Acid | 1.28 | Ter |
| | Aspirin | 1.07 | Non |
| | Caffeine | 1.33 | Ter |
| | Doxylamine (Blind 2) | 0.97 | Non |
| | Isoniazid | 0.94 | Non |
| | Levothyroxine | 1.03 | Non |
| | Penicillin G | 0.96 | Non |
| | Folic Acid | 1.08 | Non |
| | Retinol (Blind 1) | 1.03 | Non |
| | Thiamine (Blind 8) | 1.00 | Non |
| Teratogens | 5-Fluorouracil | 43.93 | Ter |
| | Methotrexate | 2.54 | Ter |
| | Accutane (Blind 6) | 0.55 | Ter |
| | Amiodarone (Blind 3) | 1.64 | Ter |
| | Busulfan | 1.12 | Ter |
| | Carbamazepine (Blind 5) | 1.12 | Ter |

TABLE 7-continued

Selected fold change ratios for arginine and dimethylarginine. EICs for these compounds were integrated, then the fold change of the resulting areas for controls vs. dosed were compared. Smaller fold change ratios (between 0.9 and 1.1) show a good correlation with non-teratogens, while greater changes (<0.9 and >1.1) correlate with teratogens. There are no false negatives for teratogenicity resulting from these metrics and only ascorbic acid and caffeine are false positives.

| Stemina Classification | Compound | Arg fold change/ADMA fold change | Arg/ADMA Prediction |
|---|---|---|---|
| | Cyclophosphamide (Blind 7) | 1.56 | Ter |
| | Cytosine Arabinoside | 67.01 | Ter |
| | Hydroxyurea | 2.52 | Ter |
| | Retinoic Acid | 0.48 | Ter |
| | Rifampicin (Blind 4) | 0.81 | Ter |
| | Thalidomide | 0.85 | Ter |
| | Valproic Acid | 2.11 | Ter |

Figure 6:
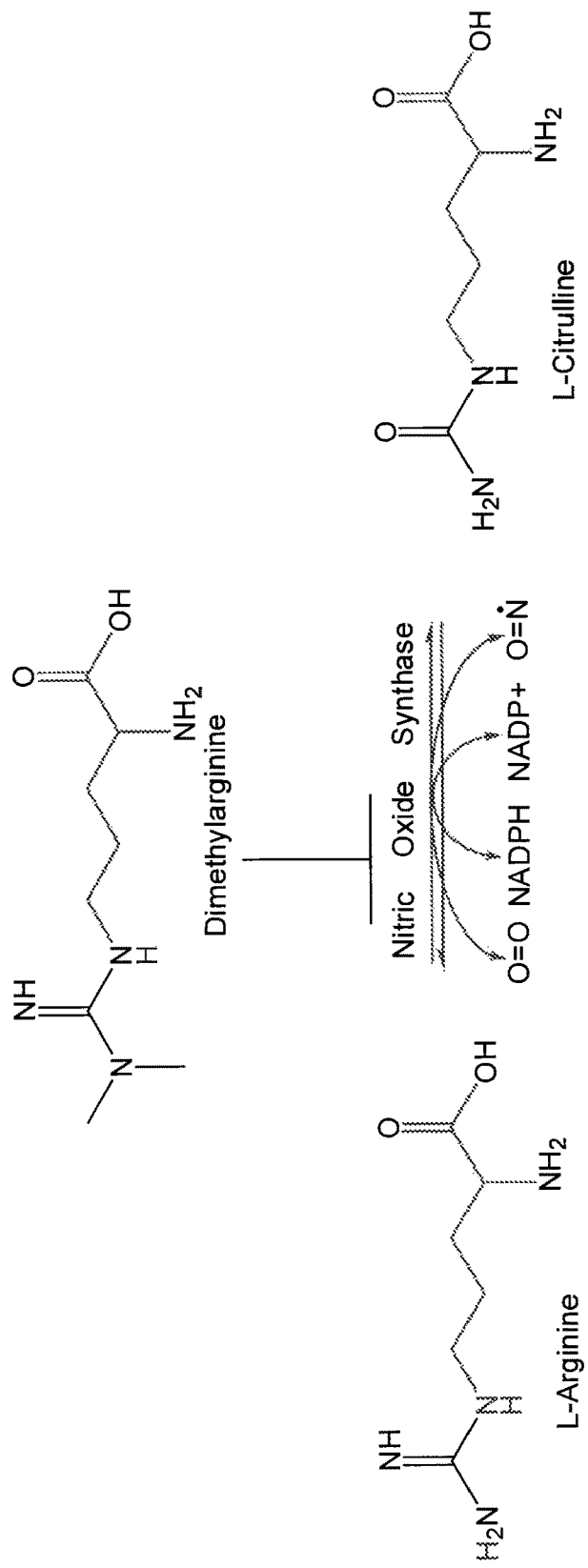
FIG. 6 illustrates the metabolic network relationships between the metabolites found in this study.
Figure 7:
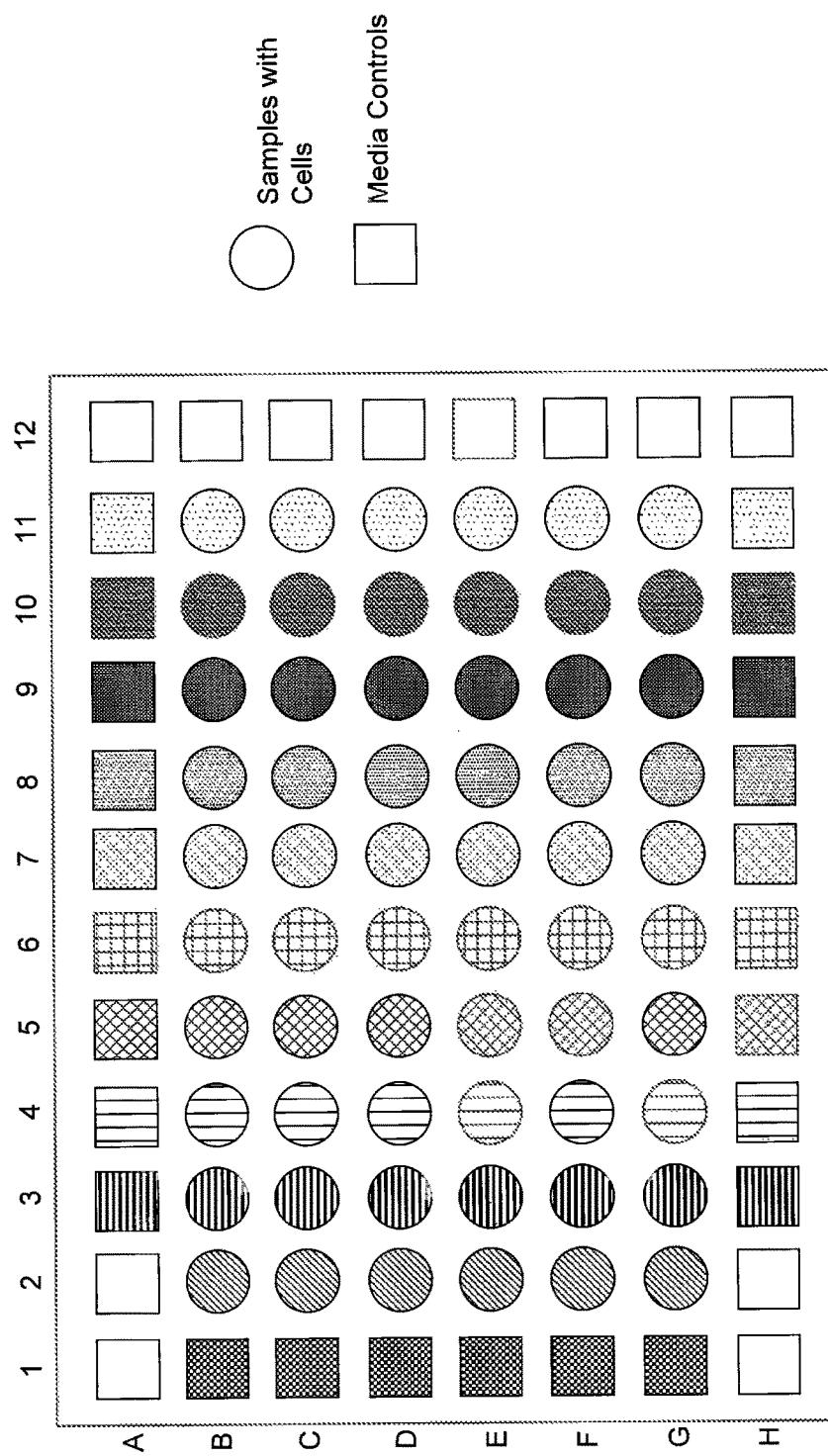
FIG. 7 illustrates the experimental design in 96-well plates for dosing experiments used in the present study.
Figure 8:
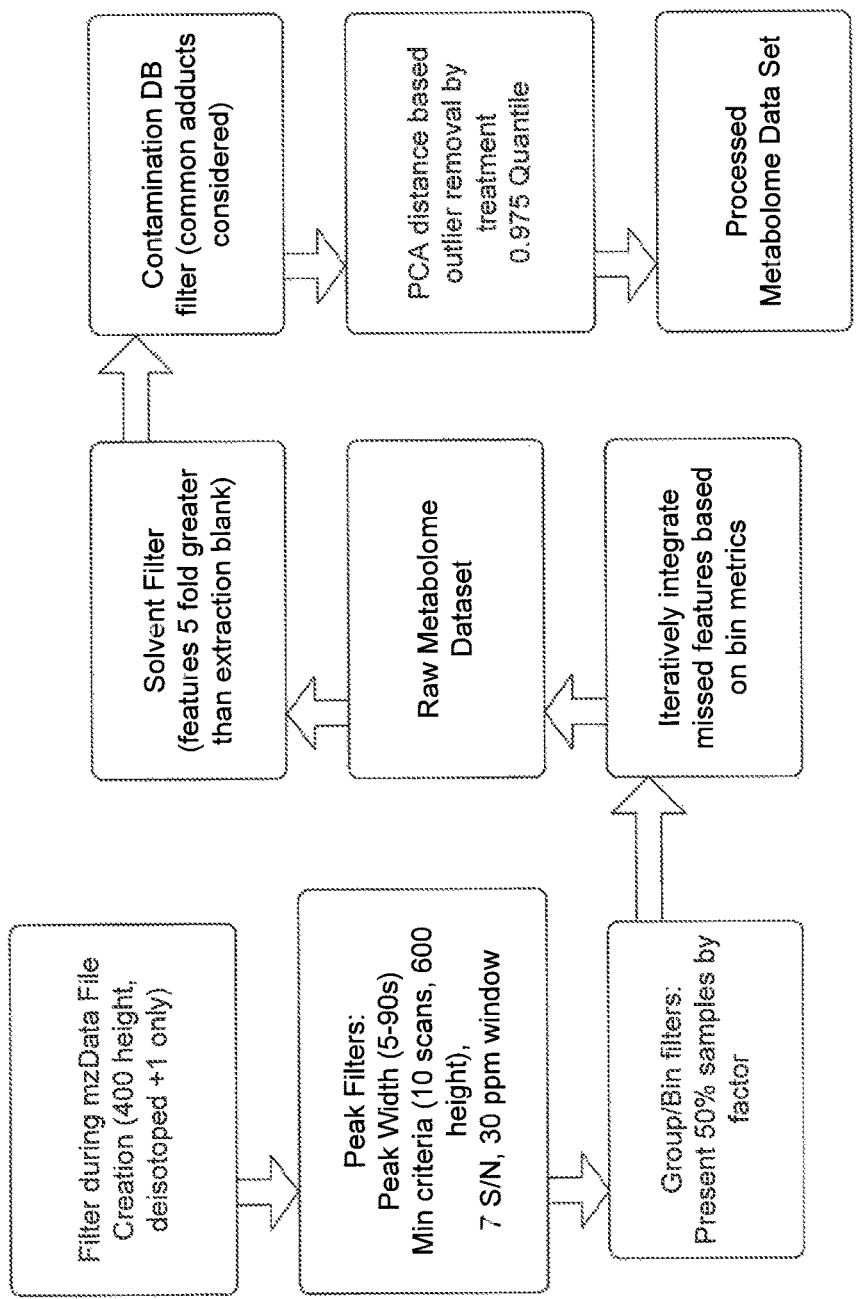
FIG. 8 depicts data preprocessing flow diagram outlier and overview of the filters applied during data processing.
Figure 9:
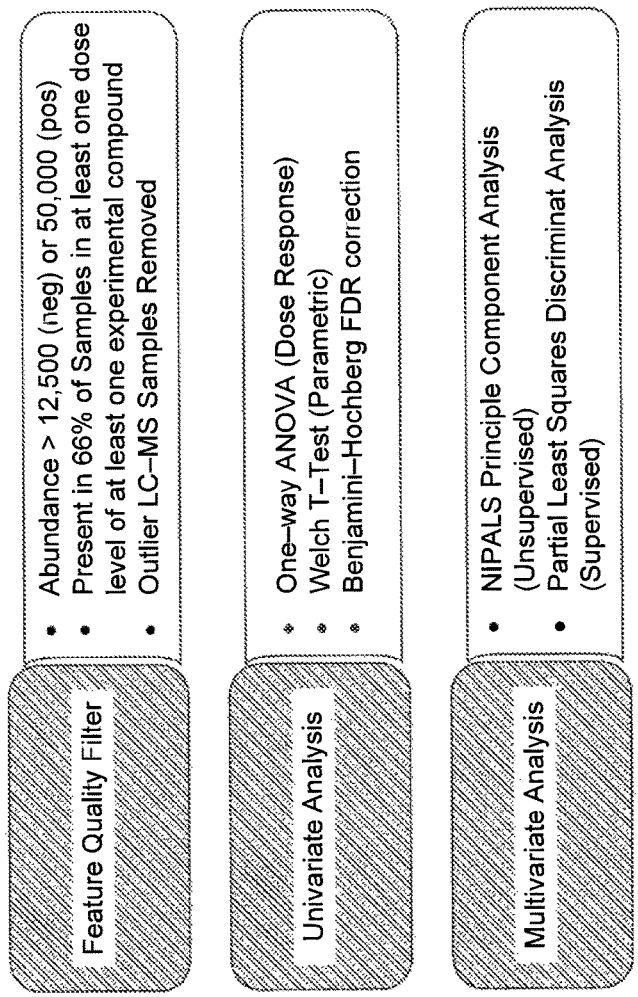
FIG. 9 depicts an overview of the statistical analysis process.

Several metabolites that contributed to the random forest prediction model (PM) were further identified and subject to chemical identity validation by MS-MS. These include succinic acid, which shows significant down regulation in its abundance in response to several teratogens such as carbamazepine, cyclophosphamide, cytosine arabinoside, 5-fluorouracil, hydroxyurea, methotrexate, and valproic acid. Other small molecules that can contribute to the PM are: gamma-aminobutyric acid (GABA), isoleucine, aspartic acid, malic acid, glutamic acid, and histidine. These small molecules were significantly altered, according to the teratogenicity of the test compound and are correlated to each other on the basis of the biochemical pathways where they serve as intermediates. This is illustrated in FIG. 6.

For example, aspartic acid, dimethylarginine, and arginine are components of the urea cycle. This cycle facilitates the removal of dangerous ammonia through conversion of it to urea, which is excreted from the body. Succinic acid, isoleucine, and malate are part of the citric acid cycle, which produces energy for cellular function. Both networks are linked by glutamate and GABA, which in turn has a critical role in neuronal physiology.

Certain reactions in the urea cycle take place in the mitochondria, while the Kreb's cycle is active in the mitochondria in its entirety. Perturbations to the urea cycle can result in excess ammonia, which, among a vast array of pathological effects, has been correlated to newborn deaths (Summar 2001). Interruption of citric acid cycle reactions compromises cellular energy metabolism with direct detrimental effects to cellular viability.

Increased concentrations of GABA were detected in the secretome of hESCs dosed with busulfan, among other teratogens. Dysfunctions in GABA, underlie well established neurological disorders such as epilepsy, language delay, and neurodevelopmental impairment, among others (Pearl & Bigson 2004). The neurodevelopmental toxicity of busulfan has been previously reported in humans; specifically in utero exposure to busulfan led to a spinal birth defect due to insufficient neural fold development, although the mechanism was not defined (Abramovici et al. 2005).

Example 7

Mechanistic Pathways of Developmental Toxicity

Altogether, metabolomics of hESCs detected statistically significant alterations to multiple small molecule metabolites which play a key role in cellular physiology and human development. Several of these candidate biomarkers were further validated by MS-MS mass spectrometry in order to confirm their chemical identity. Significantly, despite the unsupervised nature of the analysis, many of these significant and validated small molecule metabolites participate in pathways that had been previously suggested to underlie developmental toxicity albeit not in cells derived from human embryos. A list of validated small molecules and the metabolic networks they map to is provided in Table 8.

TABLE 8

Small Molecules and Metabolic Networks.

| Name | Formula | Mass | METLIN compound ID | KEGG compound ID | HMDB compound ID | CAS compound ID | PUBCHEM Compound ID | CHEBI Compound ID | KEGG Pathway ID | Metabolic Network or (Function) |
|---|---|---|---|---|---|---|---|---|---|---|
| 2-Hydroxyethanesulfonate (isethionate) (sometimes misspelled as isothionate) | C2H6O4S | 125.9987 | 6987 | C05123 | HMDB03903 | 107-36-8 | 7866 | | hsa00430 | Taurine and hypotaurine metabolism |
| Cysteic acid (cysteate) | C3H7NO5S | 169.0045 | 332 | C00506 | HMDB02757 | 13100-82-8 | 25701 | 17285 | hsa00270 | Cysteine and methionine metabolism |
| | | | | | | | | | hsa00430 | Taurine and hypotaurine metabolism |
| | | | | | | | | | hsa04080 | Neuroactive ligand-receptor interaction |
| L-Cystathionine | C7H14N2O4S | 222.0674 | 39 | C02291 | HMDB00099 | 56-88-2 | 439258 | 17482 | hsa00260 | Glycine, serine and threonine metabolism |
| | | | | | | | | | hsa00270 | Cysteine and methionine metabolism |
| N1-Acetylspermidine | C9H21N3O | 187.1685 | 3323 | C00612 | HMDB01276 | 34450-16-3 | 496 | 17927 | | (cell growth and differentiation) |
| Glycerophosphocholine | C8H21NO6P | 258.1106 | 370 | C00670 | HMDB00086 | 28319-77-9 | 439285 | 16870 | hsa00564 | Glycerophospholipid metabolism |
| | | | | | | | | | hsa00565 | Ether lipid metabolism |
| Spermine | C10H26N4 | 202.2157 | 255 | C00750 | HMDB01256 | 71-44-3 | 1103 | 15746 | hsa00330 | Arginine and proline metabolism |
| | | | | | | | | | hsa00410 | beta-Alanine metabolism |
| | | | | | | | | | hsa00480 | Glutathione metabolism |
| Spermidine | C7H19N3 | 145.1579 | 254 | C00315 | HMDB01257 | 124-20-9 | 1102 | 16610 | hsa00330 | Arginine and proline metabolism |
| | | | | | | | | | hsa00410 | beta-Alanine metabolism |
| | | | | | | | | | hsa00480 | Glutathione metabolism |
| 1-Methylnicotinamide | C7H9N2O | 137.0715 | 274 | C02918 | HMDB00699 | 3106-60-3 | 457 | 16797 | hsa02010 | ABC transporters |
| | | | | | | | | | hsa00760 | Nicotinate and nicotinamide metabolism |
| Nicotinamide | C6H6N2O | 122.048 | 1497 | C00153 | HMDB01406 | 98-92-0 | 936 | 17154 | hsa00760 | Nicotinate and nicotinamide metabolism |

TABLE 8-continued

Small Molecules and Metabolic Networks.

| Name | Formula | Mass | METLIN compound ID | KEGG compound ID | HMDB compound ID | CAS compound ID | PUBCHEM Compound ID | CHEBI Compound ID | KEGG Pathway ID | Metabolic Network or (Function) |
|---|---|---|---|---|---|---|---|---|---|---|
| L-Acetylcarnitine | C9H18NO4 | 204.1236 | 956 | C02571 | HMDB00201 | 3040-38-8 | 18230 | 15960 | | (facilitates movement of acetyl CoA into the matrices of mammalian mitochondria) |
| Serotonin | C10H12N2O | 176.095 | 74 | C00780 | HMDB00259 | 50-67-9 | 5202 | 28790 | hsa00380 | Tryptophan metabolism |
| | | | | | | | | | hsa04080 | Neuroactive ligand-receptor interaction |
| | | | | | | | | | hsa04540 | Gap junction |
| Melatonin | C13H16N2O2 | 232.1212 | 73 | C01598 | HMDB01389 | 73-31-4 | 896 | 16796 | hsa00380 | Tryptophan metabolism |
| | | | | | | | | | hsa04080 | Neuroactive ligand-receptor interaction |
| Glutathione | C10H17N3O6S | 307.0838 | 44 | C00051 | HMDB00125 | 70-18-8 | 124886 | 16856 | hsa00270 | Cysteine and methionine metabolism |
| | | | | | | | | | hsa00480 | Glutathione metabolism |
| L-Malic acid | C4H6O5 | 134.0215 | 118 | C00149 | HMDB00156 | 97-67-6 | 222656 | 30797 | hsa00020 | Citrate cycle (TCA cycle) |
| | | | | | | | | | hsa00620 | Pyruvate metabolism |
| | | | | | | | | | hsa00630 | Glyoxylate and dicarboxylate metabolism |
| | | | | | | | | | hsa05200 | Pathways in cancer |
| | | | | | | | | | hsa05211 | Renal cell carcinoma |
| Maleic acid | C4H4O4 | 116.011 | 4198 | C01384 | HMDB00176 | 110-16-7 | 444266 | 18300 | hsa00650 | Butanoate metabolism |
| | | | | | | | | | hsa00760 | Nicotinate and nicotinamide metabolism |
| Pyridoxine | C8H11NO3 | 169.0739 | 2202 | C00314 | HMDB00239 | 65-23-6 | 1054 | 16709 | hsa00750 | Vitamin B6 metabolism |
| L-Histidine | C6H9N3O2 | 155.0695 | 21 | C00135 | HMDB00177 | 71-00-1 | 6274 | 15971 | hsa00340 | Histidine metabolism |
| | | | | | | | | | hsa00410 | beta-Alanine metabolism |
| | | | | | | | | | hsa00970 | Aminoacyl-tRNA biosynthesis |
| | | | | | | | | | hsa02010 | ABC transporters |
| Succinic acid | C4H6O4 | 118.0266 | 114 | C00042 | HMDB00254 | 110-15-6 | 1110 | 15741 | hsa00020 | Citrate cycle (TCA cycle) |
| | | | | | | | | | hsa00190 | Oxidative phosphorylation |

TABLE 8-continued

Small Molecules and Metabolic Networks.

| Name | Formula | Mass | METLIN compound ID | KEGG compound ID | HMDB compound ID | CAS compound ID | PUBCHEM Compound ID | CHEBI Compound ID | KEGG Pathway ID | Metabolic Network or (Function) |
|---|---|---|---|---|---|---|---|---|---|---|
| | | | | | | | | | hsa00250 | Alanine, aspartate and glutamate metabolism |
| | | | | | | | | | hsa00350 | Tyrosine metabolism |
| | | | | | | | | | hsa00360 | Phenylalanine metabolism |
| | | | | | | | | | hsa00630 | Glyoxylate and dicarboxylate metabolism |
| | | | | | | | | | hsa00640 | Propanoate metabolism |
| | | | | | | | | | hsa00650 | Butanoate metabolism |
| L-Arginine | C6H14N4O2 | 174.1117 | 13 | C00062 | HMDB00517 | 74-79-3 | 6322 | 16467 | hsa00330 | Arginine and proline metabolism |
| | | | | | | | | | hsa00472 | D-Arginine and D-ornithine metabolism |
| | | | | | | | | | hsa00970 | Aminoacyl-tRNA biosynthesis |
| | | | | | | | | | hsa02010 | ABC transporters |
| | | | | | | | | | hsa05014 | Amyotrophic lateral sclerosis (ALS) |
| Asymmetric Dimethyl-L-arginine | C8H18N4O2 | 202.143 | 6309 | C03626 | HMDB01539 | 102783-24-4 | 123831 | 17929 | | (Inhibitor of Nitric Oxide Synthase in Arginine and proline metabolism) |
| L-Cystine | C6H12N2O4S2 | 240.0239 | 17 | C00491 | HMDB00192 | | | | hsa00270 | Cysteine and methionine metabolism |
| L-Isoleucine | C6H13NO2 | 131.0946 | 23 | C00407 | HMDB00172 | 73-32-5 | 791 | 17191 | hsa02010 | ABC transporters |
| | | | | | | | | | hsa00280 | Valine, leucine and isoleucine degradation |
| | | | | | | | | | hsa00290 | Valine, leucine and isoleucine biosynthesis |
| | | | | | | | | | hsa00970 | Aminoacyl-tRNA biosynthesis |
| Aspartic Acid | C4H7NO4 | 133.0375 | 15 | C00049 | HMDB00191 | 56-84-8 | 5960 | 17053 | hsa02010 | ABC transporters |
| | | | | | | | | | hsa00250 | Alanine, aspartate and glutamate metabolism |
| | | | | | | | | | hsa00260 | Glycine, serine and threonine metabolism |

TABLE 8-continued

Small Molecules and Metabolic Networks.

| Name | Formula | Mass | METLIN compound ID | KEGG compound ID | HMDB compound ID | CAS compound ID | PUBCHEM Compound ID | CHEBI Compound ID | KEGG Pathway ID | Metabolic Network or (Function) |
|---|---|---|---|---|---|---|---|---|---|---|
| | | | | | | | | | hsa00270 | Cysteine and methionine metabolism |
| | | | | | | | | | hsa00300 | Lysine biosynthesis |
| | | | | | | | | | hsa00330 | Arginine and proline metabolism |
| | | | | | | | | | hsa00340 | Histidine metabolism |
| | | | | | | | | | hsa00410 | beta-Alanine metabolism |
| | | | | | | | | | hsa00460 | Cyanoamino acid metabolism |
| | | | | | | | | | hsa00760 | Nicotinate and nicotinamide metabolism |
| | | | | | | | | | hsa00770 | Pantothenate and CoA biosynthesis |
| | | | | | | | | | hsa00910 | Nitrogen metabolism |
| | | | | | | | | | hsa00970 | Aminoacyl-tRNA biosynthesis |
| | | | | | | | | | hsa02010 | ABC transporters |
| | | | | | | | | | hsa04080 | Neuroactive ligand-receptor interaction |
| Gamma-Aminobutyric acid (GABA) | C4H9NO2 | 103.0633 | 279 | C00334 | HMDB00112 | 56-12-2 | 119 | 16865 | hsa00250 | Alanine, aspartate and glutamate metabolism |
| | | | | | | | | | hsa00330 | Arginine and proline metabolism |
| | | | | | | | | | hsa00410 | beta-Alanine metabolism |
| | | | | | | | | | hsa00650 | Butanoate metabolism |
| | | | | | | | | | hsa04080 | Neuroactive ligand-receptor interaction |
| Mevalonic acid | C6H12O4 | 148.0736 | 127 | C00418 | HMDB00227 | 150-97-0 | 439230 | 17710 | hsa00900 | Terpenoid backbone biosynthesis |
| 2-deoxyuridine | C9H12N2O5 | 228.0746 | 91 | C00526 | HMDB00012 | 951-78-0 | 13712 | 16450 | hsa00240 | Pyrimidine metabolism |

As discussed under Example 6, ADMA, an inhibitor of Nitric oxide (NO) metabolism, exhibited significant increases in fold changes in response to exposure of hESCs to strong teratogens. NO has been identified as a candidate mechanism for neural tube disorders, and NO is essential for normal axial development (Alexander et al. 2007). Monomethyl-L arginine, a specific inhibitor of NO, demonstrated NO is so critical for mammalian development, that both an excess as well as deficiency of NO can be embryotoxic (Lee & Juchau 2005). The present study is the first time that two human intermediates in this network, arginine and dimethylarginine (FIG. 5, Table 7) were measured and exhibited statistically significant changes in response to several known disruptors of human development.

Other key small molecules changed as reported in the results section, share the same chemical network, namely GABA and glutamic acid. GABA is the principal inhibitory neurotransmitter in the brain. Glutamate dysregulation has the potential to severely compromise neurogenesis, possibly contributing to cell death in specific regions of the brain (reviewed in (Bauman 1998)). Specifically, glutamate is vital for programmed cell death from development until three years of age. Not only does the metabolite glutamate regulate neuronal survival or death, but it also plays a critical role in cognition, learning and memory (Tashiro et al. 2006). Glutamate and GABA are also known modulators of neuronal migration during development (Lujan et al. 2005); hence concomitant dysregulation of glutamate and GABA metabolism can provide an important mechanism for human developmental toxicity.

Surprisingly, other small molecules reported herein, such as succinic acid, are likely to play synergistic roles with glutamic acid and GABA in the mechanism of teratogen-induced toxicity, given that simultaneous changes to rate-limiting enzymes in both networks (GABA-transaminase and succinic semialdehyde dehydrogenase) are present in certain neuropsychiatric disorders, such as succinic semialdehyde dehydrogenase deficiency or GABA aciduria (reviewed in (Pearl et al. 2007)). Although this syndrome is inherited, in contrast to the environmental nature of developmental toxicity, it becomes even more striking that valproate has been shown to aggravate symptoms in these patients, through further detriment to GABA and succinic acid metabolism (Shinka et al. 2003), which is a direct indication of the potential of this hESC-based developmental toxicity screen to elucidate biologically meaningful mechanisms of compound toxicity.

The metabolomics results presented here suggest that busulfan affects GABA levels in the developing embryo, which in turn can underlie neural developmental disruption. These examples illustrate how metabolomics unravels mechanistic networks of developmental toxicity through direct analysis of secreted or excreted metabolites from hESCs dosed with known teratogens. In doing so, it is quite possible to model the potential for developmental toxicity of new drugs screened in preclinical development with a high degree of predictability while providing information about the mechanisms of toxicity. Further studies will allow classification of compounds into subgroups of developmental toxicity such neural developmental disruptors or those likely to cause structural malformations.

In one embodiment five or more of the validated small molecules listed in Table 8 are used to predict the teratogenicity of a test compound according to the methods of the present invention. In other embodiments, ten or more of the validated small molecules listed in Table 8 are used to predict the teratogenicity of a test compound according to the methods of the present invention.

Example 8

Metabolic Networks Involved in Developmental Toxicity

Two experimental systems were deployed per chemical: viability studies and metabolomics studies. These assays were performed in two phases. Cell viability assays were performed to establish the three concentrations to dose hES cells for metabolomic studies. First, hES cells were dosed with eight concentrations of each then cell viability measurements were made using the MultiTox-Fluor cell based assay (Promega). Concentration curves for each chemical were calculated to determine the three concentrations for the metabolomics analysis. The final concentrations employed in this study were those that caused no cell death and minimal cell death, if possible.

For metabolomic analysis, hES cells were dosed at the three concentrations for each chemical compound based on the cell viability data. Media controls (no cells), dosed media controls (no cells with dosed media), and controls (cells with undosed media) were also included in the experimental design (FIG. 1). Spent media was collected following a three day dosing period. The collected media was immediately quenched in acetonitrile then stored at −80° C. until later analysis.

In both the viability and metabolomics steps, 96-well plates were seeded with 250,000 cells/well of WA09 hES cells. These cells were "dosed" for three days. Each day for three days, the spent media was removed and replaced with mTeSR®1 media containing the designated compound. Each compound stock solution was made in DMSO and each final solution used to dose hES cells contained 0.1% DMSO. Spent media samples were collected on the fourth day and prepared for metabolomic analysis.

Sample Preparation:

In order to isolate small molecular weight compounds (<10 kDa) from samples for metabolomics experimentation, the Millipore Multiscreen Ultracel-10 molecular weight cut off plates were used. These plates were first washed with a 0.1% sodium hydroxide solution and then twice with water to remove contaminant polymer product. The quenched sample were added to the washed filter which was centrifuged at 2000×g for approximately 240 minutes at 4° C., the flowthrough was collected, then dried overnight in a Speed-Vac. The dried samples were reconstituted in 70 µL, of 1:1 0.1% formic acid in water:0.1% formic acid in acetonitrile and transferred to a 96-well plate.

LC-MS Experiment:

Samples were analyzed in both ESI positive and ESI negative modes on an Agilent QTOF instrument, operated in high resolution, extended dynamic range mode. Two Phenomenex Luna HILIC columns; 100×3 mm; P/N 00D-4449-Y0, S/N 440333-5, and S/N 512570-3 were used for the analysis.

Data Processing:
Sample Naming Scheme

Sample names used for statistical analysis are coded with the experimental compound name (ST003G.74.A, ST003G.75.B, etc.), the dose level (High (H), Medium (M), or Low (L)), and repetitions (a-h). The sample name "ST003G.74.A _H_b" can be decoded as experimental compound 74A, dose level "high," repetition b and the sample name "ST003G.84.K_L_b" can be decoded as experimental compound 84K, dose level "low," repetition b and so on.

Data Processing mzData File Creation

Agilent raw data files were converted to the open source mzData file format using Agilent MassHunter Qual software version 3.0. During the conversion process, deisotoping (+1 charge state only) was performed on the centroid data and peaks with an absolute height less than 400 (approximately double the typical average instrument background level). The resulting mzData files contain centroid data of deisotoped (+1 charge state only) peaks that have an absolute height greater than 400 counts.

Mass Feature Creation and Integration.

Peak picking and feature creation were performed using the open source software library XCMS. Mass features (peaks) were detected using the centwave algorithm. Following peak picking deviations in retention times were corrected using the obiwarp algorithm that is based on a non-linear clustering approach to align LC-MS samples. Mass feature bins or groups were generated using a density based grouping algorithm. After the data had been grouped into mass features, missing features were integrated based on retention time and mass range of a feature bin using the iterative peak filling. Feature intensity is based on the Mexican hat integration values of the feature extracted ion chromatograms.

Solvent/Extraction Blank Filter

The extraction blank filter removes ions associated with the sample extraction process and background ions present in the LC-MS system. Features were removed from the metabolomics dataset if the average in the experimental samples was less than five times the average abundance in the extraction blanks.

Contamination DB Filter

The contamination DB filter removes features with a mass match within 20 ppm to entries in Stemina's proprietary database which contains a number of contaminants such as plasticizers and PEG compounds identified in previous studies. Features are removed without respect to retention time if they match a contaminant or a common charge specific adduct of a contaminant.

PCA Based Outlier Removal

Sample outlier detection and removal is performed on the log based 2 transformed pareto scaled abundance values by experimental factor use NIPALS based PCA. A distance measurement is used to flag and remove outlier LC-MS samples that are outside the 0.975 quantile of the distance measurements.

Abundance and Reproducibility Filter

Prior to statistical analysis, features were filtered by factor (e.g. experimental compound by dose) to remove features that did not exhibit abundance greater than 12,500 (ESI negative mode) or 50,000 (ESI positive mode) in 66% of the LC-MS runs for at least one dose level (L, M, H) of at least one experimental compound (e.g., ST003G.82.I). This filter selects against spurious low abundance features at the level of detection that are not reproducibly measured, and features that may not have peak shapes amenable to reproducible detection and/or integration. This filter typically removes a large portion of the metabolomics dataset, and focuses the analysis on the most reliable and valuable features. For example a feature with abundance values greater than 12,500 in 70% of the negative mode LC-MS samples in one dose level of one experimental compound and abundance values greater than 12,500 in none of the other experimental compound by dose combinations would pass the filter because at least one experimental compound by dose factor satisfies the filter criteria.

Data Transformation and Normalization.

All data were log base two transformed. Normalization for each factor level was performed by subtracting the column (sample) mean and dividing by the row (feature) standard deviation for each value (autoscaling).

Differential Analysis of Mass Features (Univariate)

Mass features were evaluated under the null hypothesis that no difference is present between the means of experimental classes and the alternative hypothesis that there is a difference between experimental classes. Welch two sample T-tests were performed as a parametric method that does not assume equal variances of the experimental classes. A one-way ANOVA was performed on each experimental compound to evaluate the difference in means across the three dose levels. Tukeys post hoc tests were performed to identify significant differences between the dose levels. Following statistical analysis false discovery rates were controlled for multiple testing using the Benjamini-Hochberg (1995) method of p value correction of the ANOVA and Welch T-tests.

Analysis of Mass Features (Multivariate)

Annotation of mass features was carried out by comparing the m/z mass values of the mass features to Stemina's internal metabolite database containing records from multiple public databases such as HMDB, KEGG, PubChem Compound, and METLIN and company-specific metabolite data. The features were annotated with respect to the appropriate adducts for each ESI mode. The identities of all mass features were not validated and therefore all annotations are putative.

Identification of Mass Features

Annotation of mass features was carried out by comparing the m/z mass values of the mass features to Stemina's internal metabolite database containing records from multiple public databases such as HMDB, KEGG, PubChem Compound, and METLIN and company-specific metabolite data. The features were annotated with respect to the appropriate adducts for each ESI mode. The identities of all mass features were not validated and therefore all annotations are putative.

Networks Analysis

Pathways enrichment analysis was performed by mapping annotated mass features for each experimental compound to human metabolic networks using KEGG compound ids. Hypergeometric p-values and false discovery rates (FDR) were used to assign a quantitative measure of statistical significance to each network. Features derived from ESI negative and positive mode for each experimental compound were pooled for this analysis. False positive results can be generated by isobaric compounds that generate multiple "hits" in a pathway from the same mass, so unique masses instead of unique compound ids were used for these calculations. The relevant parameters used to calculate hypergeometric p-values for each pathway were: the number of unique mass "hits", the number of unique masses in the network, and the total number of unique masses in all of the human networks in the KEGG database. For each experimental compound, the p-values for the derived networks were converted to FDR using the Benjamini and Hochberg (1995) correction.

Selection of Interesting Features

Feature Selection was performed on a per compound basis using a one-way anova evaluating the difference of dose level means and on a per dose basis using Welch T-tests and PLS-DA VIP score. Features were selected for further evaluation if they had a Welch FDR<0.05 or a PLS-DA VIP score>20 with at least a 50% fold change and control cells showed at least a 40% difference to control media (secreted, consumed, or identified), or Anova FDR<0.05 and a difference between 0.1× and 10× dose was at least 50%. If a feature was selected as interesting in a drug or dose level comparison it was then evaluated experiment wide for fold changes. Following feature selection only significant features putatively annotated as mammalian in origin and present on KEGG network diagrams were further evaluated. Pathway enrich analysis was then performed on the selected features and features in networks exhibiting a statistically significant enrichment were further evaluated for fold changes. These selection criteria focused the analysis on biochemical pathways.

Results and Discussion:

Metabolomic analysis of the cell culture supernatant extracts resulted in a set of 324 features in ESI positive mode and 307 features in ESI negative mode after selection for statistical significance and putative mammalian annotations. Following selection, features were passed through a quality control evaluation of extracted ion chromatograms (EICs) to confirm the validity of individual mass features. Features passing quality control were further evaluated to confirm estimated fold changes. After removing poor quality and duplicate features, the remaining ESI positive and ESI negative mode features were combined into a unified dataset for evaluation of pathway enrichment by treatment. These mass features mapped to 86 different KEGG networks of which 15 exhibited a statistically significant (FDR<0.1) enrichment of annotated features in at least one treatment (Table 9). EICs for all metabolites in 4 networks that exhibited the most significant enrichment were plotted and feature quality and fold changes were evaluated.

Changes in metabolites associated with the urea cycle, glutamate metabolism, and the citric acid cycle have been associated with exposure of hES cells to teratogens. Several of the annotated mass features were evaluated for changes in at least two dose levels (unless otherwise noted) of the blinded compounds. Succinic acid (TCA cycle) is generally decreased in hES cells treated with teratogens and unchanged in non-teratogens. In this study, succinic acid was decreased in at least two dose levels in cells treated with ST003G.74.A, ST003G.75.B, ST003G.76.C, ST003G.77.D, ST003G.80.G, ST003G.81.H. Treatment with teratogens leads to a decrease in accumulation of dimethylarginine (DMA, urea cycle) usually observed in combination with increases in arginine (arginine and proline metabolism) secreted by hES cells. In the current study, blinded compounds exhibited increased secretion of DMA in ST003G.82.I, ST003G.83.J, ST003G.84.K and ST003G.85.L, a mixed response in ST003G.77.D and ST003G.78.E, and decreased accumulation in ST003G.80.G while arginine was not significantly changed in this study. Glutamic Acid (glutamate metabolism) exhibited increased secretion in ST003G.74.A and ST003G.84.K, a mixed response in ST003G.78 E and ST003G.80.G following treatment while hES cells following treatment with teratogens show a pattern of either increased or decreased levels of glutamic acid. γ-Aminobutyric acid (GABA, neuroactive ligand-receptor) which can be increased in hES after treatment with teratogens was increased in ST003G.84.K and decreased in ST003G.75.B. Aspartic acid (urea cycle, glutamate metabolism) is generally increased in the media of hES cells following treatment with teratogens was decreased in ST003G.74.A and ST003G.75.B and increased in ST003G.77.D and ST003G.80.G. Malic acid, which is generally changed in teratogens in a more extreme manner than non-teratogens exhibited extreme fold changes in the high dose levels of ST003G.78.E, ST003G.79.F, ST003G.80.G, ST003G. 82.I, and ST003G.85.L.

TABLE 9

Summary of pathway enrichment analysis performed on positive and negative features. The values indicate the number of unique KEGG ID annotations identified across dose levels for each drug. Cells having underlined values indicate a statistically significant enrichment (FDR < 0.1) in at least one treatment dose level.

| Pathway Description | 74.A | 75.B | 76.C | 77.D | 78.E | 79.F | 80.G | 81.H | 82.I | 83.J | 84.K | 85.L |
|---|---|---|---|---|---|---|---|---|---|---|---|---|
| Alanine, aspartate and glutamate metabolism | 0 | 0 | 0 | 0 | 1 | 1 | 4 | 0 | 7 | 0 | 0 | 1 |
| Arginine and proline metabolism | 1 | 0 | 2 | 3 | 2 | 0 | 6 | 0 | 15 | 0 | 1 | 1 |
| Ascorbate and aldarate metabolism | 0 | 0 | 1 | 4 | 1 | 0 | 2 | 0 | 11 | 5 | 0 | 2 |
| Citrate cycle (TCA cycle) | 0 | 0 | 0 | 1 | 2 | 0 | 2 | 0 | 5 | 0 | 0 | 1 |
| Cysteine and methionine metabolism | 0 | 0 | 0 | 0 | 0 | 0 | 4 | 0 | 8 | 0 | 0 | 2 |
| Galactose metabolism | 0 | 0 | 0 | 6 | 0 | 0 | <u>0</u> | 0 | 13 | 9 | 0 | 2 |
| Glutathione metabolism | 0 | 0 | 1 | 3 | <u>1</u> | 1 | 4 | 0 | 3 | 0 | 0 | 1 |
| Glyoxylate and dicarboxylate metabolism | 0 | 0 | 0 | 1 | <u>3</u> | 0 | 2 | 1 | 6 | 0 | 0 | 3 |
| Nicotinate and nicotinamide metabolism | 0 | 0 | 1 | 0 | 5 | 0 | 1 | 0 | <u>6</u> | 0 | 0 | 5 |
| Pantothenate and CoA biosynthesis | 0 | 0 | 1 | 1 | 3 | 0 | 1 | 0 | 5 | 0 | 0 | 3 |
| Pentose and glucuronate interconversions | 0 | 0 | 0 | 0 | 1 | 1 | 1 | 0 | 13 | 1 | 0 | 3 |

TABLE 9-continued

Summary of pathway enrichment analysis performed on positive and negative features. The values indicate the number of unique KEGG ID annotations identified across dose levels for each drug. Cells having underlined values indicate a statistically significant enrichment (FDR < 0.1) in at least one treatment dose level.

| Pathway Description | 74.A | 75.B | 76.C | 77.D | 78.E | 79.F | 80.G | 81.H | 82.I | 83.J | 84.K | 85.L |
|---|---|---|---|---|---|---|---|---|---|---|---|---|
| Pentose phosphate pathway | 0 | 0 | 0 | 3 | 0 | 1 | <u>1</u> | 0 | 6 | 4 | 0 | 1 |
| Propanoate metabolism | 0 | 0 | 1 | 0 | 1 | 0 | 7 | 0 | 5 | 0 | 0 | 3 |
| Pyruvate metabolism | 0 | 0 | 0 | 1 | 1 | 0 | 1 | 0 | <u>8</u> | 0 | 0 | 6 |
| Vitamin B6 metabolism | 0 | 0 | 0 | 0 | 0 | 1 | 2 | 0 | <u>6</u> | 1 | 0 | 3 |

Example 9

Prediction of Teratogenicity of Test Compounds

The potential teratogenicity of the individual compounds analyzed in Example 8 were further validated.

Data Analysis and Results:

Prediction of teratogenicity was performed using a partial least squares discriminate analysis (PLS-DA) model based on metabolic changes observed in the spent cell culture media (secretome) from WA09 human embryonic stem (hES) cells treated with pharmaceutical agents. The PLS-DA classifier model was trained on data previously acquired in the DevTox project for the secretome of hES cells that had been treated with therapeutic circulating doses of 22 pharmaceutical agents of known teratogenicity (Table 11). These included 11 known teratogens and 11 known non-teratogens. The current model is based on the mean fold change (treatment versus its associated intra-experimental control) of 15 metabolites common among the secretome of hES cells treated with pharmaceutical agents and unknown chemical compounds. The results of this model for the DevTox drugs are shown in Table 11. For this study of EPA compounds, the experiment represents the first instance of this PLS-DA model as applied to the prediction of non-pharmaceutical environmental toxicants.

TABLE 10

Features utilized in the PLS-DA prediction of Teratogenicity. Metabolites in bold font indicate a previously validated metabolite.

| Annotation | m/z | RT | Polarity |
|---|---|---|---|
| methylsulfonylacetonitrile | 120.0116 | 618 | ESI(+) |
| Aspartic Acid | 134.0460 | 431 | ESI(+) |
| N*-Acetylspermidine | 188.1760 | 431 | ESI(+) |
| Dimethyl-L-arginine | 203.1504 | 445 | ESI(+) |
| Unknown | 215.1387 | 466 | ESI(+) |
| L-Cystathionine | 223.0750 | 593 | ESI(+) |
| Unknown | 234.8904 | 246 | ESI(+) |
| Unknown | 251.0666 | 105 | ESI(+) |
| Unknown | 403.0839 | 653 | ESI(+) |
| GABA | 102.0561 | 467 | ESI(−) |
| Fumaric acid | 115.0057 | 111 | ESI(−) |
| Valine | 116.0712 | 309 | ESI(−) |
| Succinic acid | 117.0190 | 82 | ESI(−) |
| Aspartic acid | 132.0299 | 472 | ESI(−) |
| Pantoic acid | 147.0658 | 81 | ESI(−) |

TABLE 11

Prediction of teratogencity by PLS-DA-DevTox pharmaceutical compounds that were utilized in the PLS-DA Model and their resulting predictions. The high (H = 10x) and low (L = 0.1x) dose treatments of the pharmaceutical agents utilized in the training set are included as a reference (Note: M = 1x, corresponds to the circulating dose. This dose was used in the training of the PLS-DA model and hence omitted from prediction table). Bold font indicates non-teratogen at circulating dose, regular font indicates teratogen at circulating dose.

| Drug Treatment | Prediction | % Non | % Ter | Confidence |
|---|---|---|---|---|
| 5-Fluorouracil_H | Ter | 0.32 | 0.68 | 0.36 |
| 5-Fluorouracil_L | Ter | 0.28 | 0.72 | 0.44 |
| Accutane_H | Ter | 0.3 | 0.7 | 0.4 |
| Accutane_L | Ter | 0.33 | 0.67 | 0.34 |
| Busulfan_H | Ter | 0.28 | 0.72 | 0.44 |
| Busulfan_L | Ter | 0.29 | 0.71 | 0.42 |
| Carbamazepine_H | Ter | 0.37 | 0.63 | 0.26 |
| Carbamazepine_L | Non | 0.5 | 0.5 | 0 |
| Cyclophosphamide_H | Ter | 0.45 | 0.55 | 0.1 |
| Cyclophosphamide_L | Ter | 0.41 | 0.59 | 0.18 |
| CytosineArabinoside_H | Ter | 0.36 | 0.64 | 0.28 |
| CytosineArabinoside_L | Ter | 0.33 | 0.67 | 0.34 |
| Hydroxyurea_H | Ter | 0.32 | 0.68 | 0.36 |
| Hydroxyurea_L | Non | 0.64 | 0.36 | 0.28 |
| Methotrexate_H | Ter | 0.42 | 0.58 | 0.16 |
| Methotrexate_L | Ter | 0.48 | 0.52 | 0.04 |
| RetinoicAcid_H | Ter | 0.3 | 0.7 | 0.4 |
| RetinoicAcid_L | Ter | 0.3 | 0.7 | 0.4 |
| Rifampicin_H | Ter | 0.27 | 0.73 | 0.46 |
| Rifampicin_L | Ter | 0.46 | 0.54 | 0.08 |
| Thalidomide_H | Ter | 0.3 | 0.7 | 0.4 |
| Thalidomide_L | Non | 0.65 | 0.35 | 0.3 |
| VPA_H | Ter | 0.34 | 0.66 | 0.32 |
| VPA_L | Ter | 0.43 | 0.57 | 0.14 |
| Ascorbic Acid_H | Non | 0.57 | 0.43 | 0.14 |
| Ascorbic Acid_L | Non | 0.57 | 0.43 | 0.14 |
| Caffeine_H | Non | 0.53 | 0.47 | 0.06 |
| Caffeine_L | Non | 0.58 | 0.42 | 0.16 |
| Diphenhydramine_H | Non | 0.73 | 0.27 | 0.46 |
| Diphenhydramine_L | Non | 0.76 | 0.24 | 0.52 |
| Doxylamine_H | Ter | 0.38 | 0.62 | 0.24 |
| Doxylamine_L | Non | 0.58 | 0.42 | 0.16 |
| Folic Acid_H | Non | 0.59 | 0.41 | 0.18 |
| Folic Acid_L | Non | 0.59 | 0.41 | 0.18 |
| Isoniazid_H | Non | 0.59 | 0.41 | 0.18 |
| Isoniazid_L | Non | 0.76 | 0.24 | 0.52 |
| Levothyroxine_H | Non | 0.59 | 0.41 | 0.18 |
| Levothyroxine_L | Non | 0.69 | 0.31 | 0.38 |
| PenicillinG_H | Non | 0.57 | 0.43 | 0.14 |
| PenicillinG_L | Non | 0.55 | 0.45 | 0.1 |
| Retinol_H | Non | 0.65 | 0.35 | 0.3 |
| Retinol_L | Non | 0.75 | 0.25 | 0.5 |
| Saccharin_H | Non | 0.8 | 0.2 | 0.6 |
| Saccharin_L | Non | 0.75 | 0.25 | 0.5 |
| Thiamine_H | Non | 0.78 | 0.22 | 0.56 |
| Thiamine_L | Non | 0.82 | 0.18 | 0.64 |

TABLE 12

Prediction of teratogencity by PLS-DA for EPA compounds. % Non and % Ter are the PLS-DA generated class probabilities. Confidence is the difference between class probabilities. Confidence values less than 0.1 are considered inconclusive with respect to the class prediction.

| Treatment | Prediction | % Non | % Ter | Confidence |
|---|---|---|---|---|
| ST003G.74.A_H | Ter | 0.35 | 0.65 | 0.3 |
| ST003G.74.A_M | Ter | 0.44 | 0.56 | 0.12 |
| ST003G.74.A_L | Non | 0.59 | 0.41 | 0.18 |
| ST003G.75.B_H | Ter | 0.49 | 0.51 | 0.02 |
| ST003G.75.B_M | Non | 0.65 | 0.35 | 0.3 |
| ST003G.75.B_L | Ter | 0.4 | 0.6 | 0.2 |
| ST003G.76.C_H | Ter | 0.42 | 0.58 | 0.16 |
| ST003G.76.C_M | Non | 0.64 | 0.36 | 0.28 |
| ST003G.76.C_L | Non | 0.75 | 0.25 | 0.5 |
| ST003G.77.D_H | Ter | 0.39 | 0.61 | 0.22 |
| ST003G.77.D_M | Ter | 0.38 | 0.62 | 0.24 |
| ST003G.77.D_L | Ter | 0.37 | 0.63 | 0.26 |
| ST003G.78.E_H | Non | 0.69 | 0.31 | 0.38 |
| ST003G.78.E_M | Non | 0.64 | 0.36 | 0.28 |
| ST003G.78.E_L | Non | 0.59 | 0.41 | 0.18 |
| ST003G.79.F_H | Ter | 0.37 | 0.63 | 0.26 |
| ST003G.79.F_M | Non | 0.51 | 0.49 | 0.02 |
| ST003G.79.F_L | Ter | 0.45 | 0.55 | 0.1 |
| ST003G.80.G_H | Non | 0.59 | 0.41 | 0.18 |
| ST003G.80.G_M | Non | 0.63 | 0.37 | 0.26 |
| ST003G.80.G_L | Non | 0.66 | 0.34 | 0.32 |
| ST003G.81.H_H | Non | 0.67 | 0.33 | 0.34 |
| ST003G.81.H_M | Non | 0.69 | 0.31 | 0.38 |
| ST003G.81.H_L | Non | 0.75 | 0.25 | 0.5 |
| ST003G.82.I_H | Ter | 0.3 | 0.7 | 0.4 |
| ST003G.82.I_M | Ter | 0.42 | 0.58 | 0.16 |
| ST003G.82.I_L | Non | 0.57 | 0.43 | 0.14 |
| ST003G.83.J_H | Non | 0.73 | 0.27 | 0.46 |
| ST003G.83.J_M | Non | 0.75 | 0.25 | 0.5 |
| ST003G.83.J_L | Non | 0.75 | 0.25 | 0.5 |
| ST003G.84.K_H | Non | 0.73 | 0.27 | 0.46 |
| ST003G.84.K_M | Non | 0.79 | 0.21 | 0.58 |
| ST003G.84.K_L | Non | 0.81 | 0.19 | 0.62 |
| ST003G.85.L_H | Ter | 0.45 | 0.55 | 0.1 |
| ST003G.85.L_M | Ter | 0.44 | 0.56 | 0.12 |
| ST003G.85.L_L | Ter | 0.41 | 0.59 | 0.18 |

Conclusions:

The prediction model that has been developed classifies the EPA-provided chemical agents ST003G.74.A, ST003G.75.B, ST003G.77.D, ST003G.82.I, ST003G.85.L as potential teratogens, and the chemical agents ST003G.76.C, ST003G.78.E, ST003G.80.G, ST003G.81.H, ST003G.83.J, ST003G.84.K as potential non-teratogens. The chemical agent ST003G.76.0 is predicted as a teratogen only at the highest dose level. See Table 12.

Doxylamine was added to the test set as a reference pharmaceutical treatment (ST003G-85-L). Doxylamine has been ranked by the FDA as a pregnancy category B drug, which means that animal studies show no risk of that particular drug inducing birth defects and there are no studies in pregnant women. This compound was analyzed in the developmental toxicity assay. At the low and medium dose, Doxylamine was classified as a non-teratogen, while at the high concentration; it was classified as a teratogen (Table 11). In these studies all three concentrations (low, medium, and high) of Doxylamine was classified as being a teratogen. The concentrations of Doxylamine used in these studies and the corresponding teratogenicities assigned at each concentration are shown in the table below. There appears to be a critical concentration which causes the classification of Doxylamine to switch from a non-teratogen to a teratogen and, according to our data, it is between 0.38 and 1 µM.

TABLE 13

Doxylamine dose levels and PLS-DA teratogenocity predictions.

| [Doxylamine] (µm) | Project | Teratogenicity Classification |
|---|---|---|
| 0.038 | devTox low | Non |
| 0.38 | devTox medium | Non |
| 1 | EPA low | Ter |
| 3.8 | devTox high | Ter |
| 10 | EPA medium | Ter |
| 100 | EPA high | Ter |

To ensure the teratogenicity classifications are not merely a reflection of cell viability, the cell viability data was analyzed (FIG. 23). As indicated below, there is no correlation between teratogenicity classification and cell viability, and at 1 µM Doxylamine the cells are actually thriving (FIGS. 23, a to c). There is some cell death at 0.38 µM, however, at this concentration, Doxylamine was still not classified as a teratogen. This example of the prediction on the teratogenicity of Doxylamine helps substantiate the present model of teratogenicity.

Example 10

Pathway Interpretation

Several biochemical pathways with a statistically significant enrichment of annotated mass features were further evaluated. Of most interest in the present findings are nicotinate and nicotinamide metabolism, pantothenate and CoA biosynthesis, glutathione metabolism, and arginine and proline metabolic networks. These pathways were examined to elucidate connections between these pathways and birth defects. Metabolites within the pathways which are marked with a black circle are those with unique masses while those which are marked with a grey circle are isobaric and may be another metabolite with the same molecular weight.

Nicotinate and Nicotinamide Metabolic Network:

Nicotinate and nicotinamide are precursors of the coenzymes nicotinamide-adenine dinucleotide (NAD+) and nicotinamide-adenine dinucleotide phosphate (NADP+), which, when reduced, are important cofactors in many redox reactions. When nicotinic acid is deficient, pellagra can result. It was found that mutations in the nicotinamide N-methyl transferase (NNMT) could lead to risk of spina bifida (Lu et al., *Mol. Teratology,* 82:670-675, 2008) and it is possible that alterations to this pathway could lead to birth defects and thus, measurements of fold change of metabolites in this pathway could indicate a compound's teratogenicity Pantothenate and CoA Biosynthesis Network:

A significant number of putative metabolite annotations from the pantothenate and CoA biosynthesis network exhibited statistically significant changes across a number of compounds. The network figure for the Pantothenate and CoA biosynthesis network shows the putative annotations, marked with either a black circles, or a grey circle (those metabolites highlighted that are grey circles are isobaric while those that are black circles have unique masses.)

The pantothenate and CoA biosynthesis network produces CoA which attaches to a long-chain fatty acid to eventually form acetyl-CoA which enters the TCA cycle resulting in ATP synthesis. Thus aberrations to this network can result in energy production abnormalities, which can, in turn, cause severe impairment of cellular processes. Of most importance in the network is the pantothenate availability, as the phosphorylation of this metabolite is the rate-limiting step of CoA production and it has been observed that impaired energy result along with neurological symptoms (Rock et al., *J. Biol. Chem.*, 275:1377-1383, 2000) as a result of low levels of pantothenate. Furthermore, it was found that maternal pantothenate deficiency results in a teratogenic effect on the fetus (Nelson et al., *J. Nutr.*, 62:395-405, 1957; Baker et al., *Am. J. Clin. Nutr.*, 28:56-65, 1975). Given these associations of alterations to the pantothenate network and birth defects, it is plausible to correlate chemicals which cause abundance changes of metabolites within the pantothenate network with the likelihood that particular chemicals causing these changes may in turn have the ability to disrupt human development, and possibly induce birth defects.

Glutathione Network:

The glutathionine network plays a role in oxidative stress. Glutathione, an essential metabolite of the network, can exist in a reduced or oxidized state. In its reduced state, glutathione has the ability to protonate free radicals and, thus, acts as an antioxidant. Oxidative stress is associated with neurodegenerative disease (Simonian et al., *Ann Rev Pharm. Tox.*, 36:83-106, 1996), pulmonary disease (Repine et al., *Am. J. Resp. Critical Care Med.*, 156:341-357, 1997), and has even been related to preeclampsia (Walsh et al., *Semin. Reprod. Med.*, 16:93-104, 1998). There have been several studies which relate glutathione levels with birth defects. For example, Isibashi et al. had found that glutathione depletion and oxidative stress strongly implicate birth defects in animals (Isibashi et al., *Free Rad. Biol. Med.*, 22:447-454, 1997). Zhao et al. also found such a relationship in humans and discovered that women with neural tube defect pregnancies had higher levels of oxidized glutathione than the control group (Zhao et al., *Birth Defects Research Part A: Clinical and Molecular Teratology*, 76:230-236, 2006). Due to this association of the glutathione network and birth defects, it is possible to further study the fold changes for the metabolites within this network in order to classify each chemical compound as a potential teratogen or not.

Arginine and Proline Metabolic Network:

Several statistically significantly altered small molecules within the arginine and proline metabolic network were found. Most interesting is the presence of dimethylarginine, arginine, and citrulline. Nitric oxide synthase converts L-Arginine to L-Citrulline. Dimethylarginine is an inhibitor of Nitric Oxide Synthase. Studies have found that nitric oxide synthase is essential for neural tube closure (Nachmany et al., *J. Neurochem.*, 96:247-253, 2006) and so modifications to this reaction and to levels of L-citrulline and L-arginine could indicate a chemical compound's ability to induce birth defects.

All references cited herein are incorporated by reference. In addition, the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

REFERENCES

Abramovici, A., Shaklai, M. & Pinkhas, J. (2005): Myeloschisis in a six weeks embryo of a leukemic woman treated with busulfan. Teratology 18, 241-245.

Adler, S., Pellizzer, C., Hareng, L., Hartung, T. & Bremer, S. (2008): First steps in establishing a developmental toxicity test method based on human embryonic stem cells. Toxicology In vitro 22, 200-211.

Alexander, P., Chau, L. & Tuan, R. (2007): Role of nitric oxide in chick embryonic organogenesis and dysmorphogenesis. Birth Defects Research Part A: Clinical and Molecular Teratology 79, 581-594.

Alpert, A. (1990): Hydrophilic-interaction chromatography for the separation of peptides, nucleic acids, and other polar compounds. Journal of Chromatography 499, 177-196.

Anderson, D., Kieth, J., Novak, P. & Elliot, M. (2002): teratogen. In: Mosby's Medical, Nursing & Allied Health Dictionary), p. 1690, Mosby, St. Louis, Mo.

Baker H, Fran O, Thomson A, Langer A, Munves E, DeAngelis B, et al. Vitamin profile of 174 mothers and newborns at parturition. Am J Clin Nutr. 1975; 28:56-65.

Barr, D., Silva, M., Kato, K., et al. (2003): Assessing human exposure to phthalates using monoesters and their oxidized metabolites as biomarkers. Environmental Health Perspective 11, 1148-1151.

Bauman, K. A. (1998): Neuropathology of infantile autism. Journal of Neuropathology and Experimental Neurology 57, 645-652.

Bogdanov, M., Matson, W. R., Wang, L., et al. (2008): Metabolomic profiling to develop blood biomarkers for Parkinson's disease. Brain 131, 389-396.

Brent, R. & Holmes, L. (1988): Clinical and basic science from the thalidomide tragedy: what have we learned about the causes of limb defects? Teratology 38, 241-251.

Brieman, L. (2001): Random Forests. Machine Learning 45, 5-32.

Cezar, G., Quam, J., Smith, A., et al. (2007): Identification of small molecules from human embryonic stem cells using metabolomics. Stem Cells and Development 16, 869-882.

Chapin, R., Augustin-Rauch, K., Beyer, B., et al. (2008): State of the art in developmental toxicity screening methods and a way forward: a meeting report addressing embryonic stem cells, whole embryo culture, and zebrafish. Birth Defects Research Part B: Developmental and Reproductive Toxicology 83, 446-456.

DiLiberti, J., Farndon, P., Dennis, N. & Curry, C. (1984): The fetal valproate syndrome. Am. J. Med. Genetic. 19, 473-481.

Genschow, E., Scholz, G., Brown, N., et al. (2000): Development of prediction models for three in vitro embryotoxicity tests in an ECVAM validation study. In vitro Molecular Toxicology 13, 51-66.

Genschow, E., Spielmann, H., Scholz, G., et al. (2002): The ECVAM international validation study on in vitro embryotoxicity tests: results of the definitive phase and evaluation of prediction models. European Centre for the Validation of Alternative Methods. Alternatives to Laboratory Animals 30, 151-176.

Goodacre, R., Vaidyanathan, S., Dunn, W. B., Harrigan, G. G. & Kell, D. B. (2004): Metabolomics by numbers: acquiring and understanding global metabolite data. Trends in Biotechnology 22, 245-252.

Isibashi M, Akazawa S, Sakamake H, al. e. Oxygen-induced embryopathy and the significance of glutathione-dependent antioxidant system in the rate embryo during early organogenesis. Free Raid Biol Med. 1997; 22:447-54.

Kind, T., Tolstikov, V., Fiehn, O. & Weiss, R. (2007) A comprehensive urinary metabolomic approach for identifying kidney cancer. Analytical Biochemistry 363, 185-195.

Lee, Q. & Juchau, M. (2005): Dysmorphogenic effects of nitric oxide (NO) and NO-synthase inhibition: studies with intra-amniotic injections of sodium nitroprusside and N-monmethyl-L-arginine. Teratology 49, 452-464.

Liaw, A. & Wiener, M. (2002): Classification and regression by random forest. R News: The Newsletter of the R Project 2, 18-22.

Lu W, Zhu H, Wen S, Yang W, Shaw G, Lammer E, et al. Nicotinamide N-methyl transferase (NNMT) gene polymorphisms and risk for spina bifida. Birth Defects Research Part A: Clinical and Molecular Teratology. 2008; 82(10):670-5.

Lujan, R., Shigemoto, R. & Lopez-Bendito, G. (2005): Glutamate and GABA receptor signaling in the developing brain. Neuroscience 130, 567-580.

Marx-Stoelting, P., Adriaens, E., Ahr, H., et al. (2009): A review of the implementation of the embryonic stem cell test (EST). The report and recommendations of an ECVAM/ReProTect Workshop. Alternatives to Laboratory Animals 37, 313-328.

Miller, M. & Stromland, K. (1999): Teratogen update: Thalidomide: a review, with a focus on ocular findings and new potential uses. Teratology 60, 306-321.

Nachmany, A., Gold, V., Tsur, A., Arad, D. & Weil, D. (2006): Neural tube closure depends on nitric oxidase synthase activity. J. Neurochem. 96, 247-253.

Nelson M, Wright H, Barid C, Evans M. Teratogenic effects of pantothenic acid deficiency in the rat. J Nutr. 1957; 62:395-405.

Nieden, N. Z., Ruf, L., Kempka, G., Hildebrand, H. & Ahr, H. (2001): Molecular markers in embryonic stem cells. Toxicology in vitro 15, 455-461.

Paquette, J., Kumpf, S., Streck, R., Thomson, J., Chapin, R. & Stedman, D. (2008): Assessment of the embryonic stem cell test and application and use in the pharmaceutical industry. Birth Defects Research Part B: Developmental and Reproductive Toxicology 83, 104-111.

Pearl, P. & Bigson, K. (2004): Clinical aspects of the disorder of GABA metabolism in children. Current Opinion in Neurology 17, 107-113.

Pearl, P., Taylor, J., Trzcinski, S. & Sokohl, A. (2007): The Pediatric neurotransmitter disorders. Journal of Child Neurology 22, 606-616.

Qu, Q., Melikian, A. A., Li, G., et al. (2000): Validation of biomarkers in humans exposed to benzene: Urine metabolites. American Journal of Industrial Medicine 37, 522-531.

Repine J, Bast A, Lankhorst I, Group OSS. Oxidative stress in chronic obstructive pulmonary disease. American Journal of Respiratory and Critical Care Medicine. 1997; 156(2): 341-57.

Rock C, Calder R, Karim M, Jackowski S. Pantothenate kinase regulation of the intracellular concentration of coenzyme A. The Journal of Biological Chemistry. 2000; 275: 1377-83.

Sabatine, M., Liu, E., Morrow, D., et al. (2005): Metabolomic identification of novel biomarkers of myocardial ischemia. Circulation 112, 3868-3875.

Selderslaghs, I., Rompay, A., De Coen, W. & Witters, H. (2009): Development of a screening assay to identify teratogenic and embryotoxic chemicals using the zebrafish embryo. Reproductive Toxicology 28, 308-320.

Serkova, N., Zhang, Y., Coatney, J., et al. (2007) Early detection of graft failure using the blood metabolic profile of a liver recipient. Transplantation 83, 517-521.

Shanks, N., Greek, R. & Greek, J. (2009): Are animal models predictive for humans? Philosophy, Ethics, and Humanities in Medicine 4, 2.

Shinka, T., Ohfu, M., Hirose, S. & Kuhara, T. (2003): Effect of valproic acid on the urinary metabolic profile of a patient with succinic semialdehyde dehydrogenase deficiency. Journal of Chromatography B 792, 99-106.

Simonian N, Coyle J. Oxidative stress in neurodegenerative diseases. Annual Review of Pharmacology and Toxicology. 1996; 36:83-106.

Sreekumar, A., Poisson, L., Rajendiran, T., et al. (2009): Metabolomic profiles delineate potential role for sarcosine in prostate cancer progression. Nature 457, 910-914.

Summar, M. (2001): Current strategies for the management of neonatal urea cycle disorders. Pediatr 131, S30-S39.

Tan, D., Manchester, L., Reiter, R., et al. (1998): A novel melatonin metabolite, cyclic 3-hydroxymelatonin: a biomarker of in vitro hydroxyl radical generation. Biochemical and Biophysical Research Communications 253, 614-620.

Tashiro, A., Sandler, V., Toni, N., Zhao, C. & Gage, F. (2006): NMDA-receptor-mediated, cell-specific integration of new neurons in adult dentate gyrus. Nature 442, 929-933.

Thomson, J., Itskovitz-Eldor, J., Shapiro, S., et al. (1998): Embryonic stem cell lines derived from human blastocysts. Science 282, 1145-1147.

Toms, D. (1962): Thalidomide and congenital abnormalities. Lancet 2, 400.

Vriend, J. & Alexiuk, N. (1996): Effects of valproate on amino acid and monoamine concentration in striatum of audiogenic seizure-prone balb/c mice. Molecular and Chemical Neruopathology 27, 307-324.

Walsh S. Maternal-placental interactions of oxidative stress and antioxidants in preeclampsia. Semin Reprod Med. 1998; 16(1):93-104.

Zhao W, Mosley B, Cleves M, Melnyk S, James S, Hobbs C. Neural tube defects and maternal biomarkers of folate, homocysteine, and glutathione metabolism. Birth Defects Research Part A: Clinical and Molecular Teratology. 2006; 76(4):230-6.

What is claimed is:

1. A method of predicting human developmental toxicity of a test compound, the method comprising the steps of:
   (a) culturing human stem-cell like cells (hSLCs):
      (i) in the presence of a first known developmental toxicant; and
      (ii) in the absence of the first known developmental toxicant;
   (b) detecting a plurality of metabolites having a molecular weight of less than about 3000 Daltons associated with hSLCs exposed to the first known developmental toxicant in comparison with hSLCs not exposed to the first known developmental toxicant in order to identify a difference in metabolic response of hSLCs exposed to the first known developmental toxicant in comparison with hSLCs not exposed to the first known developmental toxicant;
   wherein the plurality of metabolites is detected by mass spectrometry;
   (c) generating a set of mass features associated with exposure of hSLCs to the first developmental toxicant by analyzing the difference in metabolic response;
   (d) repeating steps a)-c) multiple times, each time with a different known developmental toxicant;
   (e) grouping mass features generated from each exposure to a developmental toxicant to obtain a reference profile of mass features correlating with developmental toxicity;
   (f) culturing hSLCs;
      (i) in the presence of a test compound; and
      (ii) in the absence of the test compound;
   (g) detecting a plurality of metabolites having a molecular weight of less than about 3000 Daltons associated with hSLCs exposed to the test compound in comparison with hSLCs not exposed to the test compound in order to identify a difference in metabolic response of hSLCs exposed to the test compound in comparison with hSLCs not exposed to the test compound;

wherein the plurality of metabolites is detected by mass spectrometry; and (h) generating a set of mass features associated with exposure of hSLCs to the test compound by analyzing the difference in metabolic response;

(i) comparing the set of mass features associated with exposure of hSLCs to the test compound of step (h) to the reference profile of mass features correlating with developmental toxicity of step (e) to predict the human developmental toxicity of the test compound.

2. The method of claim 1, wherein the hSLCs cultured in the absence of a known developmental toxicant are further cultured during step a) and/or step (f) in the presence of a known non-developmental toxicant.

3. The method according to claim 1, wherein the hSLCs comprise human embryonic stem cells (hESCs), human induced pluripotent (iPS) cells, or human embryoid bodies.

4. The method according to claim 1, wherein the reference profile comprises a biomarker profile characteristic of hSLC response to a developmental toxicant.

5. The method according to claim 1, wherein the mass spectrometry is liquid chromatography/electrospray ionization mass spectrometry.

6. The method according to claim 1, wherein the reference profile of mass features correlating with developmental toxicity comprises five or more of the small molecules listed in Table 8.

7. The method according to claim 1, wherein the reference profile of mass features correlating with developmental toxicity comprises ten or more of the small molecules listed in Table 8.

8. The method according to claim 1, wherein the reference profile of mass features correlating with developmental toxicity comprises one or more of the small molecules listed in Table 10.

9. The method according to claim 1, wherein the reference profile of mass features correlating with developmental toxicity comprises the fifteen small molecules listed in Table 10.

10. The method according to claim 1, wherein mass spectrometry comprises gas phase ion spectrophotometer and/or laser-desorption/ionization mass spectrometry.

11. The method according to claim 1, wherein mass spectrometry comprises matrix assisted laser desorption/ionization (MALDI) mass spectrometry and/or surface-enhanced laser desorption/ionization (SELDI).

12. The method according to claim 1, wherein mass spectrometry comprises MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry, secondary ion mass spectrometry (SIMS), and/or ion mobility spectrometry.

13. The method according to claim 1, wherein culturing the hSLCs in the presence of a known developmental toxicant of step (a) comprises culturing hSLCs at a dose of the known developmental toxicant selected from:

a dose corresponding to the EC50 or IC50 concentration of the known developmental toxicant;

a dose below the EC50 or IC50 concentration of the known developmental toxicant; or a dose of the known developmental toxicant equivalent to the circulating concentration in maternal serum.

14. The method according to claim 1, wherein culturing the hSLCs in the presence of test compound comprises culturing hSLCs at a dose of the test compound selected from:

a dose representing the EC50 or IC50 concentration of the test compound;

a dose below the EC50 or IC50 concentration of the test compound; or a dose of the test compound equivalent to the circulating concentration in maternal serum.

15. The method according to claim 1, wherein the known developmental toxicant is selected from diphenylhydantoin, methotrexate, 5-fluorouracil, accutane, amiodarone, busulfan, carbamazepine, cyclophosphamide, cytosine arabinoside, hydroxyurea, retinoic acid, rifampicin, thalidomide, and/or valproic acid.

16. The method according to claim 1, wherein step (a) is repeated for each of the known developmental toxicants 5-fluorouracil, busulfan, cytosine arabinoside, hydroxyurea, retinoic acid, thalidomide, and valproic acid.

17. The method according to claim 16, wherein the reference profile of mass features correlating with developmental toxicity comprises the 142 mass features shown in Table 4.

18. The method according to claim 16, wherein step (a) is further repeated for each of the known developmental toxicants diphenylhydantoin, methotrexate, accutane, amiodarone, carbamazepine, cyclophosphamide, and rifampicin.

19. The method according to claim 2, wherein step (a) is repeated for each of the known developmental toxicants and known non-developmental toxicants shown in Table 11.

20. The method according to claim 19, wherein the reference profile of mass features correlating with developmental toxicity comprises the 15 mass features shown in Table 10.

21. A method of producing a reference profile of mass features correlating with developmental toxicity, the method comprising the steps of:

(a) culturing human stem-cell like cells (hSLCs):

(i) in the presence of a first known developmental toxicant; and (ii) in the absence of the first known developmental toxicant;

(b) detecting a plurality of metabolites having a molecular weight of less than about 3000 Daltons associated with hSLCs exposed to the first known developmental toxicant in comparison with hSLCs not exposed to the first known developmental toxicant in order to identify a difference in metabolic response of hSLCs exposed to the first known developmental toxicant in comparison with hSLCs not exposed to the first known developmental toxicant;

wherein the plurality of metabolites is detected by mass spectrometry;

(c) generating a set of mass features associated with exposure of hSLCs to the first developmental toxicant by analyzing the difference in metabolic response;

(d) repeating steps a)-c) multiple times, each time with a different known developmental toxicant;

(e) grouping mass features generated from each exposure to a developmental toxicant to obtain a reference profile of mass features correlating with developmental toxicity.

22. The method of claim 21, wherein the hSLCs cultured in the absence of a known developmental toxicant are further cultured during step a) in the presence of a known non-developmental toxicant.

* * * * *